US008614081B2

(12) United States Patent
Krebber et al.

(10) Patent No.: US 8,614,081 B2

(45) Date of Patent: Dec. 24, 2013

(54) NITRILASE BIOCATALYSTS

(75) Inventors: Anke Krebber, Palo Alto, CA (US); Emily Mundorff, Poughkeepsie, NY (US); Marissa Mock, Moorpark, CA (US); Spiros Kambourakis, Pasadena, CA (US)

(73) Assignee: Codexis, Inc., Redwood City, CA (US)

( * ) Notice: Subject to any disclaimer, the term of this patent is extended or adjusted under 35 U.S.C. 154(b) by 27 days.

(21) Appl. No.: 13/381,155

(22) PCT Filed: Jul. 22, 2010

(86) PCT No.: PCT/US2010/042950

§ 371 (c)(1), (2), (4) Date: Dec. 28, 2011

(87) PCT Pub. No.: WO2011/011630

PCT Pub. Date: Jan. 27, 2011

(65) Prior Publication Data

US 2012/0142063 A1 Jun. 7, 2012

Related U.S. Application Data

(60) Provisional application No. 61/228,152, filed on Jul. 23, 2009.

(51) Int. Cl.

| | |
|---|---|
| ***C12N 9/78*** | (2006.01) |
| ***C12P 7/40*** | (2006.01) |
| ***C12N 1/21*** | (2006.01) |
| ***C12N 15/63*** | (2006.01) |
| ***C07H 21/04*** | (2006.01) |

(52) U.S. Cl.

USPC ... 435/227; 435/136; 435/252.33; 435/320.1; 536/23.2

(58) Field of Classification Search

USPC .......... 435/136, 227, 252.33, 320.1; 536/23.2

See application file for complete search history.

(56) References Cited

U.S. PATENT DOCUMENTS

| | | | |
|---|---|---|---|
| 4,469,863 | A | 9/1984 | Tso et al. |
| 5,216,141 | A | 6/1993 | Benner |
| 5,386,023 | A | 1/1995 | Sanghvi et al. |
| 5,539,082 | A | 7/1996 | Nielsen et al. |
| 5,602,240 | A | 2/1997 | De Mesmaeker et al. |
| 5,637,684 | A | 6/1997 | Cook et al. |
| 5,644,048 | A | 7/1997 | Yau |
| 5,719,262 | A | 2/1998 | Buchardt et al. |
| 5,773,571 | A | 6/1998 | Nielsen et al. |
| 5,786,461 | A | 7/1998 | Buchardt et al. |
| 6,107,470 | A | 8/2000 | Nielsen et al. |
| 6,117,679 | A | 9/2000 | Stemmer |
| 6,376,246 | B1 | 4/2002 | Crameri et al. |
| 6,586,182 | B1 | 7/2003 | Patten et al. |
| 7,521,216 | B2 | 4/2009 | DeSantis et al. |
| 2008/0220990 | A1 | 9/2008 | Fox |
| 2009/0312196 | A1 | 12/2009 | Colbeck et al. |

FOREIGN PATENT DOCUMENTS

| | | | |
|---|---|---|---|
| WO | 92/20702 | A1 | 11/1992 |
| WO | 94/25477 | A2 | 10/1994 |
| WO | 95/22625 | A1 | 8/1995 |
| WO | 97/00078 | A1 | 1/1997 |
| WO | 97/35966 | A1 | 10/1997 |
| WO | 98/27230 | A1 | 6/1998 |
| WO | 01/75767 | A1 | 10/2001 |
| WO | 2005/100580 | A1 | 10/2005 |
| WO | 2009/008908 | A2 | 1/2009 |

OTHER PUBLICATIONS

Altschul, S., et al., "Basic local alignment search tool," J. Mol. Biol., 215: 403-410 (1990).

Altschul, S.F., et al., "Gapped Blast and PSI-BLAST: a new generation of protein database search programs," Nucleic Acids Res., 25(17):3389-3402 (1997).

Baldino, Jr., F., et al., "High-Resolution in Situ Hybridization Histochemistry," Methods Enzymology, 168:761-777 (1989).

Batzer, M.A., "Erratum: Structure and variability of recently inserted Alu family members", Nucleic Acids Res 19:698-699 [1991].

Beaucage, S.L., et al., "Deoxynucleoside phosphoamidites—A new class of key intermediates for deoxypolynucleotide synthesis," Tetrahedron Letters, 22(20):1859-62 (1981).

Beaucage, S.L., et al., "The Functionalization of Oligonucleotides Via Phosphoramidite Derivatives," Tetrahedron, 49(10):1925-1963 (1993).

Black, M.E., et al., "Creation of drug-specific herpes simplex virus type 1 thymidine kinase mutants for gene therapy," Proc Natl Acad Sci USA, 93:3525-3529 (1996).

Bolton, E.T., et al., "A General Method for the Iisolation of RNA Complementary to DNA," Proc. Natl. Acad. Sci. USA 48:1390 ( 1962).

Botstein, D., et al., "Strategies and applications of in vitro mutagenesis," Science, 229(4719):1193-1201, 1985.

Bray, P., et al., "Human cDNA clones for four species of G alpha s signal transduction protein," Proc. Natl. Acad. Sci USA, 83:8893-8897 [1986].

Brill, W.K.-D., et al., "Synthesis of Oligodeoxynucleoside Phosphorodithioates via Thioamidites," J. Am. Chem. Soc., 111:2321-2322 ( 1989).

Caldwell, R.C., et al., "Mutagenic PCR," PCR Methods Appl., 3:S136-S140 (1994).

Carlsson, C., et al., "Screening for genetic mutations," Nature, 380:207 (1996).

Carter, P., "Site-directed mutagenesis," Biochem. J., 237:1-7, 1986.

Christians, F.C., et al., "Directed evolution of thymidine kinase for AZT phosphorylation using DNA family shuffling," Nat. Biotechnol., 17:259-264, 1999.

Crameri, A., et al., "DNA shuffling of a family of genes from diverse species accelerates directed evolution", Nature, 391:288-291, 1998.

Crameri, A., et al., "Improved green fluorescent protein by molecular evolution using DNA shuffling,"Nat. Biotechnol., 14(3):315-319, 1996.

(Continued)

*Primary Examiner* — Chih-Min Kam

(74) *Attorney, Agent, or Firm* — Codexis, Inc.

(57) ABSTRACT

The present disclosure relates to polypeptides having nitrilase activity, polynucleotides encoding the polypeptides, and methods of using the polypeptides.

131 Claims, No Drawings

(56) References Cited

OTHER PUBLICATIONS

Crameri, A., et al., "Molecular evolution of an arsenate detoxification pathway by DNA shuffling," Nat. Biotechnol., 15(5):436-438, 1997.
Dale, S.J., et al., "Oligonucleotide-directed random mutagenesis using the phosphorothioate method," Methods Mol. Biol., 57:369-74, 1996.
Dempcy, R.O., et al., "Synthesis of a thymidyl pentamer of deoxyribonucleic guanidine and binding studies with DNA homopolynucleotides," Proc. Natl. Acad. Sci. USA, 92:6097-6101 [1995].
Desantis, G., et al., "Creation of a Productive, Highly Enantioselective Nitrilase through Gene Site Saturation Mutagenesis (GSSM)," Journal of the American Chemical Society, 125(38):11476-11477 (2003).
Egholm, M., et al., "Peptide Nucleic Acids (PNA) . Oligonucleotide Analogues with an Acbiral Peptide Backbone," J. Am. Chem. Soc., 114:1895-1897 (1992).
Eisenberg, D., et al., "Analysis of Membrane and Surface Protein Sequences with the Hydrophobic Moment Plot," J. Mol. Biol., 179:125-142 (1984).
Fernandes, B.C.M., et al., "Nitrile Hydratase Activity of a Recombinant Nitrilase," Adv Synth Catal, 348:2597-2603 (2006).
Freier, S.M., et al., "Improved free-energy parameters for predictions of RNA duplex stability," Proc. Natl. Acad. Sci USA, 83:9373-9377 (1986).
Henikoff, S.,et al., "Amino acid substitution matrices from protein blocks," Proc. Natl. Acad. Sci., 89:10915-10919, 1992.
Jung, P.M., et al., "Hybridization of Alternating Cationic/Anionic Oligonucleotides to RNA Segments," Nucleosides & Nucleotides, 13:1597-1605 (1994).
Kierzek, R., et al., "Polymer-Supported RNA Synthesis and Its Application to Test the Nearest-Neighbor Model for Duplex Stability," Biochemistry, 25:7840-7846 (1986).
Kiziak, C., et al., "Identification of Amino Acid Residues Responsible for the Enantioselectivity and Amide Formation Capacity of the Arylacetonitrilase from *Pseudomonas fluorescens* EBC191," Applied and Environmental Microbiology, 75(17):5592-5599 [2009].
Kramer, B., et al., "Different base/base mismatches are corrected with different efficiencies by the methyl-directed DNA mismatch-repair system of *E. coli*," Cell, 38(3):879-887, 1984.
Lathe, R., et al., "Plasmid and bacteriophage vectors for excision of intact inserts," Gene, 57:193-201 (1987).
Letsinger, R.L., et al., "Cationic Oligonucleotides," J. Am. Chem. Soc., 110:4470-4471 (1988).
Letsinger, R.L., et al., "Effects of pendant groups at phosphorus on binding properties of d-ApA analogues," Nucl. Acids. Res. 14(8):3487-3499 (1986).
Ling, M., et al., "Approaches to DNA Mutagenesis:An Overview," Anal. Biochem., 254:157-78 (1999).
Mag, M., et al., "Synthesis and selective cleavage of anoligodeoxynucleotide containing a bridged intemucleotide5'-phosphorothioate linkage," Nucl. Acids. Res. 19(7):1437-1441 (1991).
Matthes, H.W.D., et al., "Simultaneous rapid chemical synthesis of over one hundred oligonucleotides on a microscale," EMBO J., 3(4):801-05 (1984).
Meier, C., et al., "Peptide Nucleic Acids (PNAs)—Unusual Properties of Nonionic Oligonucleotide Analogues," Angew. Chem. Int. Ed. Engl., 31(8):1008-1010 (1992).
Minshull, J., et al., "Protein evolution by molecular breeding," Curr. Op. Chem. Biol., 3(3):284-290, 1999.
Needleman, S., et al., "A general method applicable to the search for similarities in the amino acid sequence of two proteins," J. Mol. Biol. 48:443-453 (1970).
Pauwels, R., et al., "Biological Activity of New 2-5A Analogues," Chemica Scripta 26:141-145 (1986).
Pearson, W.R., "Improved tools for biological sequence comparison," Proc. Nat'l. Acad. Sci. USA, 85:2444-2448 [1988].
Rychlik, W., et al., "Optimization of the annealing temperature for DNA amplification in vitro," Nucleic Acids Res, 18(21):6409-6412 (1990).
Sawai, H., "Synthesis and Properties of Oligoadenylic Acids Containing 2'-5' Phosphoramide Linkage," Chem Lett, N5:805-808 (1984).
Singh, R., et al., "Nitrilase and Its Application as a Green Catalyst," Chemistry & Biodiversity, 3:1279-1287 [2006].
Smith, M., "In vitro mutagenesis," Ann. Rev. Genet., 19:423-462, 1985.
Smith, T., et al., "Comparison of Biosequences," Adv. Appl. Math, 2:482-489 (1981).
Stemmer, W., "DNA Shuffling by Random Fragmentation and Reassembly: In vitro Recombination for Molecular Evolution," Proc. Natl. Acad. Sci. USA, 91:10747-10751 (1994).
Stemmer, W.P.C., "Rapid evolution of a protein in vitro by DNA shuffling", Nature, 370:389-391, 1994.
Suggs, S.V., et al., "Use of synthetic oligodeoxyribonucleotides for the isolation of specific cloned DNA sequenes," in Developmental Biology Using Purified Genes (Brown et al., eds.), pp. 683-693, Academic Press (1981).
Thuku, R.N., et al., "Microbial nitrilases: versatile, spiral forming, industrial enzymes," Journal of Applied Microbiology, pp. 1-25 [2008].
Von Kiedrowski, G., et al. , "Parabolic Growth of a Self-Replicating Hexadeoxynucleotide Bearing a 3'-5'-Phosphoamidate Linkage," Angew. Chem. Intl. Ed. English 30(4):423-426 (1991).
Wells, J.A., et al., "Cassette mutagenesis: an efficient method for generation of multiple mutations at defined sites," Gene, 34:315-323 (1985).
Wetmur, J. G., "DNA Probes: Applications of the Principles of Nucleic Acid Hybridization," Crit Rev Biochem Mol Biol, 26(3/4):227-259 (1991).
Wu, S., et al., "Protein Engineering of *Acidovorax facilis* 72WNitrilase for Bioprocess Development," Biotechnology and Bioengineering, 97(4):689-693 (2007).
Wu, S., et al., "Protein Engineering of Nitrilase forChemoenzymatic Production of Glycolic Acid," Biotechnology and Bioengineering, 99(3):717-721 (2008).
Zhang, J-H., et al., "Directed evolution of a fucosidase from a galactosidase by DNA shuffling and screening ," Proc. Nat. Acad. Sci., U.S.A., 94:4504-4509 (1997).
Zhao, H., et al., "Molecular evolution by staggered extension process (StEP) in vitro recombination," Nat. Biotechnol., 16:258-261 (1998).
Zhu, D., et al., "Discovery of a mandelonitrile hydrolase from *Bradyrhizobium japonicum* USDA110 by rational genome mining," Journal of Biotechnology, 129(4):645-650 [2007].
Genbank Accession No. NP_773042.1, "unnamed protein product [*Bradyrhizobium japonicum* USDA 110]," downloaded from www.ncbi.nlm.nih.gov/ on Apr. 6, 2012 (BCT—Jan. 20, 2012).
Genbank Accession No. NC_004463, "*Bradyrhizobium japonicum* USDA 110 chromosome, complete genome," downloaded from www.ncbi.nlm.nih.gov/ on Apr. 6, 2012 (BCT—Jan. 20, 2012).
Egholm, M., et al., "PNA hybridizes to complementary oligonucleotides obeying the Watson-Crick hydrogen-bonding rules," Nature, 365:566-568 (1993).

NITRILASE BIOCATALYSTS

1. TECHNICAL FIELD

The present disclosure relates to nitrilase biocatalysts and methods of using the biocatalysts.

2. REFERENCE TO SEQUENCE LISTING, TABLE OR COMPUTER PROGRAM

The Sequence Listing is concurrently submitted herewith the specification as an ASCII formatted text file via EFS-Web with a file name of CX2-029WO1_ST25.txt with a creation date of Jul. 22, 2010, and a size of 826 Kbytes. The Sequence Listing filed via EFS-Web is part of the specification and is hereby incorporated in its entirety by reference herein.

3. BACKGROUND

Nitrilases are a class of enzymes capable of converting nitriles to it corresponding carboxylic acids with the release of ammonia. In some instances, the enzymes release an amide product (Fernandes et al., 2006, Adv Synth Catal 348, 2597-2603). Their high chemical specificity and frequent enantioselectivity makes them attractive biocatalysts for the production of fine chemicals and pharmaceutical intermediates, such as -amino-, -hydroxy- or -methylcarboxylic acids. A nitrile group offers advantages in devising synthetic routes in that it is often easily introduced into a molecular structure and can be carried through many processes as a masked acid or amide group. However, their conversion to corresponding amides and carboxylic acids requires harsh conditions and generates significant chemical waste. Enzymatic hydrolysis of nitriles can be performed under mild conditions and can also take advantage of stereospecific enzymatic hydrolysis and nitrile reracemization to provide highly enantioselective conversions. Nitrilases that act on aromatic or aliphatic nitriles have been described. Given the utility of these enzymes, it is desirable to identify nitrilases with performance characteristics that make them applicable to a variety of reaction conditions and substrates.

4. SUMMARY

The present disclosure relates to nitrilase polypeptides having improved enzyme properties as compared to the naturally occurring nitrilase enzyme. The nitrilase polypeptides are capable of converting the substrate of structural formula (I) to the product of structural formula (II):

$$R^1\text{—CN} \longrightarrow R^1\text{—COOH}$$

(I) (II)

wherein $R^1$ is a substituted or unsubstituted phenyl; a substituted or unsubstituted phenylalkyl($C_1$-$C_3$); a substituted or unsubstituted alkyl($C_3$-$C_8$) or a substituted or unsubstituted heteroalkyl. In some embodiments, the nitrilase polypeptides have improved stability to temperature or solvent. In some embodiments, the nitrilase polypeptides have improved stability as compared to the polypeptide of SEQ ID NO:2 to conditions of 3 hrs at 40° C. and/or 3 hrs in 10% methanol.

In some embodiments, the nitrilase polypeptide has improved thermo- and/or solvent stability as compared to the reference polypeptide of SEQ ID NO:2 and comprises an amino acid sequence that is at least 80%, 85%, 86%, 87%, 88%, 89%, 90%, 91%, 92%, 93%, 94% 95%, 96%, 97%, 98%, or 99% or more identical to the sequence of the reference sequence of SEQ ID NO:2.

In some embodiments, the nitrilase polypeptide has improved thermo- and/or solvent stability as compared to the reference polypeptide of SEQ ID NO:2 and comprises an amino acid sequence that is at least 80%, 85%, 86%, 87%, 88%, 89%, 90%, 91%, 92%, 93%, 94% 95%, 96%, 97%, 98%, or 99% or more identical to the sequence of the reference sequence of another engineered nitrilase, in particular a reference sequence selected from SEQ ID NO: 6, 84, 122, 130, 138, 358, 360, or 362.

In some embodiments, the nitrilase polypeptide having improved thermo- and/or solvent stability comprises an amino acid sequence that has one or more residue differences as compared to SEQ ID NO:2 at residue positions selected from: X91; X108; X139; X166; X230; X266; and X309. In some embodiments, the amino acid residue at the residue positions are selected from: X91 is R or K; X108 is S, N or Q; X139 is W or F; X166 is F, W, Y or L; X230 is Y, F, W, V, L, A, or I; X266 is V, L, A or I; and X309 is V, L, A or I. Other residue positions where residue differences can be present as compared to SEQ ID NO:2 for thermo- and/or solvent stable polypeptides are provided in the detailed description.

In some embodiments, the nitrilase polypeptides of the disclosure has at least 1.1-fold improved activity for converting the substrate of formula I to the product of formula II relative to the activity of SEQ ID NO:2. In some embodiments, these activity improvements may present independently of or in combination with the improvements in thermo- and/or solvent stability.

In some embodiments, the nitrilase polypeptide with improved enzymatic activity comprises an amino acid sequence that has one or more residue differences as compared to SEQ ID NO:2 at the residue positions selected from: X23, X30, X37, X40, X49, X54, X55, X65, X73, X85, X121, X130, X132, X134, X139, X152, X161, X163, X170, X171, X172, X173, X191, X197, X199, X200, X201, X203, X209, X217, X225, X230, X233, X240, X267, X269, X272, X282, X288, X289, X293, X295, X297, X303, X317, X319, X323, X327, X330, X332, and X334. In some embodiments, the amino acid residues at the residue positions affecting enzymatic activity is selected from: X23 is T; X30 is L; X37 is T; X40 is E; X49 is V; X54 is M, V, A, F, or Y; X55 is F; X65 is T; X73 is E; X85 is R; X121 is K; X130 is R; X132 is H, M, L or F; X134 is A; X139 is F or W; X152 is T; X161 is N; X163 is H, W or G; X170 is G; X171 is R; X172 is C; X173 is V; X191 is A, C, I or F; X197 is L, M, or N; X199 is C, H, F, C, V, T, W, M, A, I, F or P; X200 is S; X201 is G; X203 is A; X209 is R; X217 is T; X225 is T; X230 is A, V or Y; X233 is T; X240 is R; X267 is A; X269 is R or P; X272 is E; X282 is I; X288 is T; X289 is V; X293 is T or V; X295 is N; X297 is G, A or V; X303 is P; X317 is A; X319 is M; X323 is G or K; X327 is V; X330 is I; X332 is I or S; and X334 is S, L or I. As noted above, the residue differences affecting activity may be present independently or in combination with the residue differences affecting thermo- and/or solvent stability. Thus, in some embodiments, the nitrilase amino acid sequence can include in addition to the residue differences affecting thermo- and/or solvent stability, residue differences at the residue positions above affecting enzymatic activity.

In some embodiments, the nitrilase polypeptides polypeptide with improved activity comprises an amino acid sequence includes at least one or more residue differences as compared to SEQ ID NO:2 at residue positions selected from: X30, X54, X73, X132, X199, and X293. In some embodiments, the amino acid residue at the residue positions is selected from the following: X30 is L; X54 is M, V, A, F, or Y; X132 is H, M, L or F; X199 is A, F, M, or C; and X293 is T or V.

In some embodiments, the nitrilase polypeptide comprises a fusion polypeptide, where the nitrilase polypeptide is fused or joined at its carboxy terminal end (C-terminal) to (a) a polypeptide of SEQ ID NO: 378 or 380 or (b) a polypeptide comprising at least a continuous segment of 17 amino acids of SEQ ID NO: 378 or 380.

In some embodiments, the nitrilase polypeptides with improved stability and/or improved activity comprises an amino acid sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, and 372.

The disclosure further provides nitrilase polypeptides capable of converting specific nitrile substrates to the corresponding carboxylic acids, and where appropriate, the corresponding amides with at least 1.1 fold the activity relative to the activity of SEQ ID NO:2 for the specific substrates. In some embodiments, nitrilase polypeptides are capable of converting the substrate of formula Ia to the product of formula IIa:

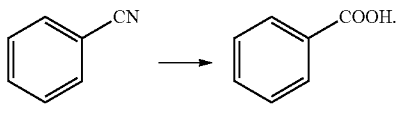

(Ia) (IIa)

with at least 1.1 fold the activity relative to the activity of SEQ ID NO:2. In some embodiments, the nitrilase polypeptide capable of converting substrate Ia to product IIa comprises an amino acid sequence selected from SEQ ID NO: 4, 8, 10, 12, 14, 16, 18, 22, 30, 32, 34, 36, 38, 40, 42, 44, 46, 50, 52, 54, 56, 144, 150, 152, 156, 158, 160, 162, 166, 168, 170, 172, 174, 176, 206, 208, 216, and 218.

In some embodiments, nitrilase polypeptides are capable of converting the substrate of formula Ib to the product of formula IIb:

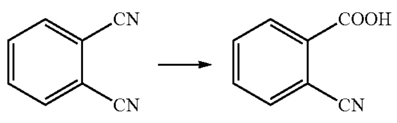

(Ib) (IIb)

with at least 1.1 fold the activity relative to the activity of SEQ ID NO:2. In some embodiments, the nitrilase polypeptide capable of converting substrate Ib to product IIb comprises an amino acid sequence selected from SEQ ID NO: 4, 8, 10, 12, 14, 16, 18, 22, 30, 32, 34, 36, 38, 40, 42, 44, 46, 50, 52, 54, 56, 144, 150, 152, 156, 158, 160, 162, 166, 168, 170, 172, 174, 176, 206, 208, 216, and 218.

In some embodiments, nitrilase polypeptides are capable of converting the substrate of formula Ic to the products of formula IIc' and/or IIc":

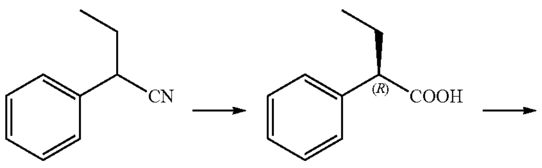

(Ic) (IIc')

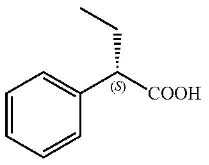

(IIc")

with at least 1.1 fold the activity relative to the activity of SEQ ID NO:2. In some embodiments, the nitrilase polypeptide capable of converting substrate Ic to products IIc' and/or IIc' comprises an amino acid sequence selected from SEQ ID NO: 4, 8, 10, 12, 14, 16, 18, 22, 30, 32, 34, 36, 38, 40, 42, 44, 46, 50, 52, 54, 56, 144, 150, 152, 156, 158, 160, 162, 166, 168, 170, 172, 174, 176, 206, 208, 216, and 218.

In some embodiments, the nitrilases polypeptide is capable of converting substrate Ic to IIc' in enantiomeric excess of product IIc". In some embodiments, the nitrilase polypeptide capable converting substrate Ic to product IIc' in enantiomeric excess comprises an amino acid sequence that has one or more residue differences as compared to SEQ ID NO:2 selected from: X54 is A; X139 is W; X163 is W; X171 is R; X197 is L or N; X199 is A; X203 is A; X267 is A; and X269 is P.

In some embodiments, the nitrilase polypeptide is capable of converting substrate Ic to product IIc" in enantiomeric excess of IIc'. In some embodiments, the nitrilase polypeptide capable converting substrate Ic to product IIc" in enantiomeric excess comprises an amino acid sequence that has one or more residue differences as compared to SEQ ID NO:2 selected from: X54 is F or M; X132 is H, M, or L; X163 is G, and X293 is T.

In some embodiments, nitrilase polypeptides are capable of converting the substrate of formula Id to the products of formula IId' and/or IId":

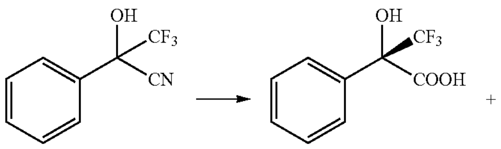

(Id) (IId')

-continued

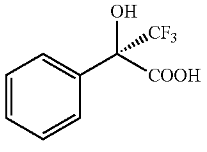

(IId″)

with at least 1.1 fold the activity relative to the activity of SEQ ID NO:2. In some embodiments, the nitrilase polypeptide capable of converting substrate Id to products IId' and/or IId" comprises an amino acid sequence selected from SEQ ID NO: 4, 10, 14, 21, 28, 180, 184, 188, 192, 194, 196, 200, 210, 220, 222, 226, 230, 238, 266, 304, 310, and 314.

In some embodiments, the nitrilase polypeptides are capable of converting substrate Id to product IId' in enantiomeric excess of IId". In some embodiments, the nitrilase polypeptide capable converting substrate Id to product IId' in enantiomeric excess comprises an amino acid sequence that has one or more residue differences as compared to SEQ ID NO:2 selected from: X132 is F, X163 is G, and X230 is Y.

In some embodiments, the nitrilase polypeptides are capable of converting the substrate of formula Ie to the product of formula IIe':

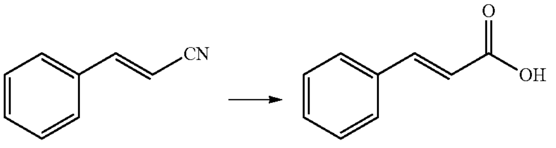

(Ie) (IIe′)

with at least 1.1 fold the activity relative to the activity of SEQ ID NO:2. In some embodiments, the nitrilase polypeptide capable of converting substrate Ie to product IIe' comprises an amino acid sequence selected from SEQ ID NO: 4, 8, 10, 12, 14, 22, 144, 146, 148, 150, 152, 154, 156, 158, 160, 162, 164, 166, 168, 170, 172, 174, 176, 180, 182, 186, 190, 206, 216, 220, 222, 224, 226, 228, 230, 232, 234, 236, 238, 240, 242, 244, 246, 248, 250, 266, 274, 278, 282, 284, 288, 290 and 296.

In some embodiments, the nitrilase polypeptides are capable of converting the substrate of formula Ie to the product of formula IIe' and IIe":

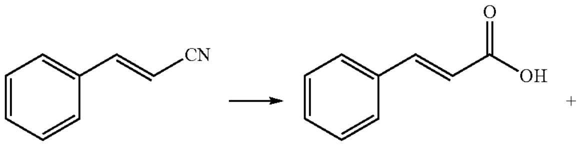

(Ie) (IIe′)

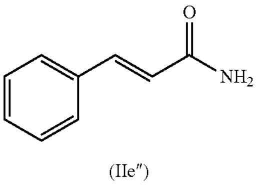

(IIe″)

with at least 1.1 fold the activity relative to the activity of SEQ ID NO:2. In some embodiments, the nitrilase polypeptide capable of converting substrate Ie to products IIe' and IIe"

comprises an amino acid sequence selected from SEQ ID NO: 22, 24, 28, 180, 186, 200, 216, 220, 226, 230, 232, 236, 238, 248, 250, 274, 278, 282, 284, 288, 290, 296, 302, 306, 316, and 318.

In some embodiments, the nitrilase polypeptides are capable of converting the substrate of formula If to the product of formula IIf:

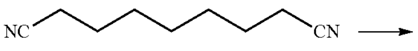

(If)

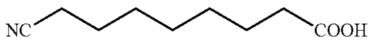

(IIf)

with at least 1.1 fold the activity relative to the activity of SEQ ID NO:2. In some embodiments, the nitrilase polypeptide capable of converting substrate If to product IIf comprises an amino acid sequence selected from SEQ ID NO: 32, 36, 40, 44, 52, and 154.

In some embodiments, the nitrilase polypeptides are capable of converting the substrate of formula Ig to the product of formula IIg:

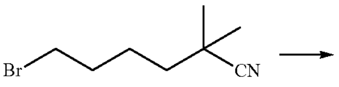

(Ig)

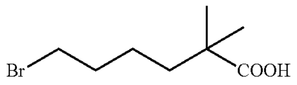

(IIg)

with at least 1.1 fold the activity relative to the activity of SEQ ID NO:2. In some embodiments, the nitrilase polypeptide capable of converting substrate Ig to product IIg comprises an amino acid sequence selected from SEQ ID NO: 4, 14, 22, 28, 180, 184, 188, 192, 194, 196, 200, 210, 220, 222, 226, 230, 238, 266, 304, 310 and 314.

In some embodiments, the nitrilase polypeptides are capable of converting the substrate of formula Ih to the product of formula IIh:

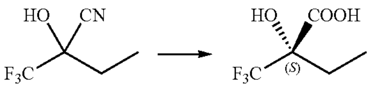

(Ih) (IIh)

with at least 1.1 fold the activity relative to the activity of SEQ ID NO:2. In some embodiments, the nitrilase polypeptide capable of converting substrate Ih to product IIh comprises an amino acid sequence selected from SEQ ID NO: 322, 324, 326, 342, 328, 330, 332, 334, 336, 344, 346, 338, 348, 350, 340, 352, 354 and 356.

In some embodiments, the nitrilase polypeptides are capable of converting the substrate of formula II to the product of formula IIi:

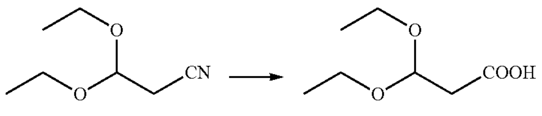

(Ii) (IIi)

with at least 1.1 fold the activity relative to the activity of SEQ ID NO:2. In some embodiments, the nitrilase polypeptide capable of converting substrate Ii to product IIi comprises an amino acid sequence selected from SEQ ID NO: 180, 220, 226, 228, 230, 232, 234, 236, 238, 240, 242, 244, 246, 248, 266, 274, 278, 282, and 284.

In some embodiments, the process comprises contacting the substrate Ij:

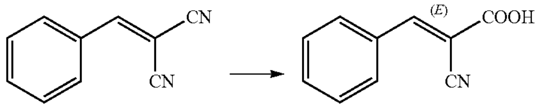

(Ij) (IIj)

with an engineered nitrilase described herein under suitable reaction conditions to convert the substrate to the product IIj.

In some embodiments, the process for converting the substrate of formula Ij to the product of formula IIj can use a nitrilase polypeptide comprising an amino acid sequence selected from SEQ ID NO: 46, 50, 52, 56 and 60.

In some embodiments, the nitrilase polypeptides are capable of converting the substrate of formula Ik to the product of formula IIk' and IIk":

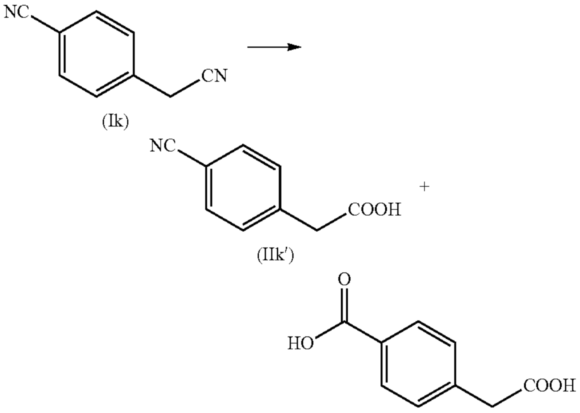

(Ik) (IIk') (IIk")

with at least 1.1 fold the activity relative to the activity of SEQ ID NO:2. In some embodiments, the nitrilase polypeptide capable of converting substrate Ik to products IIk' and IIk" comprises an amino acid sequence selected from SEQ ID NO: 30, 36, 46 or 56.

In other aspects, the present disclosure provides polynucleotides encoding the nitrilase polypeptides, expression vectors of the polynucleotides, host cells comprising the polynucleotides and expression vectors, and methods of preparing the nitrilase polypeptides by culturing the host cells and recovering the polypeptide from the host cells or the culture medium.

In another aspect, the nitrilase polypeptides described herein can be used in various processes for the conversion of a nitrile to the corresponding carboxylic acid, and where appropriate, the corresponding amide. Accordingly, in some embodiments, the nitrilase polypeptides can be used in a process for converting the substrate compound of formula I to the product of formula II:

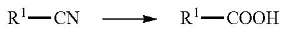

(I) (II)

wherein $R^1$ is a substituted or unsubstituted phenyl; a substituted or unsubstituted phenylalkyl($C_1$-$C_3$); a substituted or unsubstituted alkyl($C_3$-$C_8$) or a substituted or unsubstituted heteroalkyl (3-8 atoms), the process comprising contacting the substrate for formula I with an engineered nitrilase polypeptide described herein under suitable reaction conditions to convert the substrate to the product of formula II.

In some embodiments, the nitrilase polypeptides can be used in any of the specific substrates describes herein. These processes can comprise contacting a specific substrate selected from Ia to Ik with a nitrilase polypeptide described herein under suitable reactions conditions to convert the substrate to the corresponding products, i.e., IIa to IIk.

Further provided herein are kits comprising the engineered nitrilase polypeptides. The kits can comprise a single nitrilase polypeptide or a plurality of polypeptides for testing on various nitrilase substrates. In some embodiments, where a plurality of nitrilase polypeptides are present, the polypeptides can be in arrays. In some embodiments, the kits can contain reagents, solvents, test substrates, and/or dispensers for using the nitrilase polypeptides.

5. DETAILED DESCRIPTION

The present disclosure provides nitrilase polypeptides, polynucleotides and uses therefore. These engineered polypeptides have improved performance characteristics that include, among others, thermostability, solvent stability, substrate recognition, and enzymatic activity. For the descriptions herein and the appended claims, the singular forms “a”, “an” and “the” include plural referents unless the context clearly indicates otherwise. Thus, for example, reference to “a protein” includes more than one protein, and reference to “a compound” refers to more than one compound.

Also, the use of “or” means “and/or” unless stated otherwise. Similarly, “comprise,” “comprises,” “comprising” “include,” “includes,” and “including” are interchangeable and not intended to be limiting.

It is to be further understood that where descriptions of various embodiments use the term “comprising,” those skilled in the art would understand that in some specific instances, an embodiment can be alternatively described using language “consisting essentially of” or “consisting of.”

It is to be understood that both the foregoing general description, including the drawings, and the following detailed description are exemplary and explanatory only and are not restrictive of this disclosure.

5.1 Abbreviations

For the purposes of the descriptions herein, the abbreviations used for the genetically encoded amino acids are conventional and are as follows:

| Amino Acid | Three-Letter | One-Letter |
|---|---|---|
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

When the three-letter abbreviations are used, unless specifically preceded by an "L" or a "D" or clear from the context in which the abbreviation is used, the amino acid may be in either the L- or D-configuration about α-carbon (Cα). For example, whereas "Ala" designates alanine without specifying the configuration about the α carbon, "D-Ala" and "L-Ala" designate D-alanine and L-alanine, respectively. When the one-letter abbreviations are used, upper case letters designate amino acids in the L-configuration about the -carbon and lower case letters designate amino acids in the D-configuration about the α-carbon. For example, "A" designates L-alanine and "a" designates D-alanine. When peptide sequences are presented as a string of one-letter or three-letter abbreviations (or mixtures thereof), the sequences are presented in the N→C direction in accordance with common convention.

5.2 Definitions

The technical and scientific terms used in the descriptions herein will have the meanings commonly understood by one of ordinary skill in the art, unless specifically defined otherwise. Accordingly, the following terms are intended to have the following meanings.

"Nitrilase" refers to a polypeptide having an enzymatic capability of hydrolyzing nitriles into their corresponding carboxylic acids and ammonia. In some embodiments, nitrilases are also capable of producing the corresponding amide.

"Alkyl" by itself or as part of another substituent refers to a saturated or unsaturated branched, straight-chain or cyclic monovalent hydrocarbon radical having the stated number of carbon atoms (i.e., $C_1$-$C_6$ means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. The expression "lower alkyl" refers to alkyl groups composed of from 1 to 4 carbon atoms. In some embodiments, the alkyl groups are $C_1$-$C_3$ alkyl. In some embodiments, the alkyl groups are $C_3$-$C_8$ alkyl.

"Alkanyl" by itself or as part of another substituent refers to a saturated branched, straight-chain or cyclic alkyl derived by the removal of one hydrogen atom from a single carbon atom of a parent alkane. Alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In some embodiments, the alkanyl groups are ($C_1$-$C_3$) alkanyl. In some embodiments, the alkanyl groups are ($C_3$-$C_8$) alkanyl.

"Alkenyl" by itself or as part of another substituent refers to an unsaturated branched, straight chain or cyclic alkyl having at least one carbon carbon double bond derived by the removal of one hydrogen atom from a single carbon atom of a parent alkene. The group may be in either the cis or trans conformation about the double bond(s). Alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In some embodiments, the alkenyl group is ($C_2$-$C_6$) alkenyl.

"Alkynyl" by itself or as part of another substituent refers to an unsaturated branched, straight chain or cyclic alkyl having at least one carbon carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In some embodiments, the alkynyl group is ($C_2$-$C_6$) alkynyl.

"Cycloalkyl" and "Heterocycloalkyl" by themselves or as part of another substituent refer to cyclic versions of "alkyl" and "heteroalkyl" groups, respectively. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

"Heteroalkyl," "Heteroalkanyl," "Heteroalkenyl," or "Heteroalkynyl," by themselves or as part of another substituent refer to alkyl, alkanyl, alkenyl, alkynyl groups, respectively, in which one or more of the carbon atoms are each independently replaced with the same or different heteratoms or heteroatomic groups. Heteroatoms and/or heteroatomic groups which can replace the carbon atoms include, but are not limited to, —O—, —S—, —S—O—, —NR'—, —PH—, —S(O)—, —$S(O)_2$—, —S(O)NR'—, —$S(O)_2$NR'—, and the like, including combinations thereof, where each R' is independently hydrogen or ($C_1$-$C_6$) alkyl.

"Aryl" by itself or as part of another substituent refers to a monovalent aromatic hydrocarbon group having the stated number of carbon atoms (i.e., $C_5$-$C_{15}$ means from 5 to 15 carbon atoms) derived by the removal of one hydrogen atom from a single carbon atom of a parent aromatic ring system. Aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as indacene, s indacene, indane, indene, naphthalene, octacene, octaphene, octalene, ovalene, penta 2,4 diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In some embodiments, the aryl group is ($C_5$-$C_{15}$) aryl, with ($C_5$-$C_{10}$) being preferred. In some embodiments, the aryls are cyclopentadienyl, phenyl and naphthyl.

"Heteroaryl" by itself or as part of another substituent refers to a monovalent heteroaromatic group having the stated number of ring atoms (e.g., "5 14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrone, benzothiadiazole, benzothiazole, benzotriazole, benzoxazine, benzoxazole, benzoxazoline, carbazole, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof. In some embodiments, the heteroaryl group is a 5 14 membered heteroaryl. In some embodiments, the heteroaryl group is a 5 10 membered heteroaryl.

"Substituted Alkyl, Aryl, Arylalkyl, Heteroaryl or Heteroarylalkyl" refers to an alkyl, aryl, arylalkyl, heteroaryl or heteroarylakyl group in which one or more hydrogen atoms is replaced with another substituent group. Exemplary substituent groups include, but are not limited to, —OR', —SR', —NR'R', —$NO_2$, —NO, —CN, —$CF_3$, halogen (e.g., —F, —Cl, —Br and —I), —C(O)R', —C(O)OR', —C(O)NR', —$S(O)_2$R', —$S(O)_2$NR'R', where each R' is independently selected from the group consisting of hydrogen and ($C_1$-$C_6$) alkyl.

"Amino" by itself or as part of another substituent refers to the group —$NH_2$. Substituted amino refers to the group —NHR', NR'R' and NR'R'R', where each R' is independently selected from substituted or unsubstituted alkyl, cycloalkyl, cycloheteroalkyl, alkoxy, aryl, heteroaryl, heteroarylalkyl, acyl, alkoxycarbonyl, sulfanyl, sulfinyl, sulfonyl, and the like. Typical amino groups include, but are limited to, dimethylamino, diethylamino, trimethylamino, triethylamino, methylysulfonylamino, furanyl-oxy-sulfamino, and the like.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes 1-fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

"Protein", "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Polynucleotide" or "nucleic Acid" refers to two or more nucleosides that are covalently linked together. The polynucleotide may be wholly comprised ribonucleosides (i.e., an RNA), wholly comprised of 2' deoxyribonucleotides (i.e., a DNA) or mixtures of ribo- and 2' deoxyribonucleosides. While the nucleosides will typically be linked together via standard phosphodiester linkages, the polynucleotides may include one or more non-standard linkages. Non-limiting example of such non-standard linkages include phosphoramidates (Beaucage et al., 1993, Tetrahedron 49:1925; Letsinger, 1970, Nucl. Acids. Res. 14:3487; Sawai et al, 1984, Chem Lett N5:805-808; Letsinger et al., 1988, J. Am. Chem. Soc. 110:4470; Pauwels et al., 1986, Chemica Scripta 26:141), phosphorothioates (Mag et al., 1991, Nucl. Acids. Res. 19:1437; U.S. Pat. No. 5,644,048), phosphorothioates (Briu et al., 1989, J. Am. Chem. Soc. 111:2321), O-methylphosphodiesters (Eckstein, 1991, Oligonucleotides and Analogues: A Practical Approach, Oxford University Press), amides (Egholm, 1992, J. Am. Chem. Soc. 114:1895; Meier et al., 1992, Chem. Rut. Ed. Engl. 31:1008; Nielson, 1993, Nature 365:366; Carlsson et al., 1996, Nature 380:207 WO 94/25477; WO 92/20702; U.S. Pat. Nos. 6,107,470; 5,786,461; 5,773,571; 5,719,262; and 5,539,082), positively-charged linkages (Denocy et al., 1995, Proc. Natl. Acad. Sci. USA 92:6097 and non-ionic linkages (U.S. Pat. No. 5,386,023; U.S. Pat. No. 5,637,684; U.S. Pat. No. 5,602,240; U.S. Pat. No. 5,216,141; and U.S. Pat. No. 4,469,863); Kiedrowski et al., 1991, Angew. Chem. Intl. Ed. English 30:423; Letsinger et al. 1988, J. Am. Chem. Soc. 110:4470; and Letsinger et al. 1994, Nucleosides & Nucleotides 13:1597).

"Coding sequence" refers to that portion of a nucleic acid (e.g., a gene) that encodes an amino acid sequence of a protein.

"Naturally occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Recombinant" or "engineered" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Fusion construct" refers to a nucleic acid comprising the coding sequence for first polypeptide and the coding sequence (with or without introns) for a second polypeptide in which the coding sequences are adjacent and in the same reading frame such that, when the fusion construct is transcribed and translated in a host cell, a polypeptide is produced in which the C-terminus of the first polypeptide is joined to the N-terminus of the second polypeptide. A "fusion polypeptide" refers to the polypeptide product of the fusion construct.

"Fused," "Joined" as used herein refers to linkage of heterologous amino acid or polynucleotide sequences. Thus, "fused" refers to any method known in the art for functionally connecting polypeptide and/or polynucleotide domains, including but not limited to recombinant fusion with or without intervening linking sequence, non-covalent association, and covalent bonding.

"Percentage of sequence identity," "percent identity," and "percent identical" are used herein to refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence identity is performed using the BLAST and BLAST 2.0 algorithms (see e.g., Altschul et al., 1990, J. Mol. Biol. 215: 403-410 and Altschul et al., 1977, Nucleic Acids Res. 3389-3402). Software for performing BLAST analyses is publicly available through the National Center for Biotechnology Information website.

Briefly, the BLAST analyses involve first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, Proc Natl Acad Sci USA 89:10915).

Numerous other algorithms are available that function similarly to BLAST in providing percent identity for two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Additionally, determination of sequence alignment and percent sequence identity can employ the BESTFIT or GAP programs in the GCG Wisconsin Software package (Accelrys, Madison Wis.), using default parameters provided.

"Reference sequence" refers to a defined sequence to which an altered sequence is compared. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a comparison window to identify and compare local regions of sequence similarity.

The term "reference sequence" is not intended to be limited to wild-type sequences, and can include engineered or altered sequences. For example, in some embodiments, a "reference sequence" can be a previously engineered or altered amino acid sequence. For instance, a "reference sequence based on SEQ ID NO:2 having an arginine residue at position X91" refers to a reference sequence corresponding to SEQ ID NO:2 with a arginine residue at X91 (the un-altered version of SEQ ID NO:2 has alanine at X91).

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Substantial identity" refers to a polynucleotide or polypeptide sequence that has at least 80 percent sequence identity, at least 85 percent sequence identity, at least 89 percent sequence identity, at least 95 percent sequence identity, and even at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). Preferably, residue positions which are not identical differ by conservative amino acid substitutions.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered nitrilase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Stereospecificity" refers to the preferential conversion in a chemical or enzymatic reaction of one stereoisomer over another. Stereospecificity can be partial, where the conversion of one stereoisomer is favored over the other, or it may be complete where only one stereoisomer is converted.

"Improved enzyme property" refers to any enzyme property made better or more desirable for a particular purpose as compared to that property found in a reference enzyme. For the engineered nitrilase polypeptides described herein, the comparison is generally made to the wild-type nitrilase enzyme, although in some embodiments, the reference nitrilase can be another improved engineered nitrilase. Enzyme properties for which improvement can be made include, but are not limited to, enzymatic activity (which can be expressed in terms of percent conversion of the substrate in a period of time), thermal stability, solvent stability, pH activity profile, coenzyme requirements, refractoriness to inhibitors (e.g., product inhibition), stereospecificity, and stereoselectivity (including enantioselectivity).

"Increased enzymatic activity" or "increased activity" refers to an improved property of an engineered enzyme, which can be represented by an increase in specific activity (e.g., product produced/time/weight protein) or an increase in percent conversion of the substrate to the product (e.g., percent conversion of starting amount of substrate to product in a specified time period using a specified amount of nitrilase) as compared to a reference enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.1 fold, 1.5 fold the enzymatic activity of the corresponding wild-type or engineered enzyme, to as much as 2 fold, 5 fold, 10 fold, 20 fold, 25 fold, or 50 fold, or more enzymatic activity than the naturally occurring enzyme (e.g., a nitrilase) or another engineered enzyme from which the enzymes exhibiting increased activity were derived. In specific embodiments, the engineered nitrilase enzymes of the present disclosure exhibit improved enzymatic activity in the range of 1.5 to 50 fold, 1.5 to 100 fold or greater than that of the parent nitrilase enzyme (i.e., the wild-type or engineered nitrilase from which they were derived). It is understood by the skilled artisan that the activity of any enzyme is diffusion limited such that the catalytic turnover rate cannot exceed the diffusion rate of the substrate, including any required coenzymes. The theoretical maximum of the diffusion limit is generally about $10^8$ to $10^9$ ($M^{-1}$ $s^{-1}$). Hence, any improvements in the enzyme activity of the nitrilase will have an upper limit related to the diffusion rate of the substrates acted on by the nitrilase enzyme. Nitrilase activity can be measured by any one of standard assays used for measuring nitrilases, such as change in substrate or product concentration, or change in concentration of the amino group donor. Comparisons of enzyme activities are made using a defined preparation of enzyme, a defined assay under a set condition, and one or more defined substrates, as further described in detail herein. Generally, when enzymes in cell lysates are compared, the numbers of cells and the amount of protein assayed are determined as well as use of identical expression systems and identical host cells to minimize variations in amount of enzyme produced by the host cells and present in the lysates.

"Conversion" refers to the enzymatic transformation of a substrate to the corresponding product. "Percent conversion" refers to the percent of the substrate that is converted to the product within a period of time under specified conditions. Thus, for example, the "enzymatic activity" or "activity" of a nitrilase polypeptide can be expressed as "percent conversion" of the substrate to the product.

"Thermostable" or "thermal stable" are used interchangeably to refer to a polypeptide that is resistant to inactivation when exposed to a set of temperature conditions (e.g., 40-80° C.) for a period of time (e.g., 0.5-24 hrs) compared to the untreated enzyme, thus retaining a certain level of residual activity (more than 60% to 80% for example) after exposure to elevated temperatures.

"Solvent stable" refers to a polypeptide that maintains similar activity (more than e.g., 60% to 80%) after exposure to varying concentrations (e.g., 5-99%) of solvent, (e.g., methyl alcohol, isopropyl alcohol, dimethylsulfoxide, tetrahydrofuran, 2-methyltetrahydrofuran, acetone, toluene, butylacetate, methyl tert-butylether, acetonitrile, etc.) for a period of time (e.g., 0.5-24 hrs) compared to the untreated enzyme.

"Thermo- and solvent stable" refers to a polypeptide that is both thermostable and solvent stable.

"Derived from" as used herein in the context of engineered enzymes identifies the originating enzyme, and/or the gene encoding such enzyme, upon which the engineering was based. For example, the engineered nitrilase enzyme of SEQ ID NO: 4 was obtained by mutating the naturally occurring nitrilase of SEQ ID NO:2. Thus, this engineered nitrilase enzyme of SEQ ID NO:4 is "derived from" the wild-type polypeptide of SEQ ID NO:2

"Amino acid" or "residue" as used in context of the polypeptides disclosed herein refers to the specific monomer at a sequence position (e.g., P8 indicates that the "amino acid" or "residue" at position 8 of SEQ ID NO: 2 is a proline.)

"Hydrophilic amino acid or residue" refers to an amino acid or residue having a side chain exhibiting a hydrophobicity of less than zero according to the normalized consensus hydrophobicity scale of Eisenberg et al., 1984, J. Mol. Biol. 179:125-142. Genetically encoded hydrophilic amino acids include L-Thr (T), L-Ser (S), L-His (H), L-Glu (E), L-Asn (N), L-Gln (O), L-Asp (D), L-Lys (K) and L-Arg (R).

"Acidic amino acid or residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include L-Glu (E) and L-Asp (D).

"Basic amino acid or residue" refers to a hydrophilic amino acid or residue having a side chain exhibiting a pKa value of greater than about 6 when the amino acid is included in a peptide or polypeptide. Basic amino acids typically have positively charged side chains at physiological pH due to association with hydronium ion. Genetically encoded basic amino acids include L-Arg (R) and L-Lys (K).

"Polar amino acid or residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (O), L-Ser (S) and L-Thr (T).

"Hydrophobic amino acid or residue" refers to an amino acid or residue having a side chain exhibiting a hydrophobicity of greater than zero according to the normalized consensus hydrophobicity scale of Eisenberg et al., 1984, J. Mol. Biol. 179:125-142. Genetically encoded hydrophobic amino acids include L-Pro (P), L-Ile (I), L-Phe (F), L-Val (V), L-Leu (L), L-Trp (W), L-Met (M), L-Ala (A) and L-Tyr (Y).

"Aromatic amino acid or residue" refers to a hydrophilic or hydrophobic amino acid or residue having a side chain that includes at least one aromatic or heteroaromatic ring. Genetically encoded aromatic amino acids include L-Phe (F), L-Tyr (Y) and L-Trp (W). Although owing to the pKa of its heteroaromatic nitrogen atom L-His (H) it is sometimes classified as a basic residue, or as an aromatic residue as its side chain includes a heteroaromatic ring, herein histidine is classified as a hydrophilic residue or as a "constrained residue" (see below).

"Constrained amino acid or residue" refers to an amino acid or residue that has a constrained geometry. Herein, constrained residues include L-Pro (P) and L-His (H). Histidine has a constrained geometry because it has a relatively small imidazole ring. Proline has a constrained geometry because it also has a five membered ring.

"Non-polar amino acid or residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L-Gly (G), L-Leu (L), L-Val (V), L-Ile (I), L-Met (M) and L-Ala (A).

"Aliphatic amino acid or residue" refers to a hydrophobic amino acid or residue having an aliphatic hydrocarbon side chain. Genetically encoded aliphatic amino acids include L-Ala (A), L-Val (V), L-Leu (L) and L-Ile (I).

"Cysteine" or L-Cys (C) is unusual in that it can form disulfide bridges with other L-Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L-Cys (C) (and other amino acids with —SH containing side chains) to exist in a peptide in either the reduced free —SH or oxidized disulfide-bridged form affects whether L-Cys (C) contributes net hydrophobic or hydrophilic character to a peptide. While L-Cys (C) exhibits a hydrophobicity of 0.29 according to the normalized consensus scale of Eisenberg (Eisenberg et al., 1984, supra), it is to be understood that for purposes of the present disclosure L-Cys (C) is categorized into its own unique group.

"Small amino acid or residue" refers to an amino acid or residue having a side chain that is composed of a total of three or fewer carbon and/or heteroatoms (excluding the α-carbon and hydrogens). The small amino acids or residues may be further categorized as aliphatic, non-polar, polar or acidic small amino acids or residues, in accordance with the above definitions. Genetically-encoded small amino acids include L-Ala (A), L-Val (V), L-Cys (C), L-Asn (N), L-Ser (S), L-Thr (T) and L-Asp (D).

"Hydroxyl-containing amino acid or residue" refers to an amino acid containing a hydroxyl (—OH) moiety. Genetically-encoded hydroxyl-containing amino acids include L-Ser (S) L-Thr (T) and L-Tyr (Y).

"Amino acid difference" or "residue difference" refers to a change in the residue at a specified position of a polypeptide sequence when compared to a reference sequence. For example, a residue difference at position X91, where the reference sequence has an alanine, refers to a change of the residue at position X91 to any residue other than alanine. As disclosed herein, an enzyme can include one or more residue differences relative to a reference sequence, where multiple residue differences typically are indicated by a list of the specified positions where changes are made relative to the reference sequence (e.g., "one or more residue differences as compared to SEQ ID NO:2 at the following residue positions: X23, X30, X37, X40, X49, X54, X55, X65, X73, X85, X121, X130, X132, X134, X139, X152, X161, X163, X170, X171, X172, X173, X191, X197, X199, X200, X201, X203, X209, X217, X225, X230, X233, X240, X267, X269, X272, X282, X288, X289, X293, X295, X297, X303, X317, X319, X323, X327, X330, X332, and X334.").

"Conservative" amino acid substitutions, mutations ore residue difference refer to the interchangeability of residues having similar side chains, and thus typically involves substitution of the amino acid in the polypeptide with amino acids within the same or similar defined class of amino acids. However, as used herein, in some embodiments, conservative mutations do not include substitutions from a hydrophilic to hydrophilic, hydrophobic to hydrophobic, hydroxyl-containing to hydroxyl-containing, or small to small residue, if the conservative mutation can instead be a substitution from an aliphatic to an aliphatic, non-polar to non-polar, polar to polar, acidic to acidic, basic to basic, aromatic to aromatic, or constrained to constrained residue. Further, as used herein, A, V, L, or I can be conservatively mutated to either another aliphatic residue or to another non-polar residue. Table 1 below shows exemplary conservative substitutions.

TABLE 1

| Residue | Possible Conservative Substitutions |
|---|---|
| A, L, V, I | Other aliphatic (A, L, V, I) |
| | Other non-polar (A, L, V, I, G, M) |
| G, M | Other non-polar (A, L, V, I, G, M) |
| D, E | Other acidic (D, E) |
| K, R | Other basic (K, R) |
| P, H | Other constrained (P, H) |
| N, Q, S, T | Other polar |
| Y, W, F | Other aromatic (Y, W, F) |
| C | None |

"Non-conservative substitution", "non-conservative residue difference" or "non-conservative mutation" refers to substitution of an amino acid in the polypeptide with an amino acid with significantly differing side chain properties. Non-conservative substitutions may use amino acids between, rather than within, the defined groups listed above. In one embodiment, a non-conservative mutation affects (a) the structure of the peptide backbone in the area of the substitution (e.g., proline for glycine) (b) the charge or hydrophobicity, or (c) the bulk of the side chain.

"Deletion" refers to modification of the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, up to 20% of the total number of amino acids, or up to 30% of the total number of amino acids making up the polypeptide while retaining enzymatic activity and/or retaining the improved properties of an engineered nitrilase enzyme. Deletions can be directed to the internal portions and/or terminal portions of the polypeptide. In various embodiments, the deletion can comprise a continuous segment or can be discontinuous.

"Insertion" refers to modification of the polypeptide by addition of one or more amino acids to the reference polypeptide. In some embodiments, the improved engineered nitrilase enzymes comprise insertions of one or more amino acids to the naturally occurring nitrilase polypeptide as well as insertions of one or more amino acids to other improved nitrilase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Fragment" as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of the full-length nitrilase polypeptide, for example the polypeptide of SEQ ID NO:4.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved nitrilase enzymes may be present within a cell, present in the cellular medium, or prepared in various forms, such as lysates or isolated preparations. As such, in some embodiments, the improved nitrilase enzyme can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure nitrilase composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated improved nitrilases polypeptide is a substantially pure polypeptide composition.

"Stringent hybridization" is used herein to refer to conditions under which nucleic acid hybrids are stable. As known to those of skill in the art, the stability of hybrids is reflected in the melting temperature ($T_m$) of the hybrids. In general, the stability of a hybrid is a function of ion strength, temperature, G/C content, and the presence of chaotropic agents. The $T_m$ values for polynucleotides can be calculated using known methods for predicting melting temperatures (see, e.g., Baldino et al., Methods Enzymology 168:761-777; Bolton et al., 1962, Proc. Natl. Acad. Sci. USA 48:1390; Bresslauer et al., 1986, Proc. Natl. Acad. Sci. USA 83:8893-8897; Freier et al., 1986, Proc. Natl. Acad. Sci. USA 83:9373-9377; Kierzek et al., Biochemistry 25:7840-7846; Rychlik et al., 1990, Nucleic Acids Res 18:6409-6412 (erratum, 1991, Nucleic Acids Res 19:698); Sambrook et al., supra); Suggs et al., 1981, In Developmental Biology Using Purified Genes (Brown et al., eds.), pp. 683-693, Academic Press; and Wetmur, 1991, Crit Rev Biochem Mol Biol 26:227-259. All publications incorporate herein by reference). In some embodiments, the polynucleotide encodes the polypeptide disclosed herein and hybridizes under defined conditions, such as moderately stringent or highly stringent conditions, to the complement of a sequence encoding an engineered nitrilase enzyme of the present disclosure.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA; with greater than about 90% identity to target-polynucleotide. Exemplary moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5×Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the nitrilases enzymes may be codon optimized for optimal production from the host organism selected for expression.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Control sequence" is defined herein to include all components, which are necessary or advantageous for the expression of a polynucleotide and/or polypeptide of the present disclosure. Each control sequence may be native or foreign to the polynucleotide of interest. Such control sequences include, but are not limited to, a leader, polyadenylation sequence, propeptide sequence, promoter, signal peptide sequence, and transcription terminator.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Promoter sequence" is a nucleic acid sequence that is recognized by a host cell for expression of a polynucleotide of interest, such as a coding sequence. The control sequence may comprise an appropriate promoter sequence. The promoter sequence contains transcriptional control sequences, which mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

5.3 Detailed Description of Embodiments

Nitrilase enzymes catalyse the conversion of nitriles to corresponding carboxylic acids and ammonia. The enzymes can act on aromatic (e.g., benzonitrile) and aliphatic nitriles, (e.g., aliphatic mononitriles and dinitriles, e.g., fumarodinitrile, succinodinitrile, adipodinitrile, 3-hexenoic acid dinitrile, octanoic acid dinitrile, or decanoic acid dinitrile). Nitrilases can also stereospecifically convert chiral nitriles to their corresponding chiral acids and ammonia. While nitrilases can carryout the reaction under mild conditions, many of the substrates for nitrilases can require use of organic solvents to increase the availability of hydrophobic substrates to the enzyme. In addition, commercial applications of nitrilases can require extended incubation times under harsh conditions, such as elevated temperatures.

In the embodiments herein, nitrilase enzymes have been engineered to have improved properties as compared to the naturally occurring nitrilase enzyme, and in some embodiments, to other engineered nitrilase enzymes. In some embodiments, the improved property (as compared to wild-type or another engineered polypeptide) of the nitrilase polypeptide is with respect to its thermostability, solvent stability, enzymatic activity, and/or stereospecificity. In some embodiments, the nitrilase polypeptide has more than one improved property, such as a combination of thermostability, solvent stability, and enzymatic activity.

In some embodiments, these engineered nitrilase polypeptides comprise an amino acid sequence that has one or more residue differences as compared to a nitrilase reference sequence, e.g., SEQ ID NO:2. The residue differences can be non-conservative, conservative, or a combination of non-conservative and conservative amino acid residue differences. With respect to the residue differences and the descriptions of residue positions, the nitrilases provided herein can be described in reference to the amino acid sequence of the naturally occurring nitrilase of *Bradyrhizobium japonicum* USDA 110 (SEQ ID NO:2), or an engineered nitrilase, such as the polypeptide of SEQ ID NO:6. For the descriptions herein, the amino acid residue position in the reference sequence is determined in the nitrilase polypeptide beginning from the initiating methionine (M) residue (i.e., M represents residue position 1), although it will be understood by the skilled artisan that this initiating methionine residue may be removed by biological processing machinery, such as in a host cell or in vitro translation system, to generate a mature protein lacking the initiating methionine residue.

The polypeptide amino acid sequence position at which a particular amino acid or amino acid change ("residue difference") is present is sometimes described herein as "Xn", or "position n", where n refers to the residue position with respect to the reference sequence.

In some embodiments, the nitrilase polypeptide can be described in reference to a specific substitution mutation, which is a replacement of the specific residue in a reference sequence with a different specified residue may be denoted by the conventional notation "X(number)Y", where X is the single letter identifier of the residue in the reference sequence, "number" is the residue position in the reference sequence, and Y is the single letter identifier of the residue substitution in the engineered sequence.

In the embodiments herein, the engineered nitrilase polypeptides are capable of converting the substrate of formula (I) to the product of formula (II):

$$\underset{(I)}{R^1\text{—CN}} \longrightarrow \underset{(II)}{R^1\text{—COOH}}$$

wherein $R^1$ can be a substituted or unsubstituted aryl, substituted or unsubstituted heteroaryl, substituted or unsubstituted arylalkyl, substituted or unsubstituted heterarylalkyl, substituted or unsubstituted alkyl, or substituted or unsubstituted heteroalkyl. In particular, $R^1$ is a substituted or unsubstituted phenyl; a substituted or unsubstituted phenylalkyl($C_1$-$C_3$); a substituted or unsubstituted alkyl($C_3$-$C_8$) or a substituted or unsubstituted heteroalkyl (3-8 atoms). Specific substrates and corresponding products for which the activity of the nitrilase activity can be measured and compared, where appropriate, are further described in more detail below.

In some embodiments, the nitrilase polypeptide of the present disclosure has improved thermostability as compared to the polypeptide of SEQ ID NO:2 to a defined temperature condition, i.e., defined time at a defined temperature. An exemplary condition is 3 hrs at 40° C. In some embodiments, the nitrilase polypeptide herein has at least 1.1 fold, 1.5 fold, 2 fold, 3 fold, 4 fold, 5 fold, 6 fold, 7 fold, 8 fold, 10 fold, 15 fold, or 20 fold or more residual activity as compared to the residual activity of the naturally occurring nitrilase of SEQ ID NO:2 when they are treated to a defined temperature condition of 3 hrs at 40° C. In some embodiments, the nitrilase polypeptide has at least 5 fold improved thermostability as compared to SEQ ID NO:2 to the condition of 3 hrs at 40° C.

In some embodiments, the nitrilase polypeptide has improved solvent stability as compared to the solvent stability of the polypeptide of SEQ ID NO:2 to a defined solvent condition. The solvent stability can be measured by treating the polypeptide in a specific solvent for a defined period of time and determining the residual enzyme activity remaining following the treatment. Suitable solvents that can be used include, among others, methanol, isopropyl alcohol, dimethylsulfoxide, tetrahydrofuran, 2-methyltetrahydrofuran, acetone, toluene, butylacetate, methyl tert-butylether, and acetonitrile. An exemplary defined solvent condition is 3 hrs in 10% methanol. In some embodiments, the nitrilase polypeptide herein has at least 1.1 fold, 1.5 fold, 2 fold, 3 fold, 4 fold, 5 fold, 6 fold, 7 fold, 8 fold, 10 fold, 15 fold, or 20 fold or more residual activity as compared to the residual activity of the naturally occurring nitrilase of SEQ ID NO:2 when they are treated to the defined solvent condition of 3 hrs in 10% methanol. In some embodiments, the nitrilase polypeptide has at least 5 fold improved solvent stability as compared to SEQ ID NO:2 to the condition of 3 hrs in 10% methanol. As used herein, "residual activity" refers to the activity remaining after treatment at the specific condition.

While the properties of thermostability and solvent stability can be independent characteristics of the nitrilase polypeptide, in some embodiments, the polypeptide can have both thermo- and solvent-stability characteristics described above, as suggested by the observation that changes in amino acid residues at certain residue positions of the nitrilase amino acid sequence result in improvements in both thermo- and solvent-stability characteristics of the nitrilase enzyme.

In some embodiments, the nitrilase polypeptide has improved thermo- and/or solvent stability as compared to the reference polypeptide of SEQ ID NO:2 and comprises an amino acid sequence that is at least 80%, 85%, 86%, 87%, 88%, 89%, 90%, 91%, 92%, 93%, 94% 95%, 96%, 97%, 98%, or 99% or more identical to the sequence of the reference sequence of SEQ ID NO:2.

In some embodiments, the nitrilase polypeptide has improved thermo- and/or solvent stability as compared to the reference polypeptide of SEQ ID NO:2 and comprises an amino acid sequence that is at least 80%, 85%, 86%, 87%, 88%, 89%, 90%, 91%, 92%, 93%, 94% 95%, 96%, 97%, 98%, or 99% or more identical to the sequence of the reference sequence of another engineered nitrilase, in particular a reference sequence selected from SEQ ID NO: 6, 84, 122, 130, 138, 358, 360, or 362.

Specifically excluded from the scope of the present disclosure are the nitrilase polypeptides represented by SEQ ID NO: 374 and 376, and specific nitrilase polypeptides sequences disclosed in U.S. Pat. No. 7,521,216.

In some embodiments, the nitrilase polypeptides with improved thermo- and/or solvent stability comprises an amino acid sequence that has at least one or more residue differences as compared to SEQ ID NO:2 at residue positions selected from: X91; X108; X139; X166; X230; X266; and X309. As provided herein, the residue differences as compared to SEQ ID NO:2 at these specified positions are found to be associated with improvements in thermo- and/or solvent stability.

In some embodiments, the amino acid residue at the above residue positions are selected from: X91 is R or K; X108 is S, N or Q; X139 is W or F; X166 is F, W, Y or L; X230 is Y, F, W, V, L, A, or I; X266 is V, L, A or I; and X309 is V, L, A or I.

In some embodiments, the amino acid residue at the above residue positions are selected from: X91 is R; X108 is S; X139 is F; X166 is L; X230 is V; X266 is L; and X309 is L. In some embodiments, the nitrilase amino acid sequence has at least at residue position X91 an R. In some embodiments, the nitrilase amino acid sequence has at least at residue position X230 a V. In some embodiments, the nitrilase amino acid sequence has at least at residue position X309 an L.

In some embodiments, other residue differences as compared to SEQ ID NO:2 may be present in the engineered nitrilase polypeptide to improve its enzymatic activity as compared to the reference enzyme of SEQ ID NO:2, or a reference engineered nitrilase, such as SEQ ID NO:6. It is to be understood that these residue differences affecting enzymatic activity may be present independently of or in combination with the residue differences affecting thermo- and/or solvent stability of the enzyme. Accordingly, in some embodiments, the engineered nitrilase polypeptide has improved activity for converting the substrate of formula I to the product of formula II relative to the activity of SEQ ID NO:2. In some embodiments, the engineered nitrilase polypeptide has improved thermo- and/or solvent stability and further has improved activity for converting the substrate of formula I to the product of formula II relative to the activity of SEQ ID NO:2.

In some embodiments, the nitrilase polypeptide has at least 1.1 fold improved activity relative to the enzymatic activity of SEQ ID NO:2 for the same substrate under the same defined assay condition. In some embodiments, the nitrilase polypeptide has at least 1.2 fold, 1.3 fold 1.5 fold, 2 fold, 5 fold, 10 fold, 15 fold, 20 fold, 30 fold, 40 fold, or 50 fold or more improved activity relative to the enzymatic activity of SEQ ID NO:2 for the same substrate under the same defined assay condition. As will be apparent to the skilled artisan, the measurement of enzymatic activity is distinguished from measurements of stability to temperature or solvent as the former is determined without preincubation at the temperature or solvent condition used to measure stability.

In some embodiments, the nitrilase polypeptides with the improved activity for converting the substrate of formula I to the production of formula II relative to the activity of SEQ ID NO:2 comprises an amino acid sequence that has at least 80%, 85%, 86%, 87%, 88%, 89%, 90%, 91%, 92%, 93%, 94% 95%, 96%, 97%, 98%, or 99% or more identical to the sequence of the reference sequence of SEQ ID NO:2.

In some embodiments, the nitrilase polypeptides with the improved activity for converting the substrate of formula I to the production of formula II relative to the activity of SEQ ID NO:2 comprises an amino acid sequence that has at least 80%, 85%, 86%, 87%, 88%, 89%, 90%, 91%, 92%, 93%, 94% 95%, 96%, 97%, 98%, or 99% or more identical to the reference sequence of another engineered nitrilase, in particular the reference sequence selected from SEQ ID NO: 6, 84, 122, 130, 138, 358, 360, or 362.

In some embodiments, the nitrilase with improved enzymatic activity comprises an amino acid sequence that has one or more residue differences as compared to SEQ ID NO:2 at the residue positions selected from: X23, X30, X37, X40, X49, X54, X55, X65, X73, X85, X121, X130, X132, X134, X139, X152, X161, X163, X170, X171, X172, X173, X191, X197, X199, X200, X201, X203, X209, X217, X225, X230, X233, X240, X267, X269, X272, X282, X288, X289, X293, X295, X297, X303, X317, X319, X323, X327, X330, X332, and X334. As noted above, the residue differences affecting activity may be present independently or in combination with the residue differences affecting thermo- and/or solvent stability. Thus, in some embodiments, the nitrilase amino acid sequence can include in addition to the residue differences affecting thermo- and/or solvent stability, residue differences at the residue positions above affecting enzymatic activity.

In some embodiments, the amino acid residues at the residue positions affecting enzymatic activity is selected from: X23 is T; X30 is L; X37 is T; X40 is E; X49 is V; X54 is M, V, A, F, or Y; X55 is F; X65 is T; X73 is E; X85 is R; X121 is K; X130 is R; X132 is H, M, L or F; X134 is A; X139 is F or W; X152 is T; X161 is N; X163 is H, W or G; X170 is G; X171 is R; X172 is C; X173 is V; X191 is A, C, I or F; X197 is L, M, or N; X199 is C, H, F, C, V, T, W, M, A, I, F or P; X200 is S; X201 is G; X203 is A; X209 is R; X217 is T; X225 is T; X230 is A, V or Y; X233 is T; X240 is R; X267 is A; X269 is R or P; X272 is E; X282 is I; X288 is T; X289 is V; X293 is T or V; X295 is N; X297 is G, A or V; X303 is P; X317 is A; X319 is M; X323 is G or K; X327 is V; X330 is I; X332 is I or S; and X334 is S, L or I.

In some embodiments, the nitrilase with improved activity comprises an amino acid sequence that includes at least one or more residue differences as compared to SEQ ID NO:2 at residue positions selected from: X30, X54, X73, X132, X199, and X293. In some embodiments, the amino acid at these residue positions is selected from: X30 is L; X54 is M, V, A, F, or Y; X132 is H, M, L or F; X199 is A, F, M, or C; and X293 is T or V.

In some embodiments, where the nitrilase amino acid sequence includes at least one or more residue differences at residue positions X30, X54, X73, X132, X199, and X293, the nitrilase amino acid sequence includes additionally one or more residue differences as compared to SEQ ID NO:2 at residue positions selected from: X23, X37, X40, X49, X55, X59, X65, X85, X94, X121, X130, X134, X152, X161, X163, X170, X171, X172, X173, X191, X197, X200, X201, X203, X209, X217, X225, X233, X240, X267, X269, X272, X282, X288, X289, X295, X297, X303, X317, X319, X323, X327, X330, X332, and X334. In some embodiments, the amino acid residue at the residue positions are selected from: X23 is T; X37 is T; X40 is E; X49 is V; X55 is F; X65 is T; X85 is R; X121 is K; X130 is R; X134 is A; X152 is T; X161 is N; X163 is W, H or G; X170 is G; X171 is R; X172 is C; X173 is V; X191 is I, A or C; X197 is M, L or N; X200 is S; X201 is G; X203 is A; X209 is R; X217 is T; X225 is T; X233 is T; X240 is R; X267 is A; X269 is R or P; X272 is E; X282 is I; X288 is T; X289 is V; X295 is N; X297 is V, G, or A; X303 is P; X317 is A; X319 is M; X323 is G or K; X327 is V; X330 is I; X332 is I or S; and X334 is S, I or A.

In some embodiments, the nitrilase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, or 1-40 residue differences as compared to SEQ ID NO:2 at other residue positions than those specific positions listed above. In some embodiments, the number of differences can be 1, 2, 3, 4, 5, 6, 7, 8, 9, 10, 11, 12, 14, 15, 16, 18, 20, 22, 24, 26, 30, 35, or 40 residue differences at the other residue positions. In some embodiments, the amino acid residue at the other residue positions can comprise conservative residue differences as compared to the sequence of SEQ ID NO:2.

In some embodiments the other residue positions are selected from: X7, X10, X13, X18, X20, X62, X119, X135, X185, X195, X228, X238, X242, X249, X259, X268, X270, X273, X277, X291, X308, X318, X324, X326, X328, X329, and X333. In some embodiments, the amino acid residues at these other residue positions are selected from: X7 is E; X10 is A; X13 is G; X18 is L; X62 is V; X119 is V; X135 is H; X185 is P; X195 is E; X228 is R; X238 is A; X242 is A or G; X249 is E or V; X259 is I; X268 is D or K; X270 is P; X273 is A; X277 is L; X291 is E; X308 is P or R; X318 is Y; X324 is N; X326 is Y; X328 is P; X329 is I; and X333 is A.

In some embodiments, the nitrilase enzyme can be a fusion polypeptide in which the nitrilase polypeptide is fused to other polypeptides, particularly heterologous polypeptides, such as antibody tags (e.g., myc epitope) or purifications sequences (e.g., His tags). Thus, the nitrilase polypeptides can be used with or without fusions to other polypeptides.

In some embodiments, the nitrilase polypeptide further comprises a fusion of the carboxy terminus (C-terminal) to a polypeptide of SEQ ID NO: 378 or 380, or at least a contiguous segment of 17 amino acids of SEQ ID NO: 378 or 380. It has been observed that these polypeptides when fused to the C-terminus of the nitrilase polypeptides can increase the production of soluble protein during expression. The sequences of the following engineered nitrilase include such a C-terminal fusion: SEQ ID NO: 4, 14, 184, 322, 324, 326, 328, 330, 332, 334, 336, 338, 340, 342, 344, 346, 348, 350, 352, 354, and 356. For SEQ ID NOs: 4, 14, 366, 368, and 370, it was found that the C-terminal extension is at least 17 amino acids and results in about 1.2-fold to about 4.2-fold increased production of soluble protein during expression relative to SEQ ID NO: 6, which did not have the C-terminal extension. Additionally, it was found that the majority of protein of SEQ ID NO: 4 expressed was soluble, while the majority of expressed protein of SEQ ID NO: 368 (which has the same sequence as SEQ ID NO: 4 except for the C-terminal fusion) was insoluble. The C-terminal fusion for all but SEQ ID NO: 322 comprises the 17 amino acid sequence of SEQ ID NO: 378. The C-terminal fusion of SEQ ID NO: 322 comprises the 17 amino acid sequence of SEQ ID NO: 380, which differs in one amino acid relative to SEQ ID NO: 379. It is to be understood that the carboxy terminal fusion represented by SEQ ID NO: 378 or 380 can be practiced with any of the engineered nitrilase polypeptides disclosed herein, and therefore is not limited to the exemplary amino acid sequences that have the C-terminal fusion sequences.

In some embodiments, the engineered nitrilase polypeptide can comprise an amino acid sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, and 372.

In some embodiments, the engineered nitrilase polypeptide having improved thermo- and/or solvent stability, and/or improved activity relative to SEQ ID NO:2 can comprise an amino acid sequence selected from SEQ ID NO: 4, 6, 8, 10, 12, 14, 16, 18, 20, 22, 24, 26, 28, 44, 70, 72, 76, 78, 80, 84, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, and 372.

It is noted that SEQ ID NO: 368 is the same as SEQ ID NO: 4 without the carboxy-terminal fusion. SEQ ID NO: 366 is also the same as SEQ ID NO:4 without the carboxy terminal fusion except that SEQ ID NO: 366 also includes T at residue position X334. In some embodiments, the present disclosure provides engineered polypeptide sequences of SEQ ID NOs: 4, 14, 184, 322, 324, 326, 328, 330, 332, 334, 336, 338, 340, 342, 344, 346, 348, 350, 352, 354, and 356, without the carboxy-terminal fusion that begin at residue position X335. Accordingly, the present disclosure provides engineered polypeptides comprising the sequence of amino acids from residue position 1 to residue position 334 of any one of SEQ ID NOs: 4, 14, 184, 322, 324, 326, 328, 330, 332, 334, 336, 338, 340, 342, 344, 346, 348, 350, 352, 354, and 356.

Table 2 below provides exemplary engineered nitrilase polypeptides, with each row listing two SEQ ID NOs, the odd number referring to the nucleotide sequence encoding the amino acid sequence provided by the even number. The residue differences are based on comparison to reference sequence of SEQ ID NO:2, the naturally occurring nitrilase of *Bradyrhizobium japonicum*. Exemplary assay conditions for measuring activity using specific nitrilase substrates are provided in the Examples.

TABLE 2

| SEQ ID NO | Residue differences relative to SEQ ID NO: 2 | C-Terminal Fusion |
|---|---|---|
| 1/2 | | |
| 3/4 | F30L; A91R; Y139F; I166L; M230V; M309L; T334S | + |
| 5/6 | A91R; T108S; Y139F; I166L; M230V; M266L | |
| 7/8 | A91R; Y139F; I166L; M230V; A293T; M309L | |
| 9/10 | A91R; Y139F; I166L; Y197L; M230V; M309L; T334I | |
| 11/12 | A91R; Y139F; I166L; L199C; M230V; M309L | |
| 13/14 | A91R; T108S; Y139F; I166L; M230V; M266L; T334L | + |
| 15/16 | W54F; A91R; T108S; Y139F; I166L; M230V; M266L | |
| 17/18 | W54M; A91R; T108S; Y139F; I166L; M230V; M266L | |
| 19/20 | A91R; T108S; T132F; Y139F; I166L; M230V; M266L | |
| 21/22 | A91R; T108S; Y139F; C161N; I166L; M230V; M266L | |
| 23/24 | A91R; T108S; Y139F; A163G; I166L; M230V; M266L | |
| 25/26 | A91R; T108S; Y139F; A163W; I166L; M230V; M266L | |
| 27/28 | A91R; T108S; Y139F; I166L; L191I; M230V; M266L | |
| 29/30 | L191I | |
| 31/32 | W54V | |
| 33/34 | L191A | |
| 35/36 | W54M | |
| 37/38 | L191C | |
| 39/40 | W54F | |
| 41/42 | A163W | |
| 43/44 | M230A | |
| 45/46 | D242A | |
| 47/48 | A163H | |
| 49/50 | C161N | |
| 51/52 | L199A | |
| 53/54 | P238A | |
| 55/56 | A163G | |
| 57/58 | E135H | |
| 59/60 | A119V | |
| 61/62 | T132F | |
| 63/64 | T132H | |
| 65/66 | T132M | |
| 67/68 | V282I; G303P; M309L | |
| 69/70 | I166L | |
| 71/72 | T108S; M266L;G303P; M309L | |
| 73/74 | S152T; L270P | |
| 75/76 | T108S | |
| 77/78 | V10A; Y139F; I166L; M266L | |
| 79/80 | T108S; G303P | |
| 81/82 | V282I | |
| 83/84 | T108S; V282I; N326Y | |

TABLE 2-continued

| SEQ ID NO | Residue differences relative to SEQ ID NO: 2 | C-Terminal Fusion |
|---|---|---|
| 85/86 | I166L | |
| 87/88 | T108S; S152T; I166L; I277L; T297A | |
| 89/90 | T108S; Y139F; S152T | |
| 91/92 | K7E; A20L; Y139F | |
| 93/94 | T108S; Y139F; S152T | |
| 95/96 | Y139F; | |
| 97/98 | Y139F; I166L; M309L | |
| 99/100 | I166L; M266L | |
| 101/102 | I166L; M266L; G303P | |
| 103/104 | T108S; Y139F; E268K; L308P | |
| 105/106 | A20L; T108S; Y139F; S152T; S185P; A249E; K291E; G303P | |
| 107/108 | A62V; T108S; Y139F; I166L; M266L | |
| 109/110 | T108S; Y139F; S152T; I166L; K195E; I277L; V282I | |
| 111/112 | A20L; Y139F; I166L | |
| 113/114 | T108S; Y139F; M266L; M309L | |
| 115/116 | V10A; M18L; S152T; I166L; L308R | |
| 117/118 | T108S; S152T; I166L; M266L; V282I | |
| 119/120 | T108S; Y139F; M266L | |
| 121/122 | Y139F; I166L | |
| 123/124 | Y139F; S152T; I166L; A249V; E268D; H269P; D273A; G303P | |
| 125/126 | T108S; Y139F; I166L; M266L; V282I; G303P; M309L | |
| 127/128 | Y139F; I166L; M266L; I277L; V282I | |
| 129/130 | I166L; M309L | |
| 131/132 | T108S; M266L | |
| 133/134 | A13G; T108S; Y139F; S152T; M266L; M309L; T317A | |
| 135/136 | I166F; D242G; S318Y; A328P; V329I; E333A | |
| 137/138 | Y139F; I166L; M309L | |
| 139/140 | I166L; V282I | |
| 141/142 | T108S; Y139F; M266L | |
| 143/144 | A91R; Y139F; I166L; Y197M; M230V; M309L | |
| 145/146 | A91R; Y139F; I166L; Y197L; M230V; M309L | |
| 147/148 | A91R; Y139F; I166L; Y197M; M230V; M309L | |
| 149/150 | A91R; Y139F; I166L; L199H; M230V; M309L | |
| 151/152 | A91R; Y139F; I166L; L199F; M230V; M309L | |
| 153/154 | A91R; Y139F; I166L; M230V; M309L; T332I | |
| 155/156 | A91R; Y139F; I166L; L199C; M230V; M309L | |
| 157/158 | A91R; Y139F; I166L; L199V; M230V; M309L | |
| 159/160 | A91R; Y139F; I166L; L199T; M230V; M309L | |
| 161/162 | A91R; Y139F; I166L; L199W; M230V; M309L | |
| 163/164 | A91R; Y139F; I166L; L199P; M230V; M309L | |
| 165/166 | A91R; Y139F; I166L; L199M; M230V; M309L | |
| 167/168 | A91R; Y139F; I166L; L199A; M230V; M309L | |
| 169/170 | A91R; Y139F; I166L; L199I; M230V; M309L | |
| 171/172 | A91R; Y139F; I166L; L199F; M230V; H269R; M309L | |
| 173/174 | A91R; T108S; Y139F; I166L; M230V; M266L; T334I | |
| 175/176 | A91R; T108S; Y139F; I166L; Y197N; M230V; M266L | |
| 177/178 | S23T; A91R; T108S; Y139F; I166L; K171R; M230V; M266L | |
| 179/180 | S23T; A91R; T108S; V134A; Y139F; I166L; M230V; M266L; T297V | |
| 181/182 | A91R; T108S; Y139W; I166L; M230V; M266L; C267A; H269P | |
| 183/184 | A91R; T108S; K130R; Y139F; I166L; S170G; M230V; M266L; H269P; T297V | + |
| 185/186 | A91R; T108S; Y139W; I166L; M230V; F259I; M266L; V319M | |
| 187/188 | A73E; A91R; T108S; Y139F; I166F; M230V; M266L; Q272E; A327V | |
| 189/190 | A91R; T108S; Y139F; I166L; V203A; M230V; M266L | |
| 191/192 | A73E; A91R; T108S; Y139F; I166F; M230V; M266L | |
| 193/194 | A91R; T108S; Y139F; I166F; V203A; M230V; M266L; T330I | |
| 195/196 | A91R; T108S; Y139F; I166F; Y172C; M230V; M266L; Q272E | |
| 197/198 | A91R; T108S; Y139F; I166F; V203A; C217T; M230V; M266L | |

TABLE 2-continued

| SEQ ID NO | Residue differences relative to SEQ ID NO: 2 | C-Terminal Fusion |
|---|---|---|
| 199/200 | K40E; A85R; A91R; T108S; Y139F; I166L; M230V; M266L; Q272E; I289V | |
| 201/202 | A73E; A91R; T108S; Y139F; I166F; C217T; M230V; M266L; Q272E | |
| 203/204 | A73E; A91R; T108S; Y139F; I166F; M230V; M266L | |
| 205/206 | A91R; Y139F; I166L; M230Y; M309L | |
| 207/208 | W54V; A91R; T108S; Y139F; I166L; M230V; M266L | |
| 209/210 | A91R; T108S; T132H; Y139F; I166L; M230V; M266L; | |
| 211/212 | A91R; T108S; T132M; Y139F; I166L; M230V; M266L | |
| 213/214 | A91R; T108S; T132L; Y139F; I166L; M230V; M266L | |
| 215/216 | A91R; T108S; Y139F; I166L; L199A; M230V; M266L | |
| 217/218 | W54A; A91R; T108S; Y139F; I166L; M230V; M266L | |
| 219/220 | A91R; T108S; Y139F; C161N; I166L; L199F; M230V; M266L | |
| 221/222 | A91R; T108S; Y139F; I166L; H201G; M230V; M266L | |
| 223/224 | A91R; T108S; Y139F; I166L; Y197M; M230V; M266L; T317A | |
| 225/226 | A37T; A91R; T108S; Y139F; C161N; I166L; G200S; M230V; M266L | |
| 227/228 | W54A; A91R; T108S; Y139F; I166L; L199M; M230V; M266L | |
| 229/230 | A91R; T108S; Y139F; C161N; I166L; M230V; M266L | |
| 231/232 | A91R; T108S; Y139F; C161N; I166L; L199C; M230V; M266L | |
| 233/234 | W54V; A91R; T108S; Y139F; I166L; L199M; M230V; M266L | |
| 235/236 | W54V; A91R; T108S; Y139F; C161N; I166L; L199M; M230V; M233T; M266L | |
| 237/238 | A91R; T108S; Y139F; C161N; I166L; L199M; M230V; M266L | |
| 239/240 | W54V; A91R; T108S; Y139F; C161N; I166L; L199F; M230V; M266L | |
| 241/242 | W54V; A91R; T108S; Y139F; I166L; L199M; M230V; M266L | |
| 243/244 | W54V; A91R; T108S; Y139F; C161N; I166L; G200S; M230V; K240R; M266L; A288T | |
| 245/246 | W54V; A91R; T108S; Y139F; I166L; L199M; M230V; M266L; | |
| 247/248 | I49V; W54M; A91R; T108S; E121K; Y139F; C161N; I166L; L199M; M230V; M266L | |
| 249/250 | W54F; M65T; A91R; T108S; Y139F; A163G; I166L; L199C; M230V; M266L; A293T | |
| 251/252 | W54M; A91R; T108S; T132F; Y139F; I166L; L199C; M230V; M266L | |
| 253/254 | W54M; A91R; T108S; T132F; Y139F; A163G; I166L; L199F; M230V; M266L | |
| 255/256 | W54M; A91R; T108S; T132F; Y139F; I166L; L199C; M230V; M266L | |
| 257/258 | W54F; A91R; T108S; T132F; Y139F; C161N; I166L; L199C; M230V; M266L | |
| 259/260 | A91R; T108S ; T132F; Y139F; I166L; L199C; M230V; M266L | |
| 261/262 | W54M; A91R; T108S; T132F; Y139F; I166L; L199C; M230V; M266L; A293T | |
| 263/264 | W54M; A91R; T108S; T132F; Y139F; I166L; L199C; M230V; M266L; A293T | |
| 265/266 | W54M; A91R; T108S; Y139F; I166L; L199F; Q209R; M230V; M266L; A293T | |
| 267/268 | W54M; A91R; T108S; T132F; Y139F; C161N; I166L; L199F; M230V; M266L | |
| 269/270 | W54M; A91R; T108S; T132F; Y139F; A163G; I166L; L199C; M230V; M266L | |
| 271/272 | W54M; A91R; T108S; T132F; Y139F; I166L; L199C; M230V; M266L; A293T | |
| 273/274 | W54F; A91R; T108S; Y139F; I166L; L199C; M230V; M266L | |
| 275/276 | W54M; A91R; T108S; T132F; Y139F; A163G; I166L; L199C; M230V; M266L | |

TABLE 2-continued

| SEQ ID NO | Residue differences relative to SEQ ID NO: 2 | C-Terminal Fusion |
|---|---|---|
| 277/278 | W54F; A91R; T108S; Y139F; A163G; I166L; L199C; M230V; M266L; A293T | |
| 279/280 | W54F; A91R; T108S; T132F; Y139F; C161N; I166L; L199C; M230V; M266L; A293T | |
| 281/282 | A91R; T108S; Y139F; A163G; I166L; L199C; M230V; M266L; A293T | |
| 283/284 | W54M; A91R; T108S; Y139F; A163G; I166L; L199C; M230V; M266L; A293T | |
| 285/286 | W54M; A91R; T108S; T132F; Y139F; I166L; L199C; M230V; M266L; A293T | |
| 287/288 | W54M; A91R; T108S; Y139F; A163G; I166L; L199C; M230V; M266L; A293T | |
| 289/290 | W54M; A91R; T108S; T132F; Y139F; A163G; I166L; L199C; M230V; M266L; A293T | |
| 291/292 | A91R; T108S; T132F; Y139F; I166L; L199C; M230V; M266L; A293T | |
| 293/294 | W54F; A91R; T108S; T132F; Y139F; I166L; L199C; M230V; M266L; A293T | |
| 295/296 | W54M; A91R; T108S; Y139F; A163G; I166L; L199C; M230V; M266L; A293T; E323G; | |
| 297/298 | W54F; A91R; T108S; Y139F; I166L; L191I; M230V; M266L; A293T; T332I | |
| 299/300 | W54F; A91R; T108S; Y139F; I166L; M230V; M266L; A293T | |
| 301/302 | A91R; T108S; Y139F; I166L; L191I; M230V; M266L; A293T | |
| 303/304 | A91R; T108S; T132H; Y139F; I166L; L191I; M230V; M266L | |
| 305/306 | A91R; T108S; Y139F; I166L; M230V; M266L; A293T | |
| 307/308 | W54F; A91R; T108S; Y139F; I166L; L191I; I225T; M230V; M266L; A293T; | |
| 309/310 | A91R; T108S; T132H; Y139F; A163G; I166L; L191I; M230V; M266L | |
| 311/312 | W54F; A91R; T108S; Y139F; I166L; L191I; M230V; M266L; A293T | |
| 313/314 | A91R; T108S; T132H; Y139F; A163G; I166L; L191I; Q209R; Q228R; M230V; M266L; A293T | |
| 315/316 | A91R; T108S; Y139F; I166L; Y172C; L191I; M230V; M266L; A293T; | |
| 317/318 | A91R; T108S; Y139F; A163G; I166L; Y172C; L191I; M230V; M266L; A293T | |
| 319/320 | A91R; T108S; T132F; Y139F; A163W; I166L; M230V; M266L; A293T | |
| 321/322 | F30L; W55F; A91R; Y139F; I166L; M230V; D295N; M309L; T317A; E323K; D324N; T334S | + |
| 323/324 | F30L; A91R; Y139F; S152T; I166L; M230V; V282I; G303P; M309L; T334S; | + |
| 325/326 | F30L; W54M; A91R; Y139F; I166L; M230V; A293T; M309L; T334S | + |
| 327/328 | F30L; A91R; Y139F; I166L; Y172C; L191I; M230V; M309L; T334S | + |
| 329/330 | S23T; F30L; A91R; Y139F; I166L; M230V; M309L; T317A; T334S | + |
| 331/332 | S23T; F30L; A91R; Y139F; I166L; G200S; M230V; T297V; M309L; T33 4S | + |
| 333/334 | S23T; F30L; A91R; Y139F; I166L; M230V; T297V; M309L; T334S | + |
| 335/336 | F30L; A91R; Y139F; I166L; M230V; A293V; T297G; M309L; T317A; T334S | + |
| 337/338 | S23T; F30L; A91R; Y139F; I166L; M230V; T297V; M309L; T317A; T334S | + |
| 339/340 | F30L; A91R; Y139F; I166L; G200S; V203A; M230V; M309L; T317A; T334S | + |
| 341/342 | F30L; A91R; Y139F; I166L; M230V; T297V; M309L; T317A; T334S | + |
| 343/344 | F30L; A91R; Y139F; I166L; M230V; T297V; M309L; T317A; T334S | + |
| 345/346 | S23T; F30L; A91R; Y139F; I166L; G200S; M230V; M309L; T334S; | + |
| 347/348 | S23T; F30L; A91R; Y139F; I166L; M230V; M309L; T317A; T334S; | + |
| 349/350 | F30L; A91R; Y139F; I166L; M230V; M309L; T317A; T334S | + |
| 351/352 | F30L; W54Y; A91R; Y139F; I166L; M230V; M309L; T334S | + |

TABLE 2-continued

| SEQ ID NO | Residue differences relative to SEQ ID NO: 2 | C-Terminal Fusion |
|---|---|---|
| 333/354 | F30L; A91R; Y139F; I166L; L191F; M230V; M309L; T334S | + |
| 355/356 | F30L; A91R; Y139F; I166L; A173V; M230V; M309L; T332S; T334S; | + |
| 357/358 | T108S; Y139F; I166L; M266L | |
| 359/360 | A91R; M230V | |
| 361/362 | A91R; Y139F; I166L; M230V | |
| 363/364 | A91R; Y139F; I166L; M230V; M309L | |

In some embodiments, the improved nitrilase polypeptide comprises an amino acid sequence that is at least about 80%, 85%, 86%, 87%, 88%, 89%, 90%, 91%, 92%, 93%, 94%, 95%, 96%, 97%, 98%, 99% or more identical to a reference sequence of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362 or 364. In some embodiments, the improved nitrilase polypeptides can have 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, or 1-40 residue differences as compared to the naturally occurring nitrilase represented by SEQ ID NO:2. In some embodiments, the number of residue differences can be 1, 2, 3, 4, 5, 6, 7, 8, 9, 10, 11, 12, 14, 15, 16, 18, 20, 22, 24, 26, 30, 35, or 40 differences as compared to SEQ ID NO:2.

In some embodiments, the improved nitrilase polypeptide comprises an amino acid sequence that is at least about 80%, 85%, 86%, 87%, 88%, 89%, 90%, 91%, 92%, 93%, 94%, 95%, 96%, 97%, 98%, or 99% identical to a reference sequence based on SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362 or 364, with the proviso that the improved nitrilase amino acid sequence comprises any one of the set of residue differences contained in any one of the polypeptide sequences listed in Table 2 as compared to SEQ ID NO:2. In some embodiments, the nitrilase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, or 1-40 residue differences at other amino acid residue positions as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35, or 40 residue differences at other residue positions. In some embodiments, the residue differences at other residue positions comprise substitutions with conservative amino acid residues.

As noted above, the nitrilase activity can be examined for the conversion of the substrate of formula I to the product of formula II. Specific substrates encompassed within the formula can be used to assess properties of the enzyme, including among others, enzymatic activity of the engineered nitrilases and its stability. Products of the specific reactions can also be useful chemical intermediates in the synthesis of pharmaceuticals and other compounds. Accordingly, in some embodiments, the nitrilase polypeptide is capable of converting the substrate of formula I to the product of formula II with at least 1.1 fold the activity of the polypeptide of SEQ ID NO:2, where the substrate of formula I is specified below.

In some embodiments, the substrate of formula I is Ia:

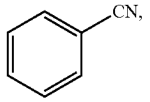

(Ia)

and the product of formula II is IIa:

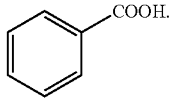

(IIa)

In some embodiments, the substrate of formula I is Ib:

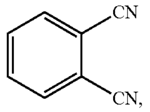

(Ib)

and the product of formula II is IIb:

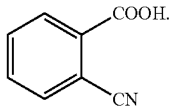

(IIb)

In some embodiments, the substrate of formula I is Ic:

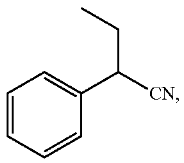

(Ic)

and the product of formula II is IIc':

(IIc')

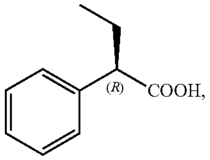

and/or IIc":

(IIc")

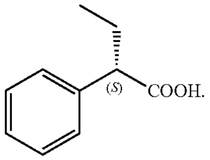

In some embodiments, the substrate of formula I is Id:

(Id)

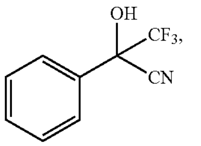

and the product of formula II is IId':

(IId')

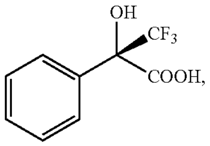

and/or IId":

(IId")

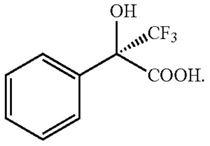

In some embodiments, the substrate of formula I is Ie:

(Ie)

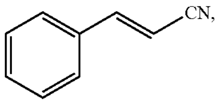

and the product of formula II is IIe':

(IIe')

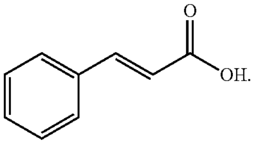

In some embodiments, the substrate of formula I is If:

(If)

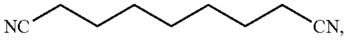

and the product of formula II is IIf:

(IIf)

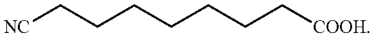

In some embodiments, the substrate of formula I is Ig:

(Ig)

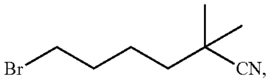

and the product of formula II is IIg:

(IIg)

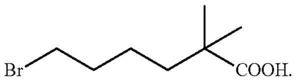

In some embodiments, the substrate of formula I is Ih:

(Ih)

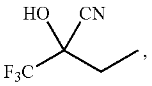

and the product of formula II is IIh:

(IIh)

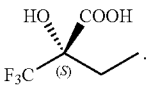

In some embodiments, the substrate of formula I is Ii:

(Ii)

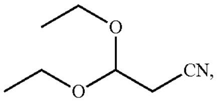

and the product of formula II is IIi:

(IIi)

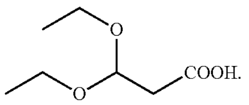

In some embodiments, the substrate of formula I is Ij:

(Ij)

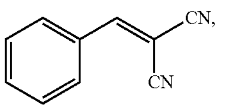

and the product of formula II is IIj:

(IIj)

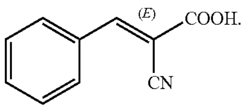

While reactions carried out the by nitrilase enzymes produce the corresponding acid without significant production or release of an amide, in some embodiments, the nitrilase polypeptides can be engineered to favor production of the amide for certain substrates. Accordingly, in some embodiments in which the substrate is Ie, the nitrilase polypeptide is capable of also forming the amide product of IIe'':

(IIe'')

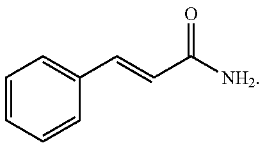

It is to be understood that activities of the nitrilase polypeptides on the specific substrates are not mutually exclusive and that nitrilases capable of acting on one specific substrate to form the corresponding product can be capable of acting on another specific substrate to form its corresponding product.

In some embodiments, the residue differences as compared to SEQ ID NO:2 associated with improvements in enzymatic activity can be present to improve the enzymatic activity with respect to each specific substrate described in the foregoing. As noted above, these residue differences associated with improved activity can be present independently of or in combination with the residue differences associated with thermo- and/or solvent stability. Thus, in some embodiments, the nitrilase amino acid sequence includes in addition to the residue differences associated with thermo- and/or solvent stability, one or more of the residue differences associated with improvements in enzymatic acivity relative to SEQ ID NO:2.

Accordingly, in some embodiments in which the substrate is Ia and the product is IIa, the nitrilase amino acid sequence has one or more residue differences as compared to SEQ ID NO:2 at residue positions selected from: X30, X54, X161, X163, X191, X197, X199, X230, X242, X269, X293, and X334. In some embodiments, the amino acid residues at the residue positions are selected from: X30 is L; X54 is F, M, V or A; X161 is N; X163 is W or H; X197 is L, M, or N; X199 is C, H, F, C, V, T, W, M, A, I or F; X230 is A or Y; X238 is A; X242 is A; X269 is R; X293 is T; and X334 is I, S or L.

In some embodiments for the nitrilase polypeptide having one or more residue differences at residue positions selected from X30, X54, X161, X163, X191, X197, X199, X230, X242, X269, X293, and X334, the nitrilase amino acid sequence can include additionally one or more residue differences as compared to SEQ ID NO:2 at residue positions selected from: X23, X37, X40, X49, X55, X59, X65, X73, X85, X94, X121, X130, X132, X134, X152, X170, X171, X172, X173, X200, X201, X203, X209, X217, X225, X233, X240, X267, X272, X282, X288, X289, X295, X297, X303, X317, X319, X323, X327, X330, and X332. In some embodiments, the amino acid residues for the residue positions is selected from: X23 is T; X37 is T; X40 is E; X49 is V; X55 is F; X65 is T; X73 is E; X85 is R; X121 is K; X130 is R; X132 is F, H, M, or L; X134 is A; X152 is T; X170 is G; X171 is R; X172 is C; X173 is V; X200 is S; X201 is G; X203 is A; X209 is R; X217 is T; X225 is T; X233 is T; X240 is R; X267 is A; X272 is E; X282 is I; X288 is T; X289 is V; X295 is N; X297 is V, G, or A; X303 is P; X317 is A; X319 is M; X323 is G or K; X327 is V; X330 is I; and X332 is I or S.

In some embodiments of the nitrilase with improved activity for conversion of substrate Ia to the product IIa, the nitrilase amino acid sequence can include additionally 1 to 40 residue differences as compared to SEQ ID NO:2 at other residue positions than those described above. In some embodiments these residue differences comprises conservative residue differences. In some embodiments, the other residue positions are selected from: X7, X10, X13, X18, X20, X62, X119, X135, X185, X195, X228, X249, X259, X268, X270, X273, X277, X291, X308, X318, X324, X326, X328, X329, and X333. In some embodiments, the amino acid residue at the residue positions is selected from: X7 is E; X10 is A; X13 is G; X18 is L; X20 is L; X62 is V; X119 is V; X135 is H; X185 is P; X195 is E; X228 is R; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

In some embodiments, the nitrilase having at least 1.1-fold improved activity relative to the activity of SEQ ID NO:2 for converting substrate Ia to the product IIa comprises an amino acid sequence selected from SEQ ID NO: 4, 8, 10, 12, 14, 16, 18, 22, 30, 32, 34, 36, 38, 40, 42, 44, 46, 50, 52, 54, 56, 144, 150, 152, 156, 158, 160, 162, 166, 168, 170, 172, 174, 176, 206, 208, 216, and 218.

In some embodiments in which the substrate is Ib and the product is IIb, the nitrilase amino acid sequence has one or more residue differences as compared to SEQ ID NO:2 at residue positions selected from: X23, X54, X65, X73, X121, X132, X134, X161, X163, X171, X172, X197, X199, X200, X201, X203, X209, X217, X233, X240, X293, X297, X317, and X330. In some embodiments, the amino acid residue at the residue positions is selected from: X23 is T; X54 is M, F, V, or A; X65 is T; X73 is E; X121 is K; X132 is F; X134 is A; X161 is N; X163 is G; X171 is R; X172 is C; X197 is M; X199 is C, F or M; X200 is S; X201 is G; X203 is A; X209 is R; X217 is T; X233 is T; X240 is R; X293 is T; X297 is V; X317 is A; and X330 is I.

In some embodiments for the nitrilase polypeptide having one or more residue differences at residue positions selected from X23, X54, X65, X73, X121, X132, X134, X161, X163, X171, X172, X197, X199, X200, X201, X203, X209, X217, X233, X240, X293, X297, X317, and X330, the nitrilase amino acid sequence can include additionally one or more residue differences as compared to SEQ ID NO:2 at residue positions selected from: X30, X37, X40, X49, X55, X59, X85, X94, X130, X152, X170, X173, X191, X225, X267, X269, X272, X282, X288, X289, X295, X303, X319, X323, X327, X332, and X334. In some embodiments, the amino acid residue at the residue positions is selected from: X30 is L; X37 is T; X40 is E; X49 is V; X55 is F; X85 is R; X130 is R; X152 is T; X170 is G; X173 is V; X191 is I, A or C; X225 is T; X267 is A; X269 is R or P; X272 is E; X282 is I; X288 is T; X289 is V; X295 is N; X303 is P; X319 is M; X323 is G or K; X327 is V; X332 is I or S; and X334 is S, I or A.

In some embodiments of the nitrilase with improved activity for conversion of substrate Ib to the product IIb, the nitrilase amino acid sequence can include additionally 1 to 40 residue differences as compared to SEQ ID NO:2 at other residue positions than those described above. In some embodiments these residue differences comprise conservative residue differences. In some embodiments, the other residue positions are selected from: X7, X10, X13, X18, X20, X62, X119, X135, X185, X195, X228, X238, X242, X249, X259, X268, X270, X273, X277, X291, X308, X318, X324, X326, X328, X329, and X333. In some embodiments, the amino acid residue at the residue positions is selected from: X7 is E; X10 is A; X13 is G; X18 is L; X20 is L; X62 is V; X119 is V; X135 is H; X185 is P; X195 is E; X228 is R; X238 is A; X242 is A or G; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

In some embodiments, the nitrilase having at least 1.1-fold improved activity relative to the activity of SEQ ID NO:2 for converting substrate Ib to the product IIb comprises an amino acid sequence selected from SEQ ID NO: 178, 180, 190, 192, 194, 196, 198, 202, 204, 220, 222, 224, 226, 228, 232, 234, 236, 238, 240, 242, 244, 246, 248, 250, 252, 254, 256, 258, 260, 262, 264, 266, 268, 270, 272, 274, 276, 278, 282, 284, 288, 290, 292, 296, or 300.

In some embodiments in which the substrate is Ic and the products are IIc' and/or IIc", the nitrilase amino acid sequence has one or more residue differences as compared to SEQ ID NO:2 at residue positions selected from: X30, X54, X65, X132, X163, X172, X191, X197, X199, X225, X238; X293, X332, and X334. In some embodiments, the amino acid residue at the residue positions is selected from: X30 is L; X54 is F or M; X65 is T; X132 is H, M, L or F; X163 is G; X172 is C; X191 is I; X197 is L; X199 is C; X225 is T; X238 is A; X293 is T; X332 is I; and X334 is I, L or S.

In some embodiments for the nitrilase polypeptide having one or more residue differences at residue positions selected from X30, X54, X65, X132, X163, X172, X191, X197, X199, X225, X293, X332, and X334, the nitrilase amino acid sequence can include additionally one or more residue differences as compared to SEQ ID NO:2 at residue positions selected from: X23, X37, X40, X49, X55, X59, X73, X85, X94, X121, X130, X134, X152, X161, X170, X171, X173, X200, X201, X203, X209, X217, X233, X240, X267, X269, X272, X282, X288, X289, X295, X297, X303, X317, X319, X323, X327, and X330. In some embodiments, the amino acid residue at the residue positions is selected from: X23 is T; X37 is T; X40 is E; X49 is V; X55 is F; X73 is E; X85 is R; X121 is K; X130 is R; X134 is A; X152 is T; X161 is N; X170 is G; X171 is R; X173 is V; X200 is S; X201 is G; X203 is A; X209 is R; X217 is T; X233 is T; X240 is R; X267 is A; X269 is R or P; X272 is E; X282 is I; X288 is T; X289 is V; X295 is N; X297 is V, G, or A; X303 is P; X317 is A; X319 is M; X323 is G or K; X327 is V; and X330 is I.

In some embodiments of the nitrilase with improved activity for conversion of substrate Ic to the products IIc' and IIc", the nitrilase amino acid sequence can include additionally 1 to 40 residue differences as compared to SEQ ID NO:2 at other residue positions than those described above. In some embodiments these residue differences comprise conservative residue differences. In some embodiments, the other residue positions are selected from: X7, X10, X13, X18, X20, X62, X119, X135, X185, X195, X228, X242, X249, X259, X268, X270, X273, X277, X291, X308, X318, X324, X326, X328, X329, and X333. In some embodiments, the amino acid residue at the residue positions is selected from: X7 is E; X10 is A; X13 is G; X18 is L; X20 is L; X62 is V; X119 is V; X135 is H; X185 is P; X195 is E; X228 is R; X242 is A or G; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

In some embodiments, the nitrilase having at least 1.1-fold improved activity relative to the activity of SEQ ID NO:2 for converting substrate Ic to the products IIc' and/or IIc" comprises an amino acid sequence selected from SEQ ID NO: 4, 8, 10, 14, 20, 24, 28, 42, 44, 54, 154, 174, 210, 212, 214, 250, 256, 270, 276, 284, 288, 298, 300, 302, 304, 308, 310, 312, 316, and 318.

In some embodiments, the nitrilase polypeptide are capable of converting substrate Ic to product IIc" in enantiomeric excess of IIc'. In some embodiments, the nitrilase polypeptides are capable of producing IIc" in at least 20% enantiomeric excess, at least 40% enantiomeric excess, at least 80% enantiomeric excess, or at least 90% or more enantiomeric excess of product IIc'.

In some embodiments, the nitrilase polypeptide capable converting substrate Ic to product IIc" in enantiomeric excess comprises an amino acid sequence that has one or more residue differences as compared to SEQ ID NO:2 selected from: X54 is F or M; X132 is H, M, or L; X163 is G, and X293 is T. In some embodiments, the nitrilase polypeptide capable of converting substrate Ic to product IIc" in enantiomeric excess comprises an amino acid sequence selected from: SEQ ID NO: 20, 24, 210, 212, 214, 250, 252, 254, 256, 258, 260, 262, 264, 268, 270, 276, 278, 280, 282, 284, 286, 288, 290, 292, 294, 296, 300, 304, 306, 308, 310 and 314.

In some embodiments, the nitrilase polypeptide are capable of converting substrate Ic to product IIc' in enantiomeric excess of IIc". In some embodiments, the nitrilase polypeptides are capable of producing IIc' in at least 20% enantiomeric excess, at least 40% enantiomer excess, at least 80% enantiomeric excess, or at least 90% or more enantiomer excess of product IIc'.

In some embodiments, the nitrilase polypeptide capable converting substrate Ic to product IIc' in enantiomeric excess comprises an amino acid sequence that has one or more residue differences as compared to SEQ ID NO:2 selected from: X54 is A; X139 is W; X163 is W; X171 is R; X197 is L or N; X199 is A; X203 is A; X267 is A; and X269 is P. In some embodiments, the nitrilase polypeptide capable of converting substrate Ic to product IIc' in enantiomeric excess comprises an amino acid sequence selected from: SEQ ID NO: 26, 146, 152, 156, 176, 178, 182, 190, 216, 218 or 320.

In some embodiments in which the substrate is Id and the products are IId' and/or IId", the nitrilase amino acid sequence has one or more residue differences as compared to SEQ ID NO:2 at residue positions selected from: X23, X30, X37, X40, X54, X73, X85, X130, X132, X134, X161, X163, X170, X172, X191, X197, X199, X200, X201, X203, X209, X269, X272, X289, X293, X297, X327, X330, and X334. In some embodiments, the amino acid residue at the residue positions is selected from: X23 is T; X30 is L; X37 is T; X40 is E; X54 is M; X73 is E; X85 is R; X130 is R; X132 is H; X134 is A; X161 is N; X163 is G; X170 is G; X172 is C; X191 is I; X197 is L; X199 is M or F; X200 is S; X201 is G; X203 is A; X209 is R; X269 is P; X272 is E; X289 is V; X293 is T; X297 is V; X327 is V; X330 is I; and X334 is I, S, or L.

In some embodiments for the nitrilase polypeptide having one or more residue differences at residue positions selected from X23, X30, X37, X40, X54, X73, X85, X130, X132, X134, X161, X163, X170, X172, X191, X197, X199, X200, X201, X203, X209, X269, X272, X289, X293, X297, X327, X330, and X334, the nitrilase amino acid sequence can include additionally one or more residue differences as compared to SEQ ID NO:2 at residue positions selected from: X49, X55, X59, X65, X94, X121, X152, X171, X173, X217, X225, X233, X240, X267, X282, X288, X295, X303, X317, X319, X323, and X332. In some embodiments, the amino acid residue at the residue positions is selected from: X49 is V; X55 is F; X65 is T; X121 is K; X152 is T; X171 is R; X173 is V; X217 is T; X225 is T; X233 is T; X240 is R; X267 is A; X282 is I; X288 is T; X295 is N; X303 is P; X317 is A; X319 is M; X323 is G or K; and X332 is I or S.

In some embodiments of the nitrilase with improved activity for conversion of substrate Id to the products IId' and IId", the nitrilase amino acid sequence can include additionally 1 to 40 residue differences as compared to SEQ ID NO:2 at other residue positions than those described above. In some embodiments these residue differences comprise conservative residue differences. In some embodiments, the other residue positions are selected from: X7, X10, X13, X18, X20, X62, X119, X135, X185, X195, X228, X238, X242, X249, X259, X268, X270, X273, X277, X291, X308, X318, X324, X326, X328, X329, and X333. In some embodiments, the amino acid residue at the residue positions is selected from: X7 is E; X10 is A; X13 is G; X18 is L; X20 is L; X62 is V; X119 is V; X135 is H; X185 is P; X195 is E; X228 is R; X238 is A; X242 is A or G; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

In some embodiments, the nitrilase having at least 1.1-fold improved activity relative to the activity of SEQ ID NO:2 for converting substrate Id to the products IId' and/or IId" comprises an amino acid sequence selected from SEQ ID NO: 4, 10, 14, 21, 28, 180, 184, 188, 192, 194, 196, 200, 210, 220, 222, 226, 230, 238, 266, 304, 310, and 314.

In some embodiments, the nitrilase polypeptide is capable of converting substrate Id to products IId' in enantiomeric excess of IId". In some embodiments, the nitrilase polypeptides are capable of producing IId" in at least 20% enantiomeric excess, at least 40% enantiomer excess, at least 80% enantiomeric excess, or at least 90% or more enantiomer excess of product IId".

In some embodiments, the nitrilase polypeptide capable converting substrate Id to product IId' in enantiomeric excess comprises an amino acid sequence that has one or more residue differences as compared to SEQ ID NO:2 selected from: X132 is F, X163 is G, and X230 is Y. In some embodiments, the nitrilase polypeptide capable of converting substrate Id to product IId' in enantiomeric excess comprises an amino acid sequence selected from: SEQ ID NO: 20, 24, and 206.

In some embodiments in which the substrate is Ie and the product is IIe', the nitrilase amino acid sequence has one or more residue differences as compared to SEQ ID NO:2 at residue positions selected from: X23, X30, X37, X49, X54, X65, X121, X134, X161, X163, X197; X199; X200; X201; X209; X240; X269; X293; X317; X323; X332; and X334. In some embodiments, the amino acid residue at the residue positions is selected from: X23 is T; X30 is L; X37 is T; X49 is V; X54 is M, F, V or A; X65 is T; X121 is K; X134 is A; X161 is N; X163 is G; X197 is L, M or N; X199 is F, H, C, V, T, W, P, M, A, or I; X200 is S; X201 is G; X209 is R; X240 is R; X269 is R; X293 is T; X317 is A; X323 is G; X332 is I; and X334 is I, S or L.

In some embodiments for the nitrilase polypeptide having one or more residue differences at residue positions selected from X23, X30, X37, X49, X54, X65, X121, X134, X161, X163, X197; X199; X200; X201; X209; X240; X269; X293; X317; X323; X332; and X334, the nitrilase amino acid sequence can include additionally one or more residue differences as compared to SEQ ID NO:2 at residue positions selected from: X40, X55, X59, X73, X85, X94, X130, X132, X152, X170, X171, X172, X173, X191, X203, X217, X225, X233, X267, X272, X282, X288, X289, X295, X297, X303, X319, X327, and X330. In some embodiments, the amino acid residue at the residue positions is selected from: X40 is E; X55 is F; X73 is E; X85 is R; X130 is R; X132 is F, H, M, or L; X152 is T; X170 is G; X171 is R; X172 is C; X173 is V; X191 is I, A or C; X203 is A; X217 is T; X225 is T; X233 is T; X267 is A; X272 is E; X282 is I; X288 is T; X289 is V; X295 is N; X297 is V, G, or A; X303 is P; X319 is M; X327 is V; and X330 is I.

In some embodiments of the nitrilase with improved activity for conversion of substrate Ie to the product IIe', the nitrilase amino acid sequence can include additionally 1 to 40 residue differences as compared to SEQ ID NO:2 at other residue positions than those described above. In some embodiments, these residue differences comprise conservative residue differences. In some embodiments, the other residue positions are selected from: X7, X10, X13, X18, X20, X62, X119, X135, X185, X195, X228, X238, X242, X249, X259, X268, X270, X273, X277, X291, X308, X318, X324, X326, X328, X329, and X333. In some embodiments, the amino acid residue at the residue positions is selected from: X7 is E; X10 is A; X13 is G; X18 is L; X20 is L; X62 is V; X119 is V; X135 is H; X185 is P; X195 is E; X228 is R; X238 is A; X242 is A or G; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

In some embodiments, the nitrilase having at least 1.1-fold improved activity relative to the activity of SEQ ID NO:2 for converting substrate Ie to the product IIe' comprises an amino acid sequence selected from SEQ ID NO: 4, 8, 10, 12, 14, 22, 144, 146, 148, 150, 152, 154, 156, 158, 160, 162, 164, 166, 168, 170, 172, 174, 176, 180, 182, 186, 190, 206, 216, 220, 222, 224, 226, 228, 230, 232, 234, 236, 238, 240, 242, 244, 246, 248, 250, 266, 274, 278, 282, 284, 288, 290 and 296.

In some embodiments in which the substrate is Ie and the products are IIe' and IIe", the nitrilase amino acid sequence has one or more residue differences as compared to SEQ ID NO:2 at residue positions selected from: X23, X37, X40, X49, X54, X65, X85, X121, X134, X139, X161, X163, X172, X191, X197, X199, X200, X272, X289, X293, X297, X319, X323, X332, and X334. In some embodiments, the amino acid residue at the residue positions is selected from: X23 is T; X37 is T; X40 is E; X49 is V; X54 is M, F, or V; X65 is T; X85 is R; X121 is K; X134 is A; X139 is W; X161 is N; X163 is G; X172 is C; X191 is I; X197 is L; X199 is F, C, M or A; X200 is S; X272 is E; X289 is V; X293 is T; X297 is V; X319 is M; X323 is G; X332 is I; and X334 is I.

In some embodiments for the nitrilase polypeptide having one or more residue differences at residue positions selected from X23, X37, X40, X49, X54, X65, X85, X121, X134, X161, X163, X172, X191, X197, X199, X200, X272, X289, X293, X297, X319, X323, X332 and X334, the nitrilase amino acid sequence can include additionally one or more residue differences as compared to SEQ ID NO:2 at residue positions selected from: X30, X55, X59, X73, X94, X130, X132, X152, X170, X171, X173, X201, X203, X209, X217, X225, X233, X240, X267, X269, X282, X288, X295, X303, X317, X327, and X330. In some embodiments, the amino acid residue at the residue positions is selected from: X30 is L; X55 is F; X73 is E; X130 is R; X132 is F, H, M, or L; X152 is T; X170 is G; X171 is R; X173 is V; X201 is G; X203 is A; X209 is R; X217 is T; X225 is T; X233 is T; X240 is R; X267 is A; X269 is R or P; X282 is I; X288 is T; X295 is N; X303 is P; X317 is A; X327 is V; and X330 is I.

In some embodiments of the nitrilase with improved activity for conversion of substrate Ie to the products IIe' and IIe", the nitrilase amino acid sequence can include additionally 1 to 40 residue differences as compared to SEQ ID NO:2 at other residue positions than those described above. In some embodiments these residue differences comprise conservative residue differences. In some embodiments, the other residue positions are selected from: X7, X10, X13, X18, X20, X62, X119, X135, X185, X195, X228, X238, X242, X249, X259, X268, X270, X273, X277, X291, X308, X318, X324, X326, X328, X329, and X333. In some embodiments, the amino acid residue at the residue positions is selected from: X7 is E; X10 is A; X13 is G; X18 is L; X20 is L; X62 is V; X119 is V; X135 is H; X185 is P; X195 is E; X228 is R; X238 is A; X242 is A or G; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

In some embodiments, the nitrilase having at least 1.1-fold improved activity relative to the activity of SEQ ID NO:2 for converting substrate Ie to the products IIe' and IIe" comprises an amino acid sequence selected from SEQ ID NO: 22, 24, 28, 180, 186, 200, 216, 220, 226, 230, 232, 236, 238, 248, 250, 274, 278, 282, 284, 288, 290, 296, 302, 306, 316, and 318.

In some embodiments in which the substrate is If and the product is IIf, the nitrilase amino acid sequence has a residue difference as compared to SEQ ID NO:2 at least at residue position X332. In some embodiments, the amino acid residue at residue position X332 is I.

In some embodiments for the nitrilase polypeptide having a residue differences at residue position X332, the nitrilase amino acid sequence can include additionally one or more residue differences as compared to SEQ ID NO:2 at residue positions selected from: X23, X30, X37, X40, X49, X54, X55, X59, X65, X73, X85, X94, X121, X130, X132, X134, X152, X161, X163, X170, X171, X172, X173, X191, X197, X199, X200, X201, X203, X209, X217, X225, X233, X240, X267, X269, X272, X282, X288, X289, X293, X295, X297, X303, X317, X319, X323, X327, X330, and X334. In some embodiments, the amino acid residue at the residue positions is selected from: X23 is T; X30 is L; X37 is T; X40 is E; X49 is V; X54 is V, M, F or A; X55 is F; X65 is T; X73 is E; X85 is R; X121 is K; X130 is R; X132 is F, H, M, or L; X134 is A; X152 is T; X161 is N; X163 is W, H or G; X170 is G; X171 is R; X172 is C; X173 is V; X191 is I, A or C; X197 is M, L or N; X199 is C, F, M, W, P, A, I, V, T, or H; X200 is S; X201 is G; X203 is A; X209 is R; X217 is T; X225 is T; X233 is T; X240 is R; X267 is A; X269 is R or P; X272 is E; X282 is I; X288 is T; X289 is V; X293 is T or V; X295 is N; X297 is V, G, or A; X303 is P; X317 is A; X319 is M; X323 is G or K; X327 is V; X330 is I; and X334 is S, I or A.

In some embodiments of the nitrilase with improved activity for conversion of substrate If to the product IIf, the nitrilase amino acid sequence can include additionally 1 to 40 residue differences as compared to SEQ ID NO:2 at other residue positions than those described above. In some embodiments these residue differences comprise conservative residue differences. In some embodiments, the other residue positions are selected from: X7, X10, X13, X18, X20, X62, X119, X135, X185, X195, X228, X238, X242, X249, X259, X268, X270, X273, X277, X291, X308, X318, X324, X326, X328, X329, and X333. In some embodiments, the amino acid residue at the residue positions is selected from: X7 is E; X10 is A; X13 is G; X18 is L; X20 is L; X62 is V; X119 is V; X135 is H; X185 is P; X195 is E; X228 is R; X238 is A; X242 is A or G; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

In some embodiments, the nitrilase having at least 1.1-fold improved activity relative to the activity of SEQ ID NO:2 for converting substrate If to the product IIf comprises an amino acid sequence selected from SEQ ID NO: 32, 36, 40, 44, 52, 154.

In some embodiments in which the substrate is Ig and the product is IIg, the nitrilase amino acid sequence has one or more residue differences as compared to SEQ ID NO:2 at residue positions selected from: X30, X49, X54, X121, X161, X191, X199, X225, X293, X332, and X334. In some embodiments, the amino acid residue at the residue positions is selected from: X30 is L; X49 is V; X54 is F, V, A, or M; X121 is K; X161 is N; X191 is I; X199 is M; X225 is T; X293 is T; X332 is I; and X334 is S, L or I.

In some embodiments for the nitrilase polypeptide having one or more residue differences at residue positions selected from X30, X49, X54, X121, X161, X191, X199, X225, X293, X332, and X334, the nitrilase amino acid sequence can include additionally one or more residue differences as compared to SEQ ID NO:2 at residue positions selected from: X23, X37, X40, X55, X59, X65, X73, X85, X94, X130, X132, X134, X152, X163, X170, X171, X172, X173, X197, X200, X201, X203, X209, X217, X233, X240, X267, X269, X272, X282, X288, X289, X295, X297, X303, X317, X319, X323, X327, and X330. In some embodiments, the amino acid residue at the residue positions is selected from: X23 is T; X37 is T; X40 is E; X55 is F; X65 is T; X73 is E; X85 is R; X130 is R; X132 is F, H, M, or L; X134 is A; X152 is T; X163 is W, H or G; X170 is G; X171 is R; X172 is C; X173 is V; X197 is M, L or N; X200 is S; X201 is G; X203 is A; X209 is R; X217 is T; X233 is T; X240 is R; X267 is A; X269 is R or P; X272 is E; X282 is I; X288 is T; X289 is V; X295 is N; X297 is V, G, or A; X303 is P; X317 is A; X319 is M; X323 is G or K; X327 is V; and X330 is I.

In some embodiments of the nitrilase with improved activity for conversion of substrate Ig to the product IIg, the nitrilase amino acid sequence can include additionally 1 to 40 residue differences as compared to SEQ ID NO:2 at other residue positions than those described above. In some embodiments these residue differences comprise conservative residue differences. In some embodiments, the other residue positions are selected from: X7, X10, X13, X18, X20, X62, X119, X135, X185, X195, X228, X238, X242, X249, X259, X268, X270, X273, X277, X291, X308, X318, X324, X326, X328, X329, and X333. In some embodiments, the amino acid residue at the residue positions is selected from: X7 is E; X10 is A; X13 is G; X18 is L; X20 is L; X62 is V; X119 is V; X135 is H; X185 is P; X195 is E; X228 is R; X238 is A; X242 is A or G; X249 is E or V; X259 is I; X268 is K;

X270 is P; X273 is A; X277 is L; X291 is E; X308 is P or R; X318 is Y; X324 is N; X326 is Y; X328 is P; X329 is I; and X333 is A.

In some embodiments, the nitrilase having at least 1.1-fold improved activity relative to the activity of SEQ ID NO:2 for converting substrate Ig to the product IIg comprises an amino acid sequence selected from SEQ ID NO: 4, 14, 22, 28, 180, 184, 188, 192, 194, 196, 200, 210, 220, 222, 226, 230, 238, 266, 304, 310 and 314.

In some embodiments in which the substrate is Ih and the product is IIh, the nitrilase amino acid sequence has one or more residue differences as compared to SEQ ID NO:2 at residue positions selected from: X23, X30, X54, X55, X152, X172, X173, X191, X200, X203, X282, X293, X295, X297, X303, X317, X323, and X332. In some embodiments, the amino acid residue at the residue positions is selected from: X23 is T; X30 is L; X54 is Y; X55 is F; X152 is T; X172 is C; X173 is V; X191 is F; X200 is S; X203 is A; X282 is I; X293 is T; X295 is N; X297 is V; X303 is P; X317 is A; X323 is K; and X332 is S.

In some embodiments for the nitrilase polypeptide having one or more residue differences at residue positions selected from X23, X30, X54, X55, X152, X172, X173, X191, X200, X203, X282, X293, X295, X297, X303, X317, X323, and X332, the nitrilase amino acid sequence can include additionally one or more residue differences as compared to SEQ ID NO:2 at residue positions selected from: X37, X40, X49, X59, X65, X73, X85, X94, X121, X130, X132, X134, X161, X163, X170, X171, X197, X199, X201, X209, X217, X225, X233, X240, X267, X269, X272, X288, X289, X319, X327, X330, and X334. In some embodiments, the amino acid residue at the residue positions is selected from: X37 is T; X40 is E; X49 is V; X65 is T; X73 is E; X85 is R; X121 is K; X130 is R; X132 is F, H, M, or L; X134 is A; X161 is N; X163 is W, H or G; X170 is G; X171 is R; X197 is M, L or N; X199 is C, F, M, W, P, A, I, V, T, or H; X201 is G; X209 is R; X217 is T; X225 is T; X233 is T; X240 is R; X267 is A; X269 is R or P; X272 is E; X288 is T; X289 is V; X319 is M; X327 is V; X330 is I; and X334 is S, I or A.

In some embodiments of the nitrilase with improved activity for conversion of substrate Ih to the product IIh, the nitrilase amino acid sequence can include additionally 1 to 40 residue differences as compared to SEQ ID NO:2 at other residue positions than those described above. In some embodiments these residue differences comprise conservative residue differences. In some embodiments, the other residue positions are selected from: X7, X10, X13, X18, X20, X62, X119, X135, X185, X195, X228, X238, X242, X249, X259, X268, X270, X273, X277, X291, X308, X318, X324, X326, X328, X329, and X333. In some embodiments, the amino acid residue at the residue positions is selected from: X7 is E; X10 is A; X13 is G; X18 is L; X20 is L; X62 is V; X119 is V; X135 is H; X185 is P; X195 is E; X228 is R; X238 is A; X242 is A or G; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

In some embodiments, the nitrilase having at least 1.1-fold improved activity relative to the activity of SEQ ID NO:2 for converting substrate Ih to the product IIh comprises an amino acid sequence selected from SEQ ID NO: 322, 324, 326, 342, 328, 330, 332, 334, 336, 344, 346, 338, 348, 350, 340, 352, 354 and 356.

In some embodiments in which the substrate is Ii and the product is IIi, the nitrilase amino acid sequence has one or more residue differences as compared to SEQ ID NO:2 at residue positions selected from: X23, X37, X49, X54, X131, X134, X161, X163, X199, X200, X240, X288, X293, and X297. In some embodiments, the amino acid residue at the residue positions is selected from: X23 is T; X37 is T; X49 is V; X54 is A, V, M or F; X131 is K; X134 is A; X161 is N; X163 is G; X199 is M, C or F; X200 is S; X240 is R; X288 is T; X293 is T; and X297 is V.

In some embodiments for the nitrilase polypeptide having one or more residue differences at residue positions selected from X23, X37, X49, X54, X134, X161, X163, X199, X200, X240, X288, X293, and X297, the nitrilase amino acid sequence can include additionally one or more residue differences as compared to SEQ ID NO:2 at residue positions selected from: X30, X40, X55, X59, X65, X73, X85, X94, X121, X130, X132, X152, X170, X171, X172, X173, X191, X197, X201, X203, X209, X217, X225, X233, X267, X269, X272, X282, X289, X295, X303, X317, X319, X323, X327, X330, X332, and X334. In some embodiments, the amino acid residue at the residue positions is selected from: X30 is L; X40 is E; X55 is F; X65 is T; X73 is E; X85 is R; X121 is K; X130 is R; X132 is F, H, M, or L; X152 is T; X170 is G; X171 is R; X172 is C; X173 is V; X191 is I, A or C; X197 is M, L or N; X201 is G; X203 is A; X209 is R; X217 is T; X225 is T; X233 is T; X267 is A; X269 is R or P; X272 is E; X282 is I; X289 is V; X295 is N; X303 is P; X317 is A; X319 is M; X323 is G or K; X327 is V; X330 is I; X332 is I or S; and X334 is S, I or A.

In some embodiments of the nitrilase with improved activity for conversion of substrate Ii to the product IIi, the nitrilase amino acid sequence can include additionally 1 to 40 residue differences as compared to SEQ ID NO:2 at other residue positions than those described above. In some embodiments these residue differences comprise conservative residue differences. In some embodiments, the other residue positions are selected from: X7, X10, X13, X18, X20, X62, X119, X135, X185, X195, X228, X238, X242, X249, X259, X268, X270, X273, X277, X291, X308, X318, X324, X326, X328, X329, and X333. In some embodiments, the amino acid residue at the residue positions is selected from: X7 is E; X10 is A; X13 is G; X18 is L; X20 is L; X62 is V; X119 is V; X135 is H; X185 is P; X195 is E; X228 is R; X238 is A; X242 is A or G; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

In some embodiments, the nitrilase having at least 1.1-fold improved activity relative to the activity of SEQ ID NO:2 for converting substrate Ii to the product IIi comprises an amino acid sequence selected from SEQ ID NO: 180, 220, 226, 228, 230, 232, 234, 236, 238, 240, 242, 244, 246, 248, 266, 274, 278, 282, and 284.

In some embodiments in which the substrate is Ij and the product is IIj, the nitrilase amino acid sequence has one or more residue differences as compared to SEQ ID NO:2 at residue positions selected from: X119, X161, X163, X199, and X242. In some embodiments, the amino acid residue at the residue positions is selected from: X119 is V; X161 is N; X163 is G; X199 is A; and X242 is A.

In some embodiments for the nitrilase polypeptide having one or more residue differences at residue positions selected from X119, X161, X163, X199, and X242, the nitrilase amino acid sequence can include additionally one or more residue differences as compared to SEQ ID NO:2 at residue positions selected from: X23; X30; X37; X40; X49; X54; X55; X59; X65; X73; X85; X94; X121; X130; X132; X134; X152; X170; X171; X172; X173; X191; X197; X200; X201; X203; X209; X217; X225; X233; X240; X267; X269; X272; X282; X288; X289; X293; X295; X297; X303; X317; X319; X323; X327; X330; X332; and X334. In some embodiments, the amino acid residue at the residue positions is selected from: X23 is T; X30 is L; X37 is T; X40 is E; X49 is V; X54 is V, M, F or A; X55 is F; X65 is T; X73 is E; X85 is R; X121 is K; X130 is R; X132 is F, H, M, or L; X134 is A; X152 is T; X170 is G; X171 is R; X172 is C; X173 is V; X191 is I, A or C; X197 is M, L or N; X200 is S; X201 is G; X203 is A; X209 is R; X217 is T; X225 is T; X233 is T; X240 is R; X267 is A; X269 is R or P; X272 is E; X282 is I; X288 is T; X289 is V; X293 is T or V; X295 is N; X297 is V, G, or A; X303 is P; X317 is A; X319 is M; X323 is G or K; X327 is V; X330 is I; X332 is I or S; and X334 is S, I or A.

In some embodiments of the nitrilase with improved activity for conversion of substrate Ij to the product IIj, the nitrilase amino acid sequence can include additionally 1 to 40 residue differences as compared to SEQ ID NO:2 at other residue positions than those described above. In some embodiments these residue differences comprise conservative residue differences. In some embodiments, the other residue positions are selected from: X7, X10, X13, X18, X20, X62, X135, X185, X195, X228, X238, X249, X259, X268, X270, X273, X277, X291, X308, X318, X324, X326, X328, X329, and X333. In some embodiments, the amino acid residue at the residue positions is selected from: X7 is E; X10 is A; X13 is G; X18 is L; X20 is L; X62 is V; X119 is V; X135 is H; X185 is P; X195 is E; X228 is R; X238 is A; X242 is A or G; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

In some embodiments, the nitrilase having at least 1.1-fold improved activity relative to the activity of SEQ ID NO:2 for converting substrate Ij to the product IIj comprises an amino acid sequence selected from SEQ ID NO: 46, 50, 52, 56 and 60.

In some embodiments, the nitrilase polypeptides are capable of converting the substrate of formula Ik:

(Ik)

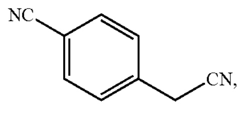

to the product of formula IIk':

(IIk')

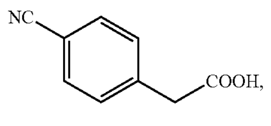

and IIk":

(IIk")

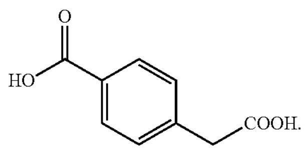

wherein the nitrilase amino acid sequence has one or more residue differences as compared to SEQ ID NO:2 at residue positions selected from: X54, X163, X191, and X242. In some of these embodiments, the amino acid residue at the residue positions are selected from: X54 is M; X163 is G; X191 is I and X242 is A.

In some embodiments, the nitrilase capable of converting substrate Ik to the product IIk comprises an amino acid sequence selected from SEQ ID NO: 30, 36, 46 or 56.

In some embodiments, the nitrilase polypeptide is capable of converting the substrate of structural formula (I) to the product of structural formula (II) in which the nitrilase has at least 10-fold improved stability as compared to SEQ ID NO:2 to the condition of 3 hrs at 40° C. In some embodiments, the nitrilase polypeptide with at least 10 fold improved thermostability comprises an amino acid sequence selected from SEQ ID NO: 5, 83, or 361.

In some embodiments, the nitrilase polypeptide is capable of converting the substrate of structural formula (I) to the product of structural formula (II) in which the nitrilase has at least 10-fold improved stability as compared to SEQ ID NO:2 to the condition of 3 hrs in 10% methanol. In some embodiments, the nitrilase polypeptide with at least 10 fold improved solvent stability comprises an amino acid sequence selected from SEQ ID NO: 5, 83, or 361.

In some embodiments, the improved engineered nitrilase polypeptides can comprise deletions of the engineered nitrilase polypeptides described herein. Thus, for each and every embodiment of the nitrilase polypeptides of the disclosure, the deletions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the nitrilase polypeptides, as long as the functional activity of the nitrilase activity is maintained. In some embodiments, the deletions can comprise, 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, or 1-40 amino acid residues. In some embodiments, the number of deletions can be 1, 2, 3, 4, 5, 6, 7, 8, 9, 10, 11, 12, 14, 15, 16, 18, 20, 22, 24, 26, 30, 35, or 40 amino acid residues. In some embodiments, the deletions can comprise deletions of 1, 2, 3, 4, 5, 6, 7, 8, 9, 10, 11, 12, 13, 14, 15, 16, 18, or 20 amino acid residues.

The polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereoisomers of the genetically-encoded amino acids; 2,3-diaminopropionic acid (Dpr); α-aminoisobutyric acid (Aib); ϵ-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutamic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisoleucine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, *CRC Practical Handbook of Biochemistry and Molecular Biology*, CRC Press, Boca Raton, Fla., at pp. 3-70 and the references cited therein, all of which are incorporated by reference). These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys (methylbenzyl), Cys (nitropyridinesulfenyl), Glu(δ-benzylester), Gln(xanthyl), Asn(N-δ-xanthyl), His(bom), His(benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

As described above, the various modifications introduced into the naturally occurring polypeptide to generate an engineered nitrilase enzyme can be targeted to a specific property of the enzyme.

5.4 Polynucleotides Encoding Nitrilases

In another aspect, the present disclosure provides polynucleotides encoding the improved nitrilase polypeptides. The polynucleotides may be operatively linked to one or more heterologous regulatory sequences that control gene expression to create a recombinant polynucleotide capable of expressing the nitrilase polypeptide. Expression constructs containing a heterologous polynucleotide encoding the engineered nitrilase can be introduced into appropriate host cells to express the corresponding nitrilase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved nitrilase polypeptides disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein, including the amino acid sequences presented in Table 2.

In some embodiments, the polynucleotides can be selected and/or engineered to comprise codons that are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. Since not all codons need to be replaced to optimize the codon usage of the nitrilases (e.g., because the natural sequence can have preferred codons and because use of preferred codons may not be required for all amino acid residues), codon optimized polynucleotides encoding the nitrilase polypeptides may contain preferred codons at about 40%, 50%, 60%, 70%, 80%, or greater than 90% of codon positions of the full length coding region.

In some embodiments, the polynucleotide encodes a nitrilase polypeptide comprising an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:2, wherein the polypeptide is capable of converting the substrate of formula I to the product of formula II, or any of the specific substrates Ia to Ik and corresponding products IIa to IIk described above, with improved stability to the condition of 3 hrs at 40° C. and/or to the condition of 3 hrs in 10% methanol.

In some embodiments, the polynucleotide encodes a nitrilase polypeptide comprising an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:2, wherein the polypeptide is capable of converting the substrate of formula I to the product of formula II, or any of the specific substrates Ia to Ik and corresponding products IIa to IIk described above, with at least 1.1 fold the activity relative to the activity of SEQ ID NO:2.

In some embodiments, the polynucleotide encodes a nitrilase polypeptide comprising an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:2, wherein the polypeptide is capable of converting the substrate of formula I to the product of formula II, or any of the specific substrates Ia to Ik and corresponding products IIa to IIk described above, with at least 1.1 fold the activity relative to the activity of SEQ ID NO:2 and improved stability to 3 hrs in 10% methanol and/or 3 hrs at 40° C.

In some embodiments, the polynucleotide encodes a nitrilase polypeptide comprising an amino acid sequence that is at least about 80%, 85%, 86%, 87%, 88%, 89%, 90%, 91%, 92%, 93%, 94%, 95%, 96%, 97%, 98%, or 99% or more identical to an amino acid sequence corresponding to SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, and 372, wherein the nitrilase polypeptide is capable of converting the substrate of structural formula (I) to the product of structural formula (II), or any of the specific substrates Ia to Ik and corresponding products IIa to IIk described above, and has (a) improved thermo- and/or solvent stability as compared to the polypeptide of SEQ ID NO:2, (b) improved activity relative to the activity of SEQ ID NO:2, or (c) a combination of improved thermo- and/or solvent stability and improved activity relative to the activity of SEQ ID NO:2.

In some embodiments, the polynucleotide encodes a nitrilase polypeptide comprising an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid sequence corresponding to SEQ ID NO: 6, 84, 122, 130, 138, 358, 360, or 362, wherein the polypeptide is capable of converting the substrate of structural formula (I) to the product of structural formula (II), or any of the specific substrates Ia to Ik and corresponding products IIa to IIk described above, and has (a) improved thermo- and/or solvent stability as compared to the polypeptide of SEQ ID NO:2, (b) improved activity relative to the activity of SEQ ID NO:2, or (c) a combination of improved thermo- and/or solvent stability and improved activity relative to the activity of SEQ ID NO:2.

In some embodiments, the polynucleotide encodes a nitrilase polypeptide comprising an amino acid sequence that is at least about 80%, 85%, 86%, 87%, 88%, 89%, 90%, 91%, 92%, 93%, 94%, 95%, 96%, 97%, 98%, or 99% identical to a reference sequence based on SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, and 372, with the proviso that the improved nitrilase amino acid sequence comprises any one of the set of residue differences contained in any one of the polypeptide sequences listed in Table 2 as compared to SEQ ID NO:2.

In some embodiments, the polynucleotides encoding the nitrilase polypeptides are selected from SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, and 371.

In some embodiments, the polynucleotides are capable of hybridizing under highly stringent conditions to a polynucleotide comprising SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, and 371, or a complement thereof, where the highly stringently hybridizing polynucleotide encodes a nitrilase polypeptide capable of converting the substrate of formula I to the product of formula II, or any of the specific substrates Ia to Ik and corresponding products IIa to IIk described above, and has (a) improved thermo- and/or solvent stability as compared to the polypeptide of SEQ ID NO:2, (b) improved activity relative to the activity of SEQ ID NO:2, or (c) a combination of improved thermo- and/or solvent stability and improved activity relative to SEQ ID NO:2.

In some embodiments, the polynucleotides encode the polypeptides described herein but have about 80% or more sequence identity, about 80%, 85%, 86%, 87%, 88%, 89%, 90%, 91%, 92%, 93%, 94%, 95%, 96%, 97%, 98%, or 99% or more sequence identity at the nucleotide level to a reference polynucleotide encoding the nitrilase polypeptides described herein, wherein the polynucleotide encodes a nitrilase polypeptide capable of converting the substrate of formula I to the product of formula II, or any of the specific substrates Ia to Ik and corresponding products IIa to IIk described above, and has (a) improved thermo- and/or solvent stability as compared to the polypeptide of SEQ ID NO:2, (b) improved activity relative to the activity of SEQ ID NO:2, or (c) a combination of improved thermo- and/or solvent stability and improved activity relative to SEQ ID NO:2. In some embodiments, the reference polynucleotide is selected from SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, and 371.

An isolated polynucleotide encoding an improved nitrilase polypeptide may be manipulated in a variety of ways to provide for expression of the polypeptide. In some embodiments, the polynucleotides encoding the engineered nitrilase polypeptides can be provided as expression vectors where one or more control sequences is present to regulate the expression of the polynucleotides. Control sequences useful with polynucleotides of the present disclosure including among others, promoters, leader sequences, polyadenylation sequences, propeptide sequences, signal peptide sequences, and transcription terminators, are well known in the art of polynucleotide recombination and expression. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, Molecular Cloning: A Laboratory Manual, 3rd Ed., Cold Spring Harbor Laboratory Press; and Current Protocols in Molecular Biology, Ausubel. F. ed., Greene Pub. Associates, 1998, updates to 2006.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

In some embodiments, the present disclosure provides a recombinant expression vector comprising a polynucleotide encoding an engineered nitrilase polypeptide or a variant thereof, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present disclosure may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated.

The expression vector of the present invention preferably contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Expression vectors for use in the present invention are well known in the art, including, among others, expression vectors pBluescriptII SK(−), pBK-CMV, pUC vectors, pREP4, pCEP4 (Invitrogen) or pPoly (Lathe et al., 1987, Gene 57:193-201).

In another aspect, the present disclosure provides a host cell comprising a polynucleotide encoding an improved nitrilase polypeptide of the present disclosure, the polynucleotide being operatively linked to one or more control sequences for expression of the nitrilase enzyme in the host cell. Host cells for use in expressing the nitrilase polypeptides encoded by the expression vectors of the present invention are well known in the art and include but are not limited to, bacterial cells, such as *E. coli, Lactobacillus, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture mediums and growth conditions for the above-described host cells are well known in the art. An exemplary host cell is *Escherichia coli* W3110.

Polynucleotides for expression of the nitrilase may be introduced into cells by various methods known in the art. Techniques include among others, electroporation, biolistic particle bombardment, liposome mediated transfection, calcium chloride transfection, and protoplast fusion. Various methods for introducing polynucleotides into cells will be apparent to the skilled artisan.

The improved nitrilases and polynucleotides encoding such polypeptides can be prepared using methods commonly used by those skilled in the art. As noted above, the naturally-occurring amino acid sequence and corresponding polynucleotide encoding the nitrilase enzyme of *Bradyrhizobium japonicum* (represented herein as SEQ ID NO:2) used as the backbone for obtaining the engineered nitrilases is available at Genbank Accession No. NP_773042.1 and NC_004463, which is hereby incorporated by reference herein. In some embodiments, the parent polynucleotide sequence is codon optimized to enhance expression of the nitrilase in a specified host cell. The polynucleotide sequence designated SEQ ID NO: 1 was the parent sequence utilized as the starting point for most experiments and library construction of engineered nitrilases.

The engineered nitrilases can be obtained by subjecting the polynucleotide encoding the naturally occurring nitrilase to mutagenesis and/or directed evolution methods. An exemplary directed evolution technique is mutagenesis and/or DNA shuffling as described in Stemmer, 1994, Proc Natl Acad Sci USA 91:10747-10751; WO 95/22625; WO 97/0078; WO 97/35966; WO 98/27230; WO 00/42651; WO 01/75767 and U.S. Pat. No. 6,537,746 (each of which is hereby incorporated by reference herein).

Other directed evolution procedures that can be used include, among others, staggered extension process (StEP), in vitro recombination (Zhao et al., 1998, Nat. Biotechnol. 16:258-261), mutagenic PCR (Caldwell et al., 1994, PCR Methods Appl. 3:S136-S140), and cassette mutagenesis (Black et al., 1996, Proc Natl Acad Sci USA 93:3525-3529). Mutagenesis and directed evolution techniques useful for the purposes herein are also described in the following references: Ling, et al., 1997, "Approaches to DNA mutagenesis: an overview," Anal. Biochem. 254(2):157-78; Dale et al., 1996, "Oligonucleotide-directed random mutagenesis using the phosphorothioate method," Methods Mol. Biol. 57:369-74; Smith, 1985, "In vitro mutagenesis," Ann. Rev. Genet. 19:423-462; Botstein et al., 1985, "Strategies and applications of in vitro mutagenesis," Science 229:1193-1201; Carter, 1986, "Site-directed mutagenesis," Biochem. J. 237: 1-7; Kramer et al., 1984, "Point Mismatch Repair," Cell 38:879-887; Wells et al., 1985, "Cassette mutagenesis: an efficient method for generation of multiple mutations at defined sites," Gene 34:315-323; Minshull et al., 1999, "Protein evolution by molecular breeding," Curr Opin Chem Biol 3:284-290; Christians et al., 1999, "Directed evolution of thymidine kinase for AZT phosphorylation using DNA family shuffling," Nature Biotech 17:259-264; Crameri et al., 1998, "DNA shuffling of a family of genes from diverse species accelerates directed evolution," Nature 391:288-291; Crameri et al., 1997, "Molecular evolution of an arsenate detoxification pathway by DNA shuffling," Nature Biotech 15:436-438; Zhang et al., 1997, "Directed evolution of an effective fructosidase from a galactosidase by DNA shuffling and screening," Proc Natl Acad Sci USA 94:45-4-4509; Crameri et al., 1996, "Improved green fluorescent protein by molecular evolution using DNA shuffling," Nature Biotech 14:315-319; and Stemmer, 1994, "Rapid evolution of a protein in vitro by DNA shuffling," Nature 370:389-391. All publications are incorporated herein by reference.

In some embodiments, the clones obtained following mutagenesis treatment are screened for nitrilases having a desired improved enzyme property. Measuring nitrilase enzyme activity from the expression libraries can be performed using the standard techniques, such as separation of the product (e.g., by HPLC) and detection of the product by measuring UV absorbance of the separated substrate and products and/or by detection using tandem mass spectroscopy (e.g., MS/MS). Exemplary assays are described in the Examples below. The rate of increase in desired product per unit time indicates the relative (enzymatic) activity of the nitrilase polypeptide in a fixed amount of the lysate (or a lyophilized powder made therefrom). Where the improved enzyme property desired is thermal stability, enzyme activity may be measured after subjecting the enzyme preparations to a defined temperature and measuring the amount of enzyme activity remaining after heat treatments. Similarly, where the improved enzyme property desired is solvent stability, enzyme activity may be measured after subjecting the enzyme preparations to a defined solvent condition and measuring the amount of enzyme activity remaining after solvent treatments. Clones containing a polynucleotide encoding the desired nitrilases are then isolated, sequenced to identify the nucleotide sequence changes (if any), and used to express the enzyme in a host cell.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides of the invention can be prepared by chemical synthesis using, e.g., the classical phosphoramidite method described by Beaucage et al., 1981, Tet Lett 22:1859-69, or the method described by Matthes et al., 1984, EMBO J. 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources.

The engineered nitrilase enzymes expressed in a host cell can be recovered from the cells and or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are commercially available, such as under the trade name CelLytic B™ from Sigma-Aldrich of St. Louis Mo.

Chromatographic techniques for isolation of the nitrilase polypeptide include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art. In some embodiments, the engineered nitrilases can be expressed as fusion proteins with purification tags, such as His-tags having affinity for metals, or antibody tags for binding to antibodies, e.g., myc epitope tag.

In some embodiments, affinity techniques may be used to isolate the improved nitrilase enzymes. For affinity chromatography purification, any antibody which specifically binds the nitrilase polypeptide may be used. For the production of antibodies, various host animals, including but not limited to rabbits, mice, rats, etc., may be immunized by injection with an engineered polypeptide. The polypeptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette Guerin) and *Corynebacterium parvum.*

5.5 Methods of Using Nitrilases

In another aspect, the present disclosure provides methods of using the engineered nitrilase polypeptides for converting nitriles to the corresponding carboxylic acids, and in certain embodiments, to the corresponding amides. Accordingly, in some embodiments, the nitrilases can be used in a process for converting the substrate compound of formula I to the product of formula II:

$R^1$—CN→$R^1$—COOH wherein, $R^1$ is a substituted or unsubstituted phenyl; a substituted or unsubstituted phenylalkyl($C_1$-$C_3$); a substituted or unsubstituted alkyl($C_3$-$C_8$) or a substituted or unsubstituted heteroalkyl (3-8 atoms), and in which the process comprises contacting the substrate of formula I with an engineered nitrilase described herein under suitable reaction conditions to convert the substrate to the product of formula II.

In some embodiments, the nitrilase useful in the process comprises a polypeptide that has improved stability to a condition of 3 hrs at 40° C. and/or 3 hrs in 10% methanol as compared to the polypeptide of SEQ ID NO:2.

In some embodiments, the nitrilase useful in the process comprises a nitrilase polypeptide that has at least 1.1 fold improved activity relative to the activity of SEQ ID NO:2 for converting the substrate of formula I to the product of formula II.

In some embodiments, the nitrilase polypeptide useful in the process comprises an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:2, wherein the polypeptide is capable of converting the substrate of formula I to the product of formula II, or any of the specific substrates Ia to Ik and corresponding products IIa to IIk described above, with improved stability to the condition of 3 hrs at 40° C. and/or to the condition of 3 hrs in 10% methanol.

In some embodiments, the nitrilase polypeptide useful in the process comprises an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:2, wherein the polypeptide is capable of converting the substrate of formula I to the product of formula II, or any of the specific substrates Ia to Ik and corresponding products IIa to IIk described above, with at least 1.1 fold the activity relative to the activity of SEQ ID NO:2.

In some embodiments, the nitrilase polypeptide useful in the process comprises an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:2, wherein the polypeptide is capable of converting the substrate of formula I to the product of formula II, or any of the specific substrates Ia to Ik and corresponding products IIa to IIk described above, with at least 1.1 fold the activity relative to the activity of SEQ ID NO:2 and improved stability to 3 hrs in 10% methanol and/or 3 hrs at 40° C.

In some embodiments, the nitrilase polypeptide useful in the process comprises an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid sequence corresponding to SEQ ID NO: 6, 84, 122, 130, 138, 358, 360, or 362, wherein the polypeptide is capable of converting the substrate of structural formula (I) to the product of formula (II), or any of the specific substrates Ia to Ik and corresponding products IIa to IIk described above, and has (a) improved thermo- and/or solvent stability as compared to the polypeptide of SEQ ID NO:2, (b) improved activity relative to the activity of SEQ ID NO:2, or (c) a combination of improved thermo- and/or solvent stability and improved activity relative to the activity of SEQ ID NO:2.

As described herein, in some embodiments, the nitrilase polypeptide useful in the process further comprises a fusion of the carboxy terminus of the nitrilase polypeptide to a polypeptide of SEQ ID NO: 378 or 380, or at least a contiguous segment of 17 amino acids of SEQ ID NO: 378 or 380.

In some embodiments, the nitrilase used in the process comprises an amino acid sequence selected from SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, and 372.

In some embodiments, the nitrilases can be used in a process for converting the specific substrates described herein to the corresponding products for preparation of compounds and intermediates useful in chemical synthesis. Thus, in some embodiments, the process comprises contacting the substrate Ia

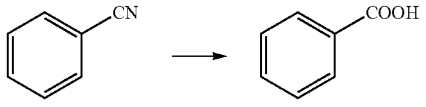

(Ia) (IIa)

with a engineered nitrilase described herein under suitable reactions conditions to convert the substrate to the product IIa.

In some embodiments, the process for converting the substrate of formula Ia to the product of formula IIa can use a nitrilase polypeptide comprising an amino acid sequence selected from: 4, 8, 10, 12, 14, 16, 18, 22, 30, 32, 34, 36, 38, 40, 42, 44, 46, 50, 52, 54, 56, 144, 150, 152, 156, 158, 160, 162, 166, 168, 170, 172, 174, 176, 206, 208, 216, and 218.

In some embodiments, the process comprises contacting the substrate Ib

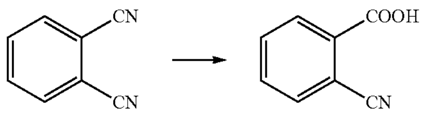

(Ib) (IIb)

with an engineered nitrilase described herein under suitable reaction conditions to convert the substrate to the product IIb.

In some embodiments, the process for converting the substrate of formula Ib to the product of formula IIb can use a nitrilase polypeptide comprising an amino acid sequence selected from: 178, 180, 190, 192, 194, 196, 198, 202, 204, 220, 222, 224, 226, 228, 232, 234, 236, 238, 240, 242, 244, 246, 248, 250, 252, 254, 256, 258, 260, 262, 264, 266, 268, 270, 272, 274, 276, 278, 282, 284, 288, 290, 292, 296, or 300.

In some embodiments, the process comprises contacting the substrate Ic:

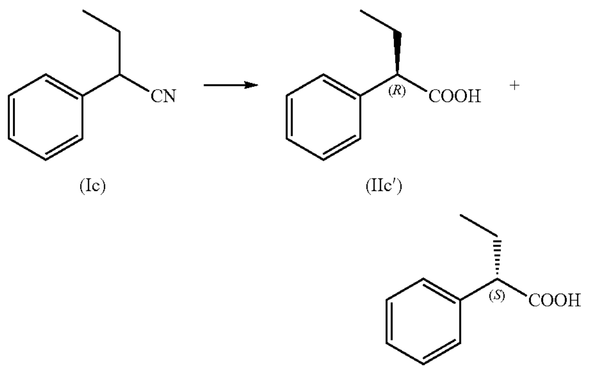

(Ic) (IIc') (IIc")

with an engineered nitrilase described herein under suitable reaction conditions to convert the substrate to the products IIc' and IIc".

In some embodiments, the process for converting the substrate of formula Ic to the product of formulas IIc' and IIc" can use a nitrilase polypeptide comprising an amino acid sequence selected from: 4, 8, 10, 14, 20, 24, 28, 42, 44, 54, 154, 174, 210, 212, 214, 250, 256, 270, 276, 284, 288, 298, 300, 302, 304, 308, 310, 312, 316, and 318.

In some embodiments, the process comprises contacting the substrate Id:

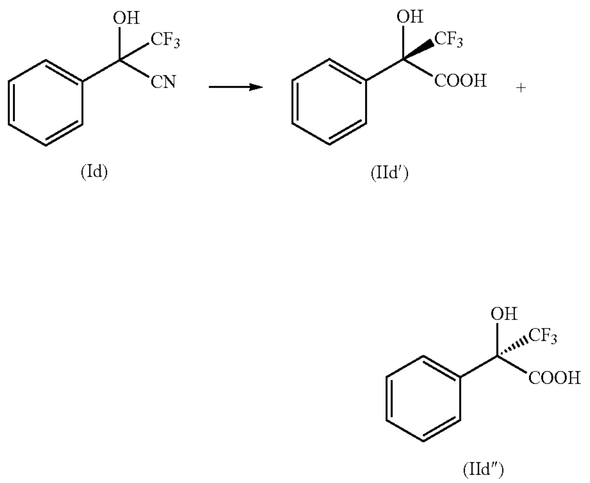

(Id) (IId') (IId")

with an engineered nitrilase described herein under suitable reaction conditions to convert the substrate to the products IId' and IId".

In some embodiments, the process for converting the substrate of formula Id to the products of formulas IId' and IId" can use a nitrilase polypeptide comprising an amino acid sequence selected from: 4, 10, 14, 21, 28, 180, 184, 188, 192, 194, 196, 200, 210, 220, 222, 226, 230, 238, 266, 304, 310, and 314.

In some embodiments, the process comprises contacting the substrate Ie:

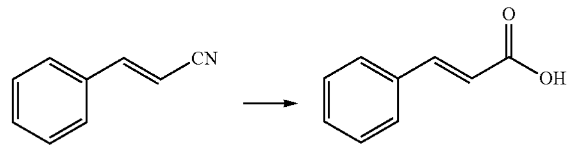

(Ie) (IIe')

with an engineered nitrilase described herein under suitable reaction conditions to convert the substrate to the product IIe'.

In some embodiments, the process for converting the substrate of formula Ie to the product of formula IIe' can use a nitrilase polypeptide comprising an amino acid sequence selected from: 4, 8, 10, 12, 14, 22, 144, 146, 148, 150, 152, 154, 156, 158, 160, 162, 164, 166, 168, 170, 172, 174, 176, 180, 182, 186, 190, 206, 216, 220, 222, 224, 226, 228, 230, 232, 234, 236, 238, 240, 242, 244, 246, 248, 250, 266, 274, 278, 282, 284, 288, 290 and 296.

In some embodiments, the process comprises contacting the substrate Ie:

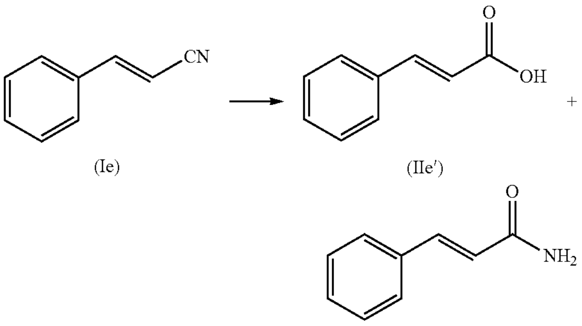

(Ie) (IIe') (IIe")

with an engineered nitrilase described herein under suitable reaction conditions to convert the substrate to the products IIe' and IIe".

In some embodiments, the process for converting the substrate of formula Ie to the product of formulas IIe' and IIe" can use a nitrilase polypeptide comprising an amino acid sequence selected from: 22, 24, 28, 180, 186, 200, 216, 220, 226, 230, 232, 236, 238, 248, 250, 274, 278, 282, 284, 288, 290, 296, 302, 306, 316, and 318.

In some embodiments, the process comprises contacting the substrate If:

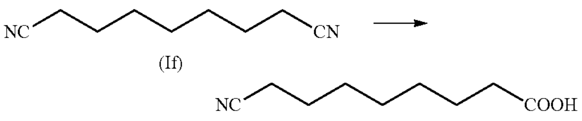

(If) (IIf)

with an engineered nitrilase described herein under suitable reaction conditions to convert the substrate to the product IIf.

In some embodiments, the process for converting the substrate of formula If to the product of formula IIf can use a nitrilase polypeptide comprising an amino acid sequence selected from: 32, 36, 40, 44, 52, and 154.

In some embodiments, the process comprises contacting the substrate Ig:

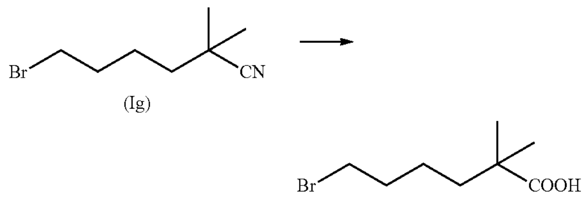

(Ig) (IIg)

with an engineered nitrilase described herein under suitable reaction conditions to convert the substrate to the product IIg.

In some embodiments, the process for converting the substrate of formula Ig to the product of formula IIg can use a nitrilase polypeptide comprising an amino acid sequence selected from: 4, 14, 22, 28, 180, 184, 188, 192, 194, 196, 200, 210, 220, 222, 226, 230, 238, 266, 304, 310 and 314.

In some embodiments, the process comprises contacting the substrate Ih

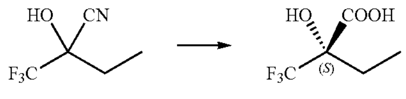

(Ih) (IIh)

with an engineered nitrilase described herein under suitable reaction conditions to convert the substrate to the product IIh.

In some embodiments, the process for converting the substrate of formula Ih to the product of formula IIh can use a nitrilase polypeptide comprising an amino acid sequence selected from: 322, 324, 326, 342, 328, 330, 332, 334, 336, 344, 346, 338, 348, 350, 340, 352, 354 and 356.

In some embodiments, the process comprises contacting the substrate Ii

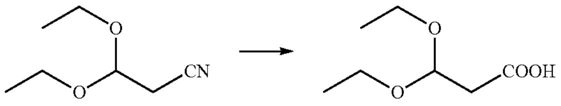

(Ii) (IIi)

with an engineered nitrilase described herein under suitable reaction conditions to convert the substrate to the product IIi.

In some embodiments, the process for converting the substrate of formula II to the product of formula IIi can use a nitrilase polypeptide comprising an amino acid sequence selected from: 180, 220, 226, 228, 230, 232, 234, 236, 238, 240, 242, 244, 246, 248, 266, 274, 278, 282, and 284.

In some embodiments, the process comprises contacting the substrate Ij:

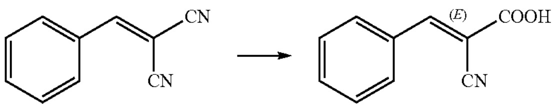

(Ij) (IIj)

with an engineered nitrilase described herein under suitable reaction conditions to convert the substrate to the product IIj.

In some embodiments, the process for converting the substrate of formula Ij to the product of formula IIj can use a nitrilase polypeptide comprising an amino acid sequence selected from: 46, 50, 52, 56 and 60.

In some embodiments, the nitrilases of the disclosure can be used in a process for converting a dinitrile of formula Ik to the corresponding carboxylic acid product of formula IIk' and the diacid of formula IIk". The naturally occurring nitrilase of SEQ ID NO:2 is unable to carry out a reaction that forms the diacid. In these embodiments, the process for converting the substrate of formula Ik to the products of formulas IIk' and IIk":

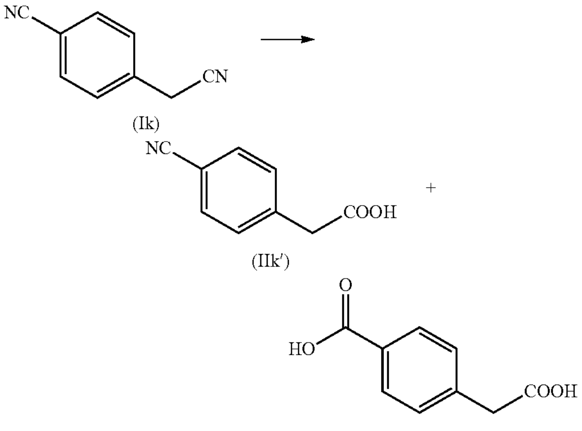

(Ik) (IIk') + (IIk")

can comprise contacting the substrate with an engineered nitrilase described herein under suitable reaction conditions to convert the substrate to the products IIk' and IIk".

In some embodiments, the process for converting the substrate of formula Ik to the products of formulas IIk' and IIk can use a nitrilase polypeptide comprising an amino acid sequence selected from: 30, 36, 46 or 56.

In some embodiments, the nitrilase polypeptide described herein can be provided in the form of kits. The enzymes in the kits may be present individually or as a plurality of enzymes. In some embodiments, the nitrilase enzymes can be provided on a substrate. In some embodiments, the nitrilase enzymes can be provided in the form of an array. The array can be used to test a variety of nitrile compounds for conversion by the nitrilases. "Substrate," "support," "solid support," "solid carrier," or "resin" in the context of arrays refer to any solid phase material. Substrate also encompasses terms such as "solid phase," "surface," and/or "membrane." A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of a substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments.

"Array" refers to an arrangement of agents (e.g., nitrilases polypeptides) on a substrate in positionally distinct locations. Such arrays may be constructed on planar objects such as glass or plastic microscope slides. Arrays may also be constructed on the inside surface of a tube or microplate well or may be constructed inside the channels of a microfluidic device.

In certain embodiments, the kits of the present disclosure include arrays comprising a plurality of different engineered nitrilase polypeptides at different addressable position, wherein the different engineered nitrilase polypeptides are different variants of a reference sequence each having at least one different improved enzyme property. In certain embodiments, each different polypeptide has a different substrate activity and/or substrate preference. For example, each different engineered nitrilase polypeptide in the plurality on the addressable array can have a different set of residue differences such that each has an improved activity with a different substrate or set of substrates. Such arrays comprising a plurality of engineered polypeptides and methods of their use are described in, e.g., WO2009/008908A2.

The kits can further include reagents for carrying out the enzymatic reactions, substrates for assessing the activity of enzymes, as well as reagents for detecting the products. The kits can also include reagent dispensers and instructions for use of the kits.

Various features and embodiments of the disclosure are illustrated in the following representative examples, which are intended to be illustrative, and not limiting.

6. EXAMPLES

Example 1

Nitrilase Variants with Increased Solvent Stability

This example illustrates variants of *B. japonicum* nitrilase having increased stability upon exposure to solvent or increased temperature relative to the *B. japonicum* wild-type nitrilase (encoded by SEQ ID NO: 1) exposed to the same solvent conditions. Solvent stability was determined by screening variant activity in an assay of the nonanedinitrile (AZN) substrate with nitrilase as shown below:

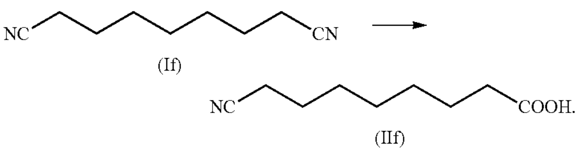

(If)

(IIf)

Pre-Incubation Conditions:

A mixture of 50 µL lysate containing variant enzyme and 50 µL of 100 mM sodium phosphate buffer (pH 8) was exposed for 3 h or 20 h to one or more of the additional challenge conditions. The solvent challenge conditions were selected from: 10% methanol (MeOH), 20% MeOH, 10% isopropanol (IPA), 50% v/v ethyl acetate, or 50% v/v toluene. The thermal challenge conditions were selected from: 40° C. or 50° C. Control conditions were 3 h incubation at 30° C. with no co-solvent.

Reaction with AZN:

100 µL of the pre-incubated sample was added to 300 µL reaction buffer (13.3 mM AZN in 100 mM sodium phosphate, pH 8), for 2 h at 30° C. with 250 rpm shaking.

Fluorescence Assay:

Each reaction mixture was diluted 4-fold in 100 mM sodium phosphate, pH 7.4, and then again 4-fold into fluorescence buffer (100 mM sodium phosphate, pH 7.4 containing 0.5 mg/mL phthaldialdehyde, 35 µM beta-mercaptoethanol, and 10% v/v ethanol). Fluorescence was measured at 467 nm using excitation at 412 nm. The average fluorescence of negative control wells was subtracted from each sample as background.

GC Sample Preparation:

Hydrochloric acid (50 µL of 1 M) was added to each well of a microtitre place and followed by 1 volume of ethyl acetate. Plate was sealed and shaken at 850 rpm for 10 min at room temperature. Plates were centrifuged at 2,000 rpm (3220×g) for 2 min to separate the layers. A 100 µL volume of ethyl acetate layer from each well was transferred to a shallow well plate (Costar 3365). Plates were sealed with a heat-sealer set at 170° C. for 2 sec.

GC Conditions:

Restek XTI-5 column (30 m×0.25 mm ID); 150° C. [10° C./min] to 230° C.; 8 min run time; retention times: AZN acid product: 5.9 min; nitrile: 5.4 min.

Results:

Nitrilase variants showing at least 1.1-fold improvement under the solvent or thermal challenge conductions are listed in Tables 3-5 below. Increased solvent and/or thermal stability was observed for nitrilase variants including at least one of the following mutations relative to the corresponding position in SEQ ID NO: 2: A91R, T108S, Y139F, I166L, M230V, M266L, L308R, M309L, and E325G.

TABLE 3

Variants showing at least 1.1-fold improvement in solvent (10% MeOH) and/or thermal stability (40° C.) relative to nitrilase encoded by SEQ ID NO: 1 in fluorescence assay.

| SEQ ID NO: | VARIANT AA SEQUENCE MUTATION(S) | RELATIVE IMPROVEMENT (FIOP)[1] 10% MEOH | 40° C. |
|---|---|---|---|
| 6 | A91R; T108S; Y139F; I166L; M230V; M266L; | ++++ | ++++ |
| 84 | A91R; Y139F; I166L; M230V; M309L | ++++ | ++++ |
| 104 | T108S; Y139F; E268K; L308P | + | |
| 106 | A20L; T108S; Y139F; S152T; S185P; A249E; K291E; G303P | ++ | |
| 108 | A62V ; T108S; Y139F; I166L; M266L | ++ | |
| 110 | T108S; Y139F; S152T; I166L; K195E; I277L; V282I | + | |
| 112 | A20L; Y139F; I166L | ++ | |
| 114 | T108S; Y139F; M266L; M309L | ++ | |
| 116 | V10A; M18L; S152T; I166L; L308R | ++ | |
| 118 | T108S; S152T; I166L; M266L; V282I | ++ | |
| 120 | T108S; Y139F; M266L | ++ | |
| 122 | Y139F; I166L | ++ | ++++ |
| 124 | Y139F; S152T; I166L; A249V; E268D; H269P; D273A; G303P | + | |
| 126 | T108S; Y139F; I166L; M266L; V282I; G303P; M309L | ++ | |
| 128 | Y139F; I166L; M266L; I277LV2821 | +++ | |
| 130 | I166L; M309L | ++ | ++++ |
| 132 | T108S; M266L | ++ | |
| 134 | A13G; T108S; Y139F; S152T; M266L; M309L; T317A | ++ | |
| 136 | I166F; D242G; S318Y; A328P; V329I; E333A | + | |
| 138 | Y139F; I166L; M309L | +++ | ++++ |

TABLE 3-continued

| Variants showing at least 1.1-fold improvement in solvent (10% MeOH) and/or thermal stability (40° C.) relative to nitrilase encoded by SEQ ID NO: 1 in fluorescence assay. | | | |
|---|---|---|---|
| SEQ ID NO: | VARIANT AA SEQUENCE MUTATION(S) | RELATIVE IMPROVEMENT (FIOP)[1] 10% MEOH | 40° C. |
| 140 | I166L; V282I | +++ | |
| 142 | T108S; Y139F; M266L | ++ | |
| 358 | T108S; Y139F; I166L; M266L | ++++ | ++++ |
| 360 | A91R; M230V | ++++ | ++++ |
| 362 | A91R; Y139F; I166L; M230V | ++++ | ++++ |
| 364 | A91R; Y139F; I166L; M230V; M309L | ++++ | |
| 372 | E325G | +++ | |

[1]Relative Improvement (FIOP) scale: "+" indicates 1.1 to 1.5-fold improved; "++" indicates >1.5 to 2.0-fold improved; "+++" indicates >2.0 to 2.5-fold improved; and "++++" indicates >2.5-fold improved.

TABLE 4

Variants showing improved solvent stability relative to nitrilase encoded by SEQ ID NO: 1 following up to 20 hours exposure (assayed using GC).

| | 3 HOUR EXPOSURE | | | 20 HOUR EXPOSURE | |
|---|---|---|---|---|---|
| SEQ ID NO: | 10% MEOH | 20% MEOH | 10% IPA | 10% MEOH | 20% MEOH |
| 6 | ++ | ++++ | ++++ | ++++ | ++++ |
| 84 | ++ | ++++ | ++++ | +++ | — |
| 362 | ++ | ++++ | ++++ | ++++ | + |

TABLE 5

Variants showing improved thermal stability relative to nitrilase encoded by SEQ ID NO: 1 following up 20 hours exposure (assayed using GC).

| SEQ ID | 3 HOUR EXPOSURE | | 20 HOUR EXPOSURE | |
|---|---|---|---|---|
| NO: | 40° C. | 50° C. | 40° C. | 50° C. |
| 6 | ++++ | ++++ | ++++ | ++++ |
| 84 | ++++ | ++++ | ++++ | ++++ |
| 362 | ++++ | ++++ | ++++ | ++++ |

[1]Relative Improvement (FIOP) scale: "+" indicates 1.1 to 1.5-fold improved; "++" indicates >1.5 to 2.0-fold improved; "+++" indicates >2.0 to 2.5-fold improved; and "++++" indicates >2.5-fold improved.

Example 2

Nitrilase Variants with Increased Nitrilase Activity for Substrate AZN

This example illustrates variants of *B. japonicum* nitrilase having increased nitrilase activity relative to the parent nitrilase variant encoded by SEQ ID NO: 1 in the reaction of the substrate AZN substrate (compound of formula If) to the 8-cyanooctanoic product (compound of formula IIf) as shown below:

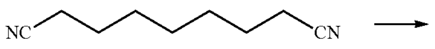

(If)

-continued

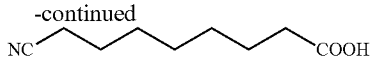

(IIf)

Reaction with AZN (Assays Relative to SEQ ID NO: 2):

The reaction mixture contained 10 mM substrate, 2% MeOH, 100 mM potassium phosphate, pH 8.0, 100 μL of 10× diluted lysate containing variant enzyme, in a total reaction volume 300 μL in reaction plate wells. Plates were shaken for 1 h at 250 rpm, 30° C.

Reaction with AZN (Assays Relative to SEQ ID NO: 6):

The reaction mixture contained 15 mM substrate, 10% MeOH, 100 mM potassium phosphate, pH 8.0, 30 μL lysates containing variant enzyme, in a total reaction volume of 300 μL in reaction plate wells. Plates were shaken for 1 h at 250 rpm, 30° C.

GC Sample Preparation:

Samples were prepared for GC analysis by adding 50 μL of 1 M hydrochloric acid to each well, followed by 1 volume of ethyl acetate. Plate was sealed and shaken at 850 rpm for 10 min at room temperature. Plate was centrifuged at 2,000 rpm (3220×g) for 2 min to separate the layers. A 100 μL volume of ethyl acetate layer from each well was transferred to a shallow well plate (Costar 3365). Plate was sealed with a heat-sealer set at 170° C. for 2 sec.

GC Conditions:

Restek XTI-5 column (30 m×0.25 mm ID); 150° C. [10° C./min] to 230° C.; 8 min run time; retention times: AZN acid product: 5.9 min; nitrile: 5.4 min.

Results:

Nitrilase variants showing at least 1.1-fold improvement are listed in Table 6 below. Increased activity with the AZN was observed for nitrilase variants including at least one of the following mutations relative to the corresponding position in SEQ ID NO: 2: W54V, W54M, W54F, L199A, M230A, and T332I.

TABLE 6

Variants showing at least 1.1-fold improvement in activity with AZN substrate relative to "parent" (FIOP) nitrilase encoded by SEQ ID NO: 2 or SEQ ID NO: 6.

| SEQ ID NO: | VARIANT AA SEQUENCE MUTATION(S) | RELATIVE IMPROVEMENT (FIOP)[1] |
|---|---|---|
| | ASSAYS RELATIVE TO SEQ ID NO: 2 | |
| 32 | W54V | ++ |
| 36 | W54M | ++ |
| 40 | W54F | ++ |
| 44 | M230A | + |
| 52 | L199A | ++ |
| | ASSAYS RELATIVE TO SEQ ID NO: 6 | |
| 154 | A91R; Y139F; I166L; M230V; M309L; T332I | + |

[1]Relative Improvement (FIOP) scale: "+" indicates 1.1 to 1.5-fold improved; "++" indicates >1.5 to 2.0-fold improved; "+++" indicates >2.0 to 2.5-fold improved; and "++++" indicates >2.5-fold improved.

Example 3

Nitrilase Variants with Increased Nitrilase Activity for Substrate BEN

This example illustrates variants of *B. japonicum* nitrilase having increased nitrilase activity relative to the parent nitrilase variant encoded by SEQ ID NO: 1 in the reaction of the substrate Ia (benzonitrile or "BEN") to form product IIa (benzoic acid) as shown below:

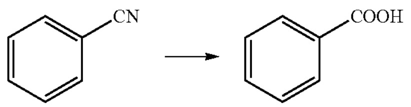

(Ia) (IIa)

Reaction with BEN (Assays Relative to SEQ ID NO: 2):

The reaction mixture contained 10 mM substrate, 2% MeOH, 100 mM potassium phosphate, pH 8.0, 50 μL lysate containing variant enzyme, in a total reaction volume of 300 μL in reaction plate wells. Plates were shaken overnight at 250 rpm, 30° C.

Reaction with BEN (Assays Relative to SEQ ID NO: 6):

The reaction mixture contained 10 mM substrate, 10% MeOH, 100 mM potassium phosphate, pH 8.0, 50 μL lysate containing variant enzyme, in a total reaction volume of 300 μL in reaction plate wells. Plates were shaken overnight at 250 rpm, 30° C.

GC Sample Preparation:

Hydrochloric acid (50 mL of 1 M) was added to each well, and followed by 1 volume of ethyl acetate. Plate was sealed and shaken at 850 rpm for 10 min at room temperature. Plates were centrifuged at 2,000 rpm (3220×g) for 2 min to separate the layers. A 100 μL volume of the ethyl acetate layer from each well was transferred to a shallow well plate (Costar 3365). Plate was sealed with a heat-sealer set at 170° C. for 2 sec.

GC Analysis Conditions:

Agilent HP-5. 180° C. isothermal 2 min; retention times: acid: 1.9 min.

Results:

Nitrilase variants showing at least 1.1-fold improvement are listed in Table 7 below. Increased activity with the BEN was observed for nitrilase variants including at least one of the following mutations relative to the corresponding position in SEQ ID NO: 2: F30L, W54A, W54F, W54M, W54V, C161N, A163H, A163W, L191A, L191C, L191I, Y197L, Y197M, Y197N, L199A, L199C, L199H, L199F, L199V, L199T, L199W, L199M, L199I, M230A, M230Y, P238A, D242A, H269R, A293T, T334I, T334S, and T334L.

TABLE 7

Variants showing at least 1.1-fold improvement in activity with BEN substrate relative to "parent" (FIOP) nitrilase encoded by SEQ ID NO: 1 or SEQ ID NO: 5.

| SEQ ID NO: | VARIANT AA SEQUENCE MUTATION(S) (C-TERMINAL AA SEQUENCE EXTENSION - WHERE PRESENT) | RELATIVE IMPROVEMENT (FIOP)[1] |
|---|---|---|
| | ASSAYS RELATIVE TO SEQ ID NO: 2 | |
| 30 | L191I | +++ |
| 32 | W54V | +++ |
| 34 | L191A | +++ |
| 36 | W54M | ++++ |
| 38 | L191C | ++ |
| 40 | W54F | +++ |
| 42 | A163W | ++++ |
| 44 | M230A | ++++ |
| 46 | D242A | ++++ |
| 50 | A163H | + |

TABLE 7-continued

Variants showing at least 1.1-fold improvement in activity with BEN substrate relative to "parent" (FIOP) nitrilase encoded by SEQ ID NO: 1 or SEQ ID NO: 5.

| SEQ ID NO: | VARIANT AA SEQUENCE MUTATION(S) (C-TERMINAL AA SEQUENCE EXTENSION - WHERE PRESENT) | RELATIVE IMPROVEMENT (FIOP)[1] |
|---|---|---|
| 52 | C161N | ++++ |
| 54 | L199A | ++ |
| 56 | P238A | +++ |
| | ASSAYS RELATIVE TO SEQ ID NO: 6 | |
| 4 | F30L; A91R; Y139F; I166L; M230V; M309L; T334S (334QTGHHQDPLQGRADGQA) | ++ |
| 8 | A91R; Y139F; I166L; M230V; A293T; M309L | ++ |
| 10 | A91R; Y139F; I166L; Y197L; M230V; M309L; T334I | + |
| 12 | A91R; Y139F; I166L; L199C; M230V; M309L | ++ |
| 14 | A91R; T108S; Y139F; I166L; M230V; M266L; T334L (334SQTGHHQDPLQGRADGQA) | ++ |
| 16 | W54F; A91R; T108S; Y139F; I166L; M230V; M266L | ++ |
| 18 | W54M; A91R; T108S; Y139F; I166L; M230V; M266L | +++ |
| 22 | A91R; T108S; Y139F; C161N; I166L; M230V; M266L | ++ |
| 144 | A91R; Y139F; I166L; Y197M; M230V; M309L | + |
| 150 | A91R; Y139F; I166L; L199H; M230V; M309L | ++ |
| 152 | A91R; Y139F; I166L; L199F; M230V; M309L | ++ |
| 156 | A91R; Y139F; I166L; L199C; M230V; M309L | ++ |
| 158 | A91R; Y139F; I166L; L199V; M230V; M309L | ++ |
| 160 | A91R; Y139F; I166L; L199T; M230V; M309L | + |
| 162 | A91R; Y139F; I166L; L199W; M230V; M309L | ++ |
| 166 | A91R; Y139F; I166L; L199M; M230V; M309L | +++ |
| 168 | A91R; Y139F; I166L; L199A; M230V; M309L | + |
| 170 | A91R; Y139F; I166L; L199I; M230V; M309L | + |
| 172 | A91R; Y139F; I166L; L199F; M230V; H269R; M309L | +++ |
| 174 | A91R; T108S; Y139F; I166L; M230V; M266L; T334I | + |
| 176 | A91R; T108S; Y139F; I166L; Y197N; M230V; M266L | ++ |
| 206 | A91R; Y139F; I166L; M230Y; M309L | + |
| 208 | W54V; A91R; T108S; Y139F; I166L; M230V; M266L | +++ |
| 216 | A91R; T108S; Y139F; I166L; L199A; M230V; M266L | + |
| 218 | W54A; A91R; T108S; Y139F; I166L; M230V; M266L | + |

[1]Relative Improvement (FIOP) scale: "+" indicates 1.1 to 1.5-fold improved; "++" indicates >1.5 to 2.0-fold improved; "+++" indicates >2.0 to 2.5-fold improved; and "++++" indicates >2.5-fold improved.

Example 4

Nitrilase Variants with Increased Nitrilase Activity for Substrate CNN

This example illustrates variants of *B. japonicum* nitrilase having increased nitrilase activity relative to the parent nitrilase variant encoded by SEQ ID NO: 6 in the reaction of the substrate (Z-3-phenylacrylonitrile or "CNN") to form the cinnamic acid or cinnamamide products (compounds of formulas IIe' and IIe" respectively) as shown below:

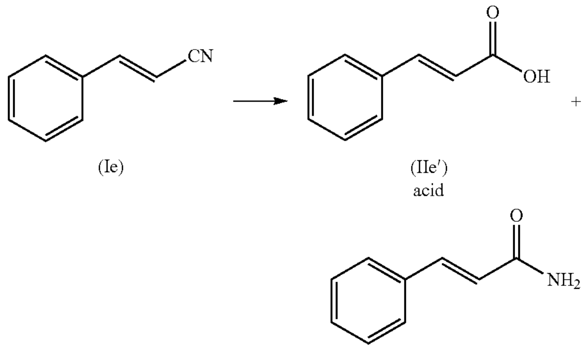

(Ie)

(IIe') acid (IIe'') amide

Reaction with CNN:

Reaction mixture contained 10 mM substrate, 10% MeOH, 100 mM potassium phosphate, pH 8.0, 100 μL lysate containing variant enzyme, in a total reaction volume of 300 μL in reaction plate wells. Plates were shaken overnight at 250 rpm and 30° C.

HPLC Sample Preparation:

For HPLC analysis, 1 volume of acetonitrile was added to each well. Plate was sealed and shaken at 850 rpm for 10 min at room temperature. Plate was centrifuged at 2,000 rpm (3220×g) for 10 min to pellet the enzyme debris. A 200 μL volume from each well was transferred to a shallow well plate (Costar 3365). Plate was sealed with heat-sealer set at 170° C. for 2 sec.

Reverse Phase HPLC Conditions:

Samples were examined by injecting 10 μL onto a Phenomenex Luna PFP(2), 5 μm (0.46 cm×250 mm) at a column temperature of 25° C. The mobile phase was 70:30:0.1 (v:v:v) acetonitrile:water:acetic acid, and had a flow-rate of 2.0 mL $min^{-1}$ for 4 min runtime. Detection was carried out at a wavelength of 300 nm. Retention times of the acid is 1.9 min while the nitrile has a retention time of 2.9 min under the chromatographic conditions.

Results:

Nitrilase variants showing at least 1.1-fold improvement for production of acid product from CNN substrate are listed in Table 8 below. Increased activity with for production of acid product from CNN substrate was observed for nitrilase variants including at least one of the following mutations relative to the corresponding position in SEQ ID NO: 2: S23T, F30L, A37T, I49V, W54M, W54F, W54V, W54A, M65T, E121K, V134A, C161N, A163G, Y197LMN, L199F, L199H, L199C, L199V, L199T, L199W, L199P, L199M, L199A, L199I, G200S, H201G, Q209R, K240R, H269R, A293T, T317A, E323G, T332I, T334I, L199S, and L199L.

TABLE 8

Variants showing at least 1.1-fold improvement in activity with CNN substrate for production of acid product relative to "parent" (FIOP) nitrilase encoded by SEQ ID NO: 6.

| SEQ ID NO: | VARIANT AA SEQUENCE MUTATION(S) (C-TERMINAL AA SEQUENCE EXTENSION - WHERE PRESENT) | RELATIVE IMPROVEMENT (FIOP)[1] |
|---|---|---|
| 4 | F30L; A91R; Y139F; I166L; M230V; M309L; T334S (334QTGHHQDPLQGRADGQA) | + |
| 8 | A91R; Y139F; I166L; M230V; A293T; M309L | + |
| 10 | A91R; Y139F; I166L; Y197L; M230V; M309L; T334I | ++++ |
| 12 | A91R; Y139F; I166L; L199C; M230V; M309L | ++++ |
| 14 | A91R; T108S; Y139F; I166L; M230V; M266L; T334L (334SQTGHHQDPLQGRADGQA) | ++ |
| 22 | A91R; T108S; Y139F; C161N; I166L; M230V; M266L | + |
| 144 | A91R; Y139F; I166L; Y197M; M230V; M309L | +++ |
| 146 | A91R; Y139F; I166L; Y197L; M230V; M309L | +++ |
| 148 | A91R; Y139F; I166L; Y197M; M230V; M309L | +++ |
| 150 | A91R; Y139F; I166L; L199H; M230V; M309L | +++ |
| 152 | A91R; Y139F; I166L; L199F; M230V; M309L | ++ |
| 154 | A91R; Y139F; I166L; M230V; M309L; T332I | + |
| 156 | A91R; Y139F; I166L; L199C; M230V; M309L | ++++ |
| 158 | A91R; Y139F; I166L; L199V; M230V; M309L | ++ |
| 160 | A91R; Y139F; I166L; L199T; M230V; M309L | +++ |
| 162 | A91R; Y139F; I166L; L199W; M230V; M309L | ++++ |
| 164 | A91R; Y139F; I166L; L199P; M230V; M309L | +++ |
| 166 | A91R; Y139F; I166L; L199M; M230V; M309L | + |
| 168 | A91R; Y139F; I166L; L199A; M230V; M309L | +++ |
| 170 | A91R; Y139F; I166L; L199I; M230V; M309L | ++ |
| 172 | A91R; Y139F; I166L; L199F; M230V; H269R; M309L | + |
| 174 | A91R; T108S; Y139F; I166L; M230V; M266L; T334I | + |
| 176 | A91R; T108S; Y139F; I166L; Y197N; M230V; M266L | ++ |
| 180 | S23T; A91R; I08S; V134A; Y139F; I166L; M230V; M266L; T297V | +++ |
| 182 | A91R; T108S; Y139W; I166L; M230V; M266L; C267A; H269P | + |
| 186 | A91R; T108S; Y139W; I166L; M230V; F259I; M266L; V319M | ++++ |
| 190 | A91R; T108S; Y139F; I166L; V203A; M230V; M266L | + |
| 206 | A91R; Y139F; I166L; M230Y; M309L | ++ |
| 216 | A91R; T108S; Y139F; I166L; L199A; M230V; M266L | + |
| 220 | A91R; T108S; Y139F; C161N; I166L; L199F; M230V; M266L | ++++ |
| 222 | A91R; T108S; Y139F; I166L; H201G; M230V; M266L | ++ |
| 224 | A91R; T108S; Y139F; I166L; Y197M; M230V; M266L; T317A | ++ |
| 226 | A37T; A91R; T108S; Y139F; C161N; I166L; G200S; M230V; M266L | ++++ |
| 228 | W54A; A91R; T108S; Y139F; I166L; L199M; M230V; M266L | +++ |
| 230 | A91R; T108S; Y139F; C161N; I166L; M230V; M266L | + |
| 232 | A91R; T108S; Y139F; C161N; I166L; L199C; M230V; M266L | ++++ |
| 234 | W54V; A91R; T108S; Y139F; I166L; L199M; M230V; M266L | +++ |
| 236 | W54V; A91R; T108S; Y139F; C161N; I166L; L199M; M230V; M233T; M266L | ++++ |
| 238 | A91R; T108S; Y139F; C161N; I166L; L199M; M230V; M266L | +++ |
| 240 | W54V; A91R; T108S; Y139F; C161N; I166L; L199F; M230V; M266L | ++++ |
| 242 | W54V; A91R; T108S; Y139F; I166L; L199M; M230V; M266L | +++ |
| 244 | W54V; A91R; T108S; Y139F; C161N; I166L; G200S; M230V; K240R; M266L; A288T | ++ |
| 246 | W54V; A91R; T108S; Y139F; I166L; L199M; M230V; M266L | +++ |
| 248 | I49V; W54M; A91R; T108S; E121K; Y139F; C161N; I166L; L199M; M230V; M266L | ++ |
| 250 | W54F; M65T; A91R; T108S; Y139F; A163G; I166L; L199C; M230V; M266L; A293T | ++++ |

TABLE 8-continued

Variants showing at least 1.1-fold improvement in activity with CNN substrate for production of acid product relative to "parent" (FIOP) nitrilase encoded by SEQ ID NO: 6.

| SEQ ID NO: | VARIANT AA SEQUENCE MUTATION(S) (C-TERMINAL AA SEQUENCE EXTENSION - WHERE PRESENT) | RELATIVE IMPROVEMENT (FIOP)[1] |
|---|---|---|
| 266 | W54M; A91R; T108S; Y139F; I166L; L199F; Q209R; M230V; M266L; A293T | + |
| 274 | W54F; A91R; T108S; Y139F; I166L; L199C; M230V; M266L | ++++ |
| 278 | W54F; A91R; T108S; Y139F; A163G; I166L; L199C; M230V; M266L; A293T | ++++ |
| 282 | A91R; T108S; Y139F; A163G; I166L; L199C; M230V; M266L; A293T | ++++ |
| 284 | W54M; A91R; T108S; Y139F; A163G; I166L; L199C; M230V; M266L; A293T | ++++ |
| 288 | W54M; A91R; T108S; Y139F; A163G; I166L; L199C; M230V; M266L; A293T | ++++ |
| 290 | W54M; A91R; T108S; T132F; Y139F; A163G; I166L; L199C; M230V; M266L; A293T | ++++ |
| 296 | W54M; A91R; T108S; Y139F; A163G; I166L; L199C; M230V; M266L; A293T; E323G | ++++ |

[1]Relative Improvement (FIOP) scale: "+" indicates 1.1 to 1.5-fold improved; "++" indicates >1.5 to 2.0-fold improved; "+++" indicates >2.0 to 2.5-fold improved; and "++++" indicates >2.5-fold improved.

Nitrilase variants showing at least 1.1-fold improvement for production of amide product from CNN substrate are listed in Table 9 below. Increased activity with for production of amide product from CNN substrate was observed for nitrilase variants including at least one of the following mutations relative to the corresponding position in SEQ ID NO: 2: S23T, A37T, K40E, I49V, W54M, W54F, W54V, M65T, A85R, E121K, V134A, Y139W, C161N, A163G, Y172C, L191I, Y197L, L199F, L199C, L199M, L199A, G200S, Q272E, I289V, A293T, T297V, V319M, E323G, T332I, and T334I.

TABLE 9

Variants showing at least 1.1-fold improvement in activity with substrate for production of amide product relative to "parent" (FIOP) nitrilase encoded by SEQ ID NO: 6

| SEQ ID NO: | VARIANT AA SEQUENCE MUTATION(S) | RELATIVE IMPROVEMENT (FIOP)[1] |
|---|---|---|
| 22 | A91R; T108S; Y139F; C161N; I166L; M230V; M266L | ++++ |
| 24 | A91R; T108S; Y139F; A163G; I166L; M230V; M266L | ++++ |
| 28 | A91R; T108S; Y139F; I166L; L191I; M230V; M266L | + |
| 180 | S23T; A91R; T108S; V134A; Y139F; I166L; M230V; M266L; T297V | +++ |
| 186 | A91R; T108S; Y139W; I166L; M230V; F259I; M266L; V319M | ++ |
| 200 | K40E; A85R; A91R; T108S; Y139F; I166L; M230V; M266L; Q272E; I289V | + |
| 216 | A91R; T108S; Y139F; I166L; L199A; M230V; M266L | ++ |
| 220 | A91R; T108S; Y139F; C161N; I166L; L199F; M230V; M266L | + |
| 226 | A37T; A91R; T108S; Y139F; C161N; I166L; G200S; M230V; M266L | ++++ |
| 230 | A91R; T108S; Y139F; C161N; I166L; M230V; M266L | +++ |
| 232 | A91R; T108S; Y139F; C161N; I166L; L199C; M230V; M266L | ++++ |
| 236 | W54V; A91R; T108S; Y139F; C161N; I166L; L199M; M230V; M233T; M266L | + |
| 238 | A91R; T108S; Y139F; C161N; I166L; L199M; M230V; M266L | +++ |

TABLE 9-continued

Variants showing at least 1.1-fold improvement in activity with substrate for production of amide product relative to "parent" (FIOP) nitrilase encoded by SEQ ID NO: 6

| SEQ ID NO: | VARIANT AA SEQUENCE MUTATION(S) | RELATIVE IMPROVEMENT (FIOP)[1] |
|---|---|---|
| 248 | I49V; W54M; A91R; T108S; E121K; Y139F; C161N; I166L; L199M; M230V; M266L | + |
| 250 | W54F; M65T; A91R; T108S; Y139F; A163G; I166L; L199C; M230V; M266L; A293T | ++++ |
| 274 | W54F; A91R; T108S; Y139F; I166L; L199C; M230V; M266L | + |
| 278 | W54F; A91R; T108S; Y139F; A163G; I166L; L199C; M230V; M266L; A293T | ++++ |
| 282 | A91R; T108S; Y139F; A163G; I166L; L199C; M230V; M266L; A293T | ++++ |
| 284 | W54M; A91R; T108S; Y139F; A163G; I166L; L199C; M230V; M266L; A293T | ++++ |
| 288 | W54M; A91R; T108S; Y139F; A163G; I166L; L199C; M230V; M266L; A293T | ++++ |
| 290 | W54M; A91R; T108S; T132F; Y139F; A163G; I166L; L199C; M230V; M266L; A293T | ++++ |
| 296 | W54M; A91R; T108S; Y139F; A163G; I166L; L199C; M230V; M266L; A293T; E323G | ++++ |
| 302 | A91R; T108S; Y139F; I166L; L191I; M230V; M266L; A293T | ++++ |
| 306 | A91R; T108S; Y139F; I166L; M230V; M266L; A293T | +++ |
| 316 | A91R; T108S; Y139F; I166L; Y172C; L191I; M230V; M266L; A293T | +++ |
| 318 | A91R; T108S; Y139F; A163G; I166L; Y172C; L191I; M230V; M266L; A293T | +++ |

[1]Relative Improvement (FIOP) scale: "+" indicates 1.1 to 1.5-fold improved; "++" indicates >1.5 to 2.0-fold improved; "+++" indicates >2.0 to 2.5-fold improved; and "++++" indicates >2.5-fold improved.

Example 5

Nitrilase Variants with Increased Nitrilase Activity for Substrate DCBN

This example illustrates variants of *B. japonicum* nitrilase having increased nitrilase activity relative to the parent nitrilase variant encoded by SEQ ID NO: 6 in the reaction of the substrate phthalonitrile or "DCBN" (compound of formula Ib) to form the 2-cyanobenzoic acid product (compound of formula IIb) as shown below:

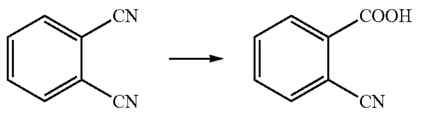

(Ib) (IIb)

Reaction with DCBN:

Reaction mixture contained 10 mM substrate, 10% MeOH, 100 mM potassium phosphate, pH 8.0, 100 μL lysate containing variant enzyme, in a total reaction volume of 300 μL in reaction plate wells. Plates were shaken overnight at 250 rpm and 30° C.

HPLC Sample Preparation:

For HPLC analysis, 1 volume of acetonitrile was added to each well. Plate was sealed and shaken at 850 rpm for 10 min at room temperature. Plate was centrifuged at 2,000 rpm (3220×g) for 10 min to pellet the enzyme debris. A 200 μL volume from each well was transferred to a shallow well plate (Costar 3365). Plate was sealed with heat-sealer set at 170° C. for 2 sec.

Reverse Phase HPLC Conditions:

Samples were examined by injecting 10 μL onto a Phenomenex Luna PFP(2), 5 μm (0.46 cm×250 mm) at a column temperature of 25° C. The mobile phase was 70:30:0.1 (v:v:v) acetonitrile:water:acetic acid; and had a flow-rate of 1.0 mL $min^{-1}$ for 5 min runtime. Detection was carried out at a wavelength of 240 nm. Retention time of the acid is 3.2 min and the nitrile is 4.0 min under the chromatographic conditions.

Results:

Nitrilase variants showing at least 1.1-fold improvement are listed in Table 10 below. Increased activity with the DCBN was observed for nitrilase variants including at least one of the following mutations relative to the corresponding position in SEQ ID NO: 2: S23T, W54MFVA, M65T, A73E, E121K, T132F, V134A, C161N, A163G, K171R, Y172C, Y197M, L199CFM, G200S, H201G, V203A, Q209R, C217T, M233T, K240R, A293T, T297V, T317A, and T330I.

TABLE 10

Variants showing at least 1.1-fold improvement in activity with DCBN substrate relative to "parent" (FIOP) nitrilase encoded by SEQ ID NO: 6

| SEQ ID NO: | VARIANT AA SEQUENCE MUTATION(S) | RELATIVE IMPROVEMENT (FIOP)[1] |
|---|---|---|
| 178 | S23T; A91R; T108S; Y139F; I166L; K171R; M230V; M266L | + |
| 180 | S23T; A91R; T108S; V134A; Y139F; I166L; M230V; M266L; T297V | + |
| 190 | A91R; T108S; Y139F; I166L; V203A; M230V; M266L | + |
| 192 | A73E; A91R; T108S; Y139F; I166F; M230V; M266L | ++ |
| 194 | A91R; T108S; Y139F; I166F; V203A; M230V; M266L; T330I | ++ |
| 196 | A91R; T108S; Y139F; I166F; Y172C; M230V; M266L; Q272E | + |
| 198 | A91R; T108S; Y139F; I166F; V203A; C217T; M230V; M266L | + |
| 202 | A73E; A91R; T108S; Y139F; I166F; C217T; M230V; M266L; Q272E | + |
| 204 | A73E; A91R; T108S; Y139F; I166F; M230V; M266L | + |
| 220 | A91R; T108S; Y139F; C161N; I166L; L199F; M230V; M266L | ++++ |
| 222 | A91R; T108S; Y139F; I166L; H201G; M230V; M266L | + |
| 224 | A91R; T108S; Y139F; I166L; Y197M; M230V; M266L; T317A | + |
| 226 | A37T; A91R; T108S; Y139F; C161N; I166L; G200S; M230V; M266L | ++ |
| 228 | W54A; A91R; T108S; Y139F; I166L; L199M; M230V; M266L | ++++ |
| 232 | A91R; T108S; Y139F; C161N; I166L; L199C; M230V; M266L | ++++ |
| 234 | W54V; A91R; T108S; Y139F; I166L; L199M; M230V; M266L | ++++ |
| 236 | W54V; A91R; T108S; Y139F; C161N; I166L; L199M; M230V; M233T; M266L | ++++ |
| 238 | A91R; T108S; Y139F; C161N; I166L; L199M; M230V; M266L | ++++ |
| 240 | W54V; A91R; T108S; Y139F; C161N; I166L; L199F; M230V; M266L | ++++ |
| 242 | W54V; A91R; T108S; Y139F; I166L; L199M; M230V; M266L | ++++ |
| 244 | W54V; A91R; T108S; Y139F; C161N; I166L; G200S; M230V; K240R; M266L; A288T | +++ |
| 246 | W54V; A91R; T108S; Y139F; I166L; L199M; M230V; M266L | ++++ |
| 248 | I49V; W54M; A91R; T108S; E121K; Y139F; C161N; I166L; L199M; M230V; M266L | ++++ |
| 250 | W54F; M65T; A91R; T108S; Y139F; A163G; I166L; L199C; M230V; M266L; A293T | ++++ |
| 252 | W54M; A91R; T108S; T132F; Y139F; I166L; L199C; M230V; M266L | ++++ |
| 254 | W54M; A91R; T108S; T132F; Y139F; A163G; I166L; L199F; M230V; M266L | ++++ |
| 256 | W54M; A91R; T108S; T132F; Y139F; I166L; L199C; M230V; M266L | +++ |
| 258 | W54F; A91R; T108S; T132F; Y139F; C161N; I166L; L199C; M230V; M266L | + |
| 260 | A91R; T108S; T132F; Y139F; I166L; L199C; M230V; M266L | ++++ |
| 262 | W54M; A91R; T108S; T132F; Y139F; I166L; L199C; M230V; M266L; A293T | + |
| 264 | W54M; A91R; T108S; T132F; Y139F; I166L; L199C; M230V; M266L; A293T | ++ |
| 266 | W54M; A91R; T108S; Y139F; I166L; L199F; Q209R; M230V; M266L; A293T | ++++ |
| 268 | W54M; A91R; T108S; T132F; Y139F; C161N; I166L; L199F; M230V; M266L | ++++ |
| 270 | W54M; A91R; T108S; T132F; Y139F; A163G; I166L; L199C; M230V; M266L | ++++ |
| 272 | W54M; A91R; T108S; T132F; Y139F; I166L; L199C; M230V; M266L; A293T | ++++ |
| 274 | W54F; A91R; T108S; Y139F; I166L; L199C; M230V; M266L | ++++ |
| 276 | W54M; A91R; T108S; T132F; Y139F; A163G; I166L; L199C; M230V; M266L | ++++ |
| 278 | W54F; A91R; T108S; Y139F; A163G; I166L; L199C; M230V; M266L; A293T | ++++ |
| 282 | A91R; T108S; Y139F; A163G; I166L; L199C; M230V; M266L; A293T | ++++ |
| 284 | W54M; A91R; T108S; Y139F; A163G; I166L; L199C; M230V; M266L; A293T | ++++ |
| 288 | W54M; A91R; T108S; Y139F; A163G; I166L; L199C; M230V; M266L; A293T | ++++ |
| 290 | W54M; A91R; T108S; T132F; Y139F; A163G; I166L; L199C; M230V; M266L; A293T | ++++ |
| 292 | A91R; T108S; T132F; Y139F; I166L; L199C; M230V; M266L; A293T | ++ |
| 296 | W54M; A91R; T108S; Y139F; A163G; I166L; L199C; M230V; M266L; A293T; E323G | ++++ |
| 300 | W54F; A91R; T108S; Y139F; I166L; M230V; M266L; A293T | ++ |

[1]Relative Improvement (FIOP) scale: "+" indicates 1.1 to 1.5-fold improved; "++" indicates >1.5 to 2.0-fold improved; "+++" indicates >2.0 to 2.5-fold improved; and "++++" indicates >2.5-fold improved.

Example 6

Nitrilase Variants with Increased Nitrilase Activity for Substrate DCN

This example illustrates variants of *B. japonicum* nitrilase having increased nitrilase activity relative to the parent nitrilase variant encoded by SEQ ID NO: 2 in the reaction of the DCN substrate (compound of formula Ij) to form the (E)-2-cyano-3-phenylacrylic acid product (compound of formula IIj) as shown below:

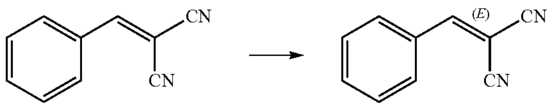

(Ij) (IIj) (E)-acid

Reaction with DCN:

Reaction mixture contained 10 mM substrate, 4% MeOH, 100 mM potassium phosphate, pH 8.0, 100 μL lysate containing variant enzyme, in a total reaction volume of 300 μL in reaction plate wells. Plate was shaken overnight at 250 rpm at 30° C.

HPLC Sample Preparation:

For HPLC analysis, 1 volume of acetonitrile was added to each well. Plate was sealed and shaken at 850 rpm for 10 min at room temperature. Plate was centrifuged at 2,000 rpm (3220×g) for 10 min to pellet the enzyme debris. A 200 μL volume from each well was transferred to a shallow well plate (Costar 3365). Plate was sealed with heat-sealer set at 170° C. for 2 s.

Reverse Phase HPLC Conditions:

Samples were examined by injecting 10 μL onto a Phenomenex Luna PFP(2), 5 μm (0.46 cm×250 mm) with a column temperature of 25° C. The mobile phase was 70:30:0.1 (v:v:v) acetonitrile:water:acetic acid; and has a flow-rate of 2.0 mL $min^{-1}$ for 4 min run time. Detection was carried out at wavelength 300 nm. Retention time of the acid is 1.6 min while the nitrile is 2.8 min under the chromatographic conditions.

Results:

Nitrilase variants showing at least 1.1-fold improvement are listed in Table 11 below. Increased activity with the DCN was observed for nitrilase variants including at least one of the following mutations relative to the corresponding position in SEQ ID NO: 2: A119V, C161N, A163G, L199A and D242A.

TABLE 11

Variants showing at least 1.1-fold improvement in activity with DCN substrate relative to "parent" (FIOP) nitrilase encoded by SEQ ID NO: 2.

| SEQ ID NO: | VARIANT AA SEQUENCE MUTATION(S) | RELATIVE IMPROVEMENT (FIOP)[1] |
|---|---|---|
| 46 | D242A | + |
| 50 | C161N | + |
| 52 | L199A | + |
| 56 | A163G | ++ |
| 60 | A119V | ++ |

[1]Relative Improvement (FIOP) scale: "+" indicates 1.1 to 1.5-fold improved; "++" indicates >1.5 to 2.0-fold improved; "+++" indicates >2.0 to 2.5-fold improved; and "++++" indicates >2.5-fold improved.

Example 7

Nitrilase Variants with Increased Nitrilase Activity for Substrate DEN

This example illustrates variants of *B. japonicum* nitrilase having increased nitrilase activity relative to the parent nitrilase variant encoded by SEQ ID NO: 6 in the reaction of the substrate 3,3-diethoxypropanenitrile or "DEN" (compound of formula Ii) to form the 3,3-diethoxypropanoic acid product (compound of formula IIi) to form product as shown below:

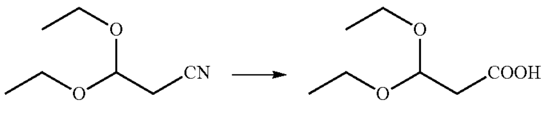

(Ii) (IIi)

Reaction with DEN:

Reaction mixture contained 10 mM substrate, 10% MeOH, 100 mM potassium phosphate, pH 8.0, 25 μL lysate containing variant enzyme, in a total reaction volume of 300 μL in reaction plate wells. Plates were shaken overnight at 250 rpm and 30° C.

GC Sample Preparation:

Hydrochloric acid (50 mL of 1 M) was added to each well, followed by 1 volume of ethyl acetate. Plate was sealed and shakes at 850 rpm for 10 min at room temperature. Plate was centrifuged at 2,000 rpm (3220×g) for 2 min to separate layers. A 100 μL volume of ethyl acetate layer was transferred from each well to a shallow well plate (Costar 3365). Plate was sealed with a heat-sealer set at 170° C. for 2 sec.

GC Conditions:

Agilent HP-5 column; 140° C. [10° C./min]-160° C.; 2 min run time; retention times: acid: 1.74 min, nitrile: 1.5 min.

Results:

Nitrilase variants showing at least 1.1-fold improvement in activity with DEN substrate are listed in Table 12 below. Increased activity with DEN substrate was observed for nitrilase variants including at least one of the following mutations relative to the corresponding position in SEQ ID NO: 2: S23T, A37T, I49V, W54A, W54V, W54M, W54F, E131K, V134A, C161N, A163G, L199M, L199C, L199F, G200S, K240R, A288T, A293T, and T297V.

TABLE 12

Variants showing at least 1.1-fold improvement in activity with DEN substrate relative to "parent" (FIOP) nitrilase encoded by SEQ ID NO: 6.

| SEQ ID NO: | VARIANT AA SEQUENCE MUTATION(S) | RELATIVE IMPROVEMENT (FIOP) |
|---|---|---|
| 180 | S23T; A91R; T108S; V134A; Y139F; I166L; M230V; M266L; T297V | + |
| 220 | A91R; T108S; Y139F; C161N; I166L; L199F; M230V; M266L | ++ |
| 226 | A37T; A91R; T108S; Y139F; C161N; I166L; G200S; M230V; M266L | + |
| 228 | W54A; A91R; T108S; Y139F; I166L; L199M; M230V; M266L | + |
| 230 | A91R; T108S; Y139F; C161N; I166L; M230V; M266L | + |
| 232 | A91R; T108S; Y139F; C161N; I166L; L199C; M230V; M266L | ++ |
| 234 | W54V; A91R; T108S; Y139F; I166L; L199M; M230V; M266L | + |
| 236 | W54V; A91R; T108S; Y139F; C161N; I166L; L199M; M230V; M233T; M266L | + |
| 238 | A91R; T108S; Y139F; C161N; I166L; L199M; M230V; M266L; | ++ |
| 240 | W54V; A91R; T108S; Y139F; C161N; I166L; L199F; M230V; M266L | ++ |
| 242 | W54V; A91R; T108S; Y139F; I166L; L199M; M230V; M266L | + |
| 244 | W54V; A91R; T108S; Y139F; C161N; I166L; G200S; M230V; K240R; M266L; A288T | + |
| 246 | W54V; A91R; T108S; Y139F; I166L; L199M; M230V; M266L | + |
| 248 | I49V; W54M; A91R; T108S; E121K; Y139F; C161N; I166L; L199M; M230V; M266L | ++ |
| 266 | W54M; A91R; T108S; Y139F; I166L; L199F; Q209R; M230V; M266L; A293T | ++ |
| 274 | W54F; A91R; T108S; Y139F; I166L; L199C; M230V; M266L | + |
| 278 | W54F; A91R; T108S; Y139F; A163G; I166L; L199C; M230V; M266L; A293T | + |
| 282 | A91R; T108S; Y139F; A163G; I166L; L199C; M230V; M266L; A293T | + |
| 284 | W54M; A91R; T108S; Y139F; A163G; I166L; L199C; M230V; M266L; A293T | + |

[1]Relative Improvement (FIOP) scale: "+" indicates 1.1 to 1.5-fold improved; "++" indicates >1.5 to 2.0-fold improved; "+++" indicates >2.0 to 2.5-fold improved; and "++++" indicates >2.5-fold improved.

Example 8

Nitrilase Variants with Increased Nitrilase Activity for Substrate DMC

This example illustrates variants of *B. japonicum* nitrilase having increased nitrilase activity relative to the parent nitrilase variant encoded by SEQ ID NO: 6 in the reaction of the substrate 6-bromo-2,2-dimethylhexanenitrile or "DMC" (compound of formula Ig) to form the 6-bromo-2,2-dimethylhexanoic acid product (compound of formula IIg) as shown below:

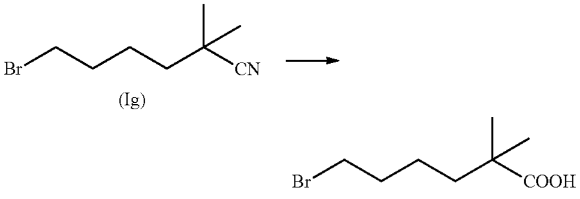

(Ig)

(IIg)

Reaction with DMC:

Reaction mixture contained 10 mM substrate, 10% MeOH, 100 mM potassium phosphate, pH 8.0, 100 μL lysate containing variant enzyme, in a total reaction volume of 300 μL in reaction plate wells. Plates were shaken overnight at 250 rpm and 30° C.

GC Sample Preparation:

Hydrochloric acid (50 mL of 1 M) was added to each well, followed by 1 volume of ethyl acetate. Plate was sealed and shaken at 850 rpm for 10 min at room temperature. Plate was centrifuged at 2,000 rpm (3220×g) for 2 min to separate layers. A 100 μL volume of ethyl acetate layer was transferred from each well to a shallow well plate (Costar 3365). Plate was sealed with heat-sealer set at 170° C. for 2 sec.

GC Conditions:

Agilent HP-5 column; 180° C. isothermal 2 min; retention time: acid: 1.9 min.

Results:

Nitrilase variants showing at least 1.1-fold improvement in activity with DMC substrate are listed in Table 13 below. Increased activity with DMC substrate was observed for nitrilase variants including at least one of the following mutations relative to the corresponding position in SEQ ID NO: 2: F30L, I49V, W54F, W54V, W54A, W54M, E121K, C161N, L191I, L199M, I225T, A293T, T332I, T334S, T334L, and T334I

TABLE 13

Variants showing at least 1.1-fold improvement in activity with DMC substrate relative to "parent" (FIOP) nitrilase encoded by SEQ ID NO: 6

| SEQ ID NO: | VARIANT AA SEQUENCE MUTATION(S) (C-TERMINAL AA SEQUENCE EXTENSION - WHERE PRESENT) | RELATIVE IMPROVEMENT (FIOP)[1] |
|---|---|---|
| 4 | F30L; A91R; Y139F; I166L; M230V; M309L; T334S (334QTGHHQDPLQGRADGQA) | ++ |
| 8 | A91R; Y139F; I166L; M230V; A293T; M309L | ++ |
| 14 | A91R; T108S; Y139F; I166L; M230V; M266L; T334L (334SQTGHHQDPLQGRADGQA) | +++ |
| 16 | W54F; A91R; T108S; Y139F; I166L; M230V; M266L | + |
| 154 | A91R; Y139F; I166L; M230V; M309L; T332I | + |
| 174 | A91R; T108S; Y139F; I166L; M230V; M266L; T334I | + |
| 228 | W54A; A91R; T108S; Y139F; I166L; L199M; M230V; M266L | + |
| 234 | W54V; A91R; T108S; Y139F; I166L; L199M; M230V; M266L | + |
| 236 | W54V; A91R; T108S; Y139F; C161N; I166L; L199M; M230V; M233T; M266L | + |
| 246 | W54V; A91R; T108S; Y139F; I166L; L199M; M230V; M266L | + |
| 248 | I49V; W54M; A91R; T108S; E121K; Y139F; C161N; I166L; L199M; M230V; M266L | ++ |
| 298 | W54F; A91R; T108S; Y139F; I166L; L191I; M230V; M266L; A293T; T332I | +++ |
| 300 | W54F; A91R; T108S; Y139F; I166L; M230V; M266L; A293T | ++ |
| 306 | A91R; T108S; Y139F; I166L; M230V; M266L; A293T | + |
| 308 | W54F; A91R; T108S; Y139F; I166L; L191I; I225T; M230V; M266L; A293T | +++ |
| 312 | W54F; A91R; T108S; Y139F; I166L; L191I; M230V; M266L; A293T | ++++ |

[1]Relative Improvement (FIOP) scale: "+" indicates 1.1 to 1.5-fold improved; "++" indicates >1.5 to 2.0-fold improved; "+++" indicates >2.0 to 2.5-fold improved; and "++++" indicates >2.5-fold improved.

Example 9

Nitrilase Variants with Increased Nitrilase Activity for Substrate DPN

This example illustrates variants of *B. japonicum* nitrilase having increased nitrilase activity relative to the parent nitrilase variant encoded by SEQ ID NO: 2 in the reaction of the substrate 4-(cyanomethyl)benzonitrile or "DPN" (compound of formula Ik) to form the 2-(4-cyanophenyl)acetic acid (monoacid) and 4-(carboxymethyl)benzoic acid (diacid) products (compounds of formula IIk' and IIk" respectively) as shown below:

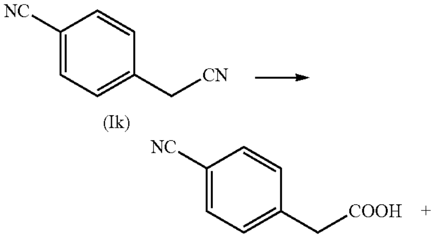

(Ik)

(IIk')
monoacid

-continued

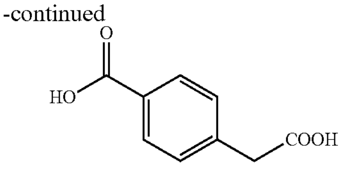

(IIk")
diacid

Reaction with DPN (Low Enzyme Loading):

Reaction mixture contained 10 mM substrate, 4% MeOH, 100 mM potassium phosphate, pH 8.0, 100 μL of 100× diluted lysate containing variant enzyme, in a total reaction volume of 300 μL in reaction plate wells. Plate was shaken 1 h at 250 rpm at 30° C.

Reaction with DPN (High Enzyme Loading):

Reaction mixture contained 10 mM substrate, 4% MeOH, 100 mM potassium phosphate, pH 8.0, 100 μL of lysate (not diluted) containing variant enzyme, in a total reaction volume of 300 μL in reaction plate wells. Plate was shaken 1 h at 250 rpm at 30° C.

HPLC Sample Preparation:

For HPLC preparation, 1 volume of acetonitrile was added to each well. Plate was sealed and shaken at 850 rpm for 10 min at room temperature. Plate was centrifuged at 2,000 rpm (3220×g) for 10 min to pellet the enzyme debris. A 200 μL volume from each well was transferred to a shallow well plate (Costar 3365). Plate was sealed with heat-sealer set at 170° C. for 2 sec.

Reverse Phase HPLC Conditions:

Samples were examined by injecting 10 μL onto a Phenomenex Luna PFP(2), 5 μm (0.46 cm×250 mm) at a column temperature of 25° C. The mobile phase was 70:30:0.1 (v:v:v) acetonitrile:water:acetic acid; and had a flow-rate of 2.0 mL $min^{-1}$ for 4 min run time. Detection was carried out at wavelength 300 nm. Retention times are: phenyl mono-acid—8.3 min; benzylic mono-acid—9.3 min; and nitrile—18 min, under the chromatographic conditions.

Results:

Nitrilase variants showing at least 1.1-fold improvement are listed in Table 14 below. Increased activity with the DPN was observed for nitrilase variants including at least one of the following mutations relative to the corresponding position in SEQ ID NO: 2: W54M, A163G, L191I, and D242A.

TABLE 14

Variants showing at least 1.1-fold improvement in activity with DPN substrate relative to "parent" (FIOP) nitrilase encoded by SEQ ID NO: 2

| SEQ ID NO: | VARIANT AA SEQUENCE MUTATION(S) | RELATIVE IMPROVEMENT (FIOP)[1] |
|---|---|---|
| 30 | L191I | ++ |
| 36 | W54M | + |
| 46 | D242A | + |
| 56 | A163G | + |

[1]Relative Improvement (FIOP) scale: "+" indicates 1.1 to 1.5-fold improved; "++" indicates >1.5 to 2.0-fold improved; "+++" indicates >2.0 to 2.5-fold improved; and "++++" indicates >2.5-fold improved.

Additionally, under the high enzyme loading conditions, the nitrilase variants encoded by SEQ ID NOs: 47 (A163H mutation) and 49 (C161N mutation) produced the diacid product at 7.0% and 5.0% conversion rate, respectively. The conversion to the diacid product is a novel activity that does not exist in the wild-type nitrilase.

Example 10

Nitrilase Variants with Increased Nitrilase Activity for Substrate PBA

This example illustrates variants of *B. japonicum* nitrilase having increased nitrilase activity relative to the parent nitrilase variant encoded by SEQ ID NO: 2 or SEQ ID NO: 6 in the reaction of the substrate 2-phenylbutanenitrile or "PBA" (compound of formula Ic) to form the (R)-2-phenylbutanoic acid and (S)-2-phenylbutanoic acid products (compounds of formula IIc' and IIc" respectively) as shown below:

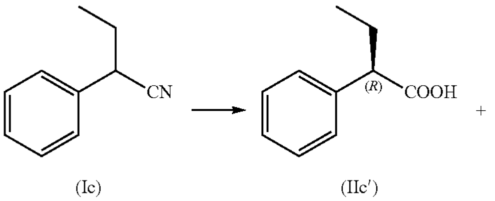

(Ic)

(IIc')
(R)-acid

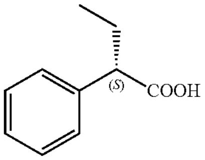

(IIc")
(S)-acid

Reaction with PBA (Assays Relative to SEQ ID NO: 2):

Reaction mixtures contained 10 mM substrate, 4% MeOH, 100 mM potassium phosphate, pH 8.0, 100 μL lysate containing variant enzyme, in a total reaction volume of 300 μL in reaction plate wells. Plate was shaken overnight at 250 rpm at 30° C.

Reaction with PBA (Assays Relative to SEQ ID NO: 6):

Reaction mixtures contained 20 mM substrate, 10% MeOH, 100 mM potassium phosphate, pH 8.0, 100 μL lysate containing variant enzyme, in a total reaction volume of 300 μL in reaction plate wells. Plates were shaken overnight at 250 rpm and 30° C.

HPLC Sample Preparation:

For HPLC preparation, 1 volume of acetonitrile was added to each well of variant enzyme reaction plate. Plate was sealed and shake at 850 rpm for 10 min at room temperature. Plate was centrifuged at 2,000 rpm (3220×g) for 10 min to pellet enzyme debris. A 200 μL volume from each well was transferred to a shallow well plate (Costar 3365) and the plate sealed with a heat-sealer set at 170° C. for 2 sec.

Reverse Phase HPLC Conditions:

Samples were examined by injecting 10 μL onto a Cyclobond I 2000 HP-RSP, 5 μm (0.46 cm×250 mm) at a column temperature 25° C. The mobile phase was 50:50 acetonitrile: water with 10 mM ammonium acetate (pH 3.5), and had a flow-rate of 1.5 mL $min^{-1}$ for 4 min runtime. Detection was carried out at wavelength 225 nm. Retention times are: (R)-acid—3.0 min; (S)-acid—3.2 min, and nitrile—2.7 min, under the chromatographic conditions.

Results:

Nitrilase variants showing at least 1.1-fold improvement in activity with PBA substrate are listed in Table 15 below. Increased activity with PBA substrate was observed for nitrilase variants including at least one of the following mutations relative to the corresponding position in SEQ ID NO: 2:

F30L, W54F, W54M, M65T, T132H, T132M, T132L, T132F, A163G, A163W, Y172C, L191I, Y197L, L199C, I225T, M230A, P238A, A293T, T332I, T334I, T334L, and T334S.

TABLE 15

Variants showing at least 1.1-fold improvement in activity with PBA substrate relative to "parent" (FIOP) nitrilase encoded by SEQ ID NO: 2 or SEQ ID NO: 6.

| SEQ ID NO: | VARIANT AA SEQUENCE MUTATION(S) (C-TERMINAL AA SEQUENCE EXTENSION - WHERE PRESENT) | RELATIVE IMPROVEMENT (FIOP)[1] |
|---|---|---|
| | ASSAYS RELATIVE TO SEQ ID NO: 2 | |
| 42 | A163W | + |
| 44 | M230A | + |
| 54 | P238A | + |
| | ASSAYS RELATIVE TO SEQ ID NO: 6 | |
| 4 | F30L; A91R; Y139F; I166L; M230V; M309L; T334S (334QTGHHQDPLQGRADGQA) | ++++ |
| 8 | A91R; Y139F; I166L; M230V; A293T; M309L | +++ |
| 10 | A91R; Y139F; I166L; Y197L; M230V; M309L; T334I | + |
| 14 | A91R; T108S; Y139F; I166L; M230V; M266L; T334L (334SQTGHHQDPLQGRADGQA) | +++ |
| 20 | A91R; T108S; T132F; Y139F; I166L; M230V; M266L | ++++ |
| 24 | A91R; T108S; Y139F; A163G; I166L; M230V; M266L | ++++ |
| 28 | A91R; T108S; Y139F; I166L; L191I; M230V; M266L | + |
| 154 | A91R; Y139F; I166L; M230V; M309L; T332I | +++ |
| 174 | A91R; T108S; Y139F; I166L; M230V; M266L; T334I | ++ |
| 210 | A91R; T108S; T132H; Y139F; I166L; M230V; M266L | ++ |
| 212 | A91R; T108S; T132M; Y139F; I166L; M230V; M266L | ++ |
| 214 | A91R; T108S; T132L; Y139F; I166L; M230V; M266L | ++ |
| 250 | W54F; M65T; A91R; T108S; Y139F; A163G; I166L; L199C; M230V; M266L; A293T | ++ |
| 256 | W54M; A91R; T108S; T132F; Y139F; I166L; L199C; M230V; M266L | + |
| 270 | W54M; A91R; T108S; T132F; Y139F; A163G; I166L; L199C; M230V; M266L | ++ |
| 276 | W54M; A91R; T108S; T132F; Y139F; A163G; I166L; L199C; M230V; M266L | + |
| 284 | W54M; A91R; T108S; Y139F; A163G; I166L; L199C; M230V; M266L; A293T | + |
| 288 | W54M; A91R; T108S; Y139F; A163G; I166L; L199C; M230V; M266L; A293T | + |
| 298 | W54F; A91R; T108S; Y139F; I166L; L191I; M230V; M266L; A293T; T332I | ++++ |
| 300 | W54F; A91R; T108S; Y139F; I166L; M230V; M266L; A293T | +++ |
| 302 | A91R; T108S; Y139F; I166L; L191I; M230V; M266L; A293T | ++++ |
| 304 | A91R; T108S; T132H; Y139F; I166L; L191I; M230V; M266L | +++ |
| 308 | W54F; A91R; T108S; Y139F; I166L; L191I; I225T; M230V; M266L; A293T | +++ |
| 310 | A91R; T108S; T132H; Y139F; A163G; I166L; L191I; M230V; M266L | ++ |
| 312 | W54F; A91R; T108S; Y139F; I166L; L191I; M230V; M266L; A293T | ++++ |
| 316 | A91R; T108S; Y139F; I166L; Y172C; L191I; M230V; M266L; A293T | ++++ |
| 318 | A91R; T108S; Y139F; A163G; I166L; Y172C; L191I; M230V; M266L; A293T | ++++ |

[1]Relative Improvement (FIOP) scale: "+" indicates 1.1 to 1.5-fold improved; "++" indicates >1.5 to 2.0-fold improved; "+++" indicates >2.0 to 2.5-fold improved; and "++++" indicates >2.5-fold improved.

Nitrilase variants showing increased stereoselectivity in producing the (S)-product of the PBA substrate (relative to SEQ ID NO: 6 which produces racemic product) are listed in Table 16 below. Increased stereoselectivity for the (S)-product was observed for nitrilase variants including at least one of the following mutations relative to the corresponding position in SEQ ID NO: 2: W54F, W54M, T132H, T132M, T132L, A163G, and A293T.

TABLE 16

Variants showing increased stereoselectivity for (S)-product of the PBA substrate relative to nitrilase encoded by SEQ ID NO: 6.

| SEQ ID NO: | VARIANT AA SEQUENCE MUTATION(S) | INCREASED STEREO-SPECIFICITY[1] |
|---|---|---|
| 20 | A91R; T108S; T132F; Y139F; I166L; M230V; M266L | ++++ |
| 24 | A91R; T108S; Y139F; A163G; I166L; M230V; M266L | + |
| 210 | A91R; T108S; T132H; Y139F; I166L; M230V; M266L | +++ |
| 212 | A91R; T108S; T132M; Y139F; I166L; M230V; M266L | ++++ |
| 214 | A91R; T108S; T132L; Y139F; I166L; M230V; M266L | ++++ |
| 250 | W54F; M65T; A91R; T108S; Y139F; A163G; I166L; L199C; M230V; M266L; A293T | +++ |
| 252 | W54M; A91R; T108S; T132F; Y139F; I166L; L199C; M230V; M266L | ++++ |
| 254 | W54M; A91R; T108S; T132F; Y139F; A163G; I166L; L199F; M230V; M266L | ++++ |
| 256 | W54M; A91R; T108S; T132F; Y139F; I166L; L199C; M230V; M266L | ++++ |
| 258 | W54F; A91R; T108S; T132F; Y139F; C161N; I166L; L199C; M230V; M266L | ++++ |
| 260 | A91R; T108S; T132F; Y139F; I166L; L199C; M230V; M266L | ++++ |
| 262 | W54M; A91R; T108S; T132F; Y139F; I166L; L199C; M230V; M266L; A293T | ++++ |
| 264 | W54M; A91R; T108S; T132F; Y139F; I166L; L199C; M230V; M266L; A293T | ++++ |
| 268 | W54M; A91R; T108S; T132F; Y139F; C161N; I166L; L199F; M230V; M266L | ++++ |
| 270 | W54M; A91R; T108S; T132F; Y139F; A163G; I166L; L199C; M230V; M266L | ++++ |
| 276 | W54M; A91R; T108S; T132F; Y139F; A163G; I166L; L199C; M230V; M266L | ++++ |
| 278 | W54F; A91R; T108S; Y139F; A163G; I166L; L199C; M230V; M266L; A293T | ++++ |
| 280 | W54F; A91R; T108S; T132F; Y139F; C161N; I166L; L199C; M230V; M266L; A293T | ++++ |
| 282 | A91R; T108S; Y139F; A163G; I166L; L199C; M230V; M266L; A293T | ++++ |
| 284 | W54M; A91R; T108S; Y139F; A163G; I166L; L199C; M230V; M266L; A293T | ++++ |
| 286 | W54M; A91R; T108S; T132F; Y139F; I166L; L199C; M230V; M266L; A293T | ++++ |
| 288 | W54M; A91R; T108S; Y139F; A163G; I166L; L199C; M230V; M266L; A293T | ++++ |
| 290 | W54M; A91R; T108S; T132F; Y139F; A163G; I166L; L199C; M230V; M266L; A293T | ++++ |
| 292 | A91R; T108S; T132F; Y139F; I166L; L199C; M230V; M266L; A293T | ++++ |
| 294 | W54F; A91R; T108S; T132F; Y139F; I166L; L199C; M230V; M266L; A293T | ++++ |
| 296 | W54M; A91R; T108S; Y139F; A163G; I166L; L199C; M230V; M266L; A293T; E323G | ++++ |
| 300 | W54F; A91R; T108S; Y139F; I166L; M230V; M266L; A293T | + |
| 304 | A91R; T108S; T132H; Y139F; I166L; L191I; M230V; M266L | ++++ |
| 306 | A91R; T108S; Y139F; I166L; M230V; M266L; A293T | + |
| 308 | W54F; A91R; T108S; Y139F; I166L; L191I; I225T; M230V; M266L; A293T | + |
| 310 | A91R; T108S; T132H; Y139F; A163G; I166L; L191I; M230V; M266L | ++++ |

TABLE 16-continued

Variants showing increased stereoselectivity for (S)-product of the PBA substrate relative to nitrilase encoded by SEQ ID NO: 6.

| SEQ ID NO: | VARIANT AA SEQUENCE MUTATION(S) | INCREASED STEREO-SPECIFICITY[1] |
|---|---|---|
| 314 | A91R; T108S; T132H; Y139F; A163G; I166L; L191I; Q209R; Q228R; M230V; M266L; A293T | ++++ |

[1]Stereoselectivity scale: "+" indicates 20% to 40% e.e. of product; "++" indicates >40% to 60% e.e. of product; "+++" indicates >60% to 80% e.e. of product; and "++++" indicates >80% to 100% e.e. of product.

Nitrilase variants showing increased stereoselectivity in producing the (R)-product of the PBA substrate (relative to SEQ ID NO: 6 which produces racemic product) are listed in Table 17 below. Increased stereoselectivity for the (R)-product was observed for nitrilase variants including at least one of the following mutations relative to the corresponding position in SEQ ID NO: 2: W54A, Y139W, A163W, K171R, Y197L, Y197N, L199A, V203A, C267A, and H269P.

TABLE 17

Variants showing increased stereoselectivity for (R)-product of the PBA substrate relative to nitrilase encoded by SEQ ID NO: 6.

| SEQ ID NO: | VARIANT AA SEQUENCE MUTATION(S) | INCREASED STEREO-SPECIFICITY[1] |
|---|---|---|
| 26 | A91R; T108S; Y139F; A163W; I166L; M230V; M266L | ++++ |
| 146 | A91R; Y139F; I166L; Y197L; M230V; M309L | ++ |
| 152 | A91R; Y139F; I166L; L199F; M230V; M309L | + |
| 156 | A91R; Y139F; I166L; L199C; M230V; M309L | + |
| 176 | A91R; T108S; Y139F; I166L; Y197N; M230V; M266L | ++ |
| 178 | S23T; A91R; T108S; Y139F; I166L; K171R; M230V; M266L | + |
| 182 | A91R; T108S; Y139W; I166L; M230V; M266L; C267A; H269P | + |
| 190 | A91R; T108S; Y139F; I166L; V203A; M230V; M266L | + |
| 216 | A91R; T108S; Y139F; I166L; L199A; M230V; M266L | ++ |
| 218 | W54A; A91R; T108S; Y139F; I166L; M230V; M266L | + |
| 320 | A91R; T108S; T132F; Y139F; A163W; I166L; M230V; M266L; A293T | ++++ |

[1]Stereoselectivity scale: "+" indicates 20% to 40% e.e. of product; "++" indicates >40% to 60% e.e. of product; "+++" indicates >60% to 80% e.e. of product; and "++++" indicates >80% to 100% e.e. of product.

Example 11

Nitrilase Variants with Increased Nitrilase Activity for Substrate TMAN

This example illustrates variants of *B. japonicum* nitrilase having increased nitrilase activity relative to the parent nitrilase variant encoded by SEQ ID NO: 6 in the reaction of the substrate 3,3,3-trifluoro-2-hydroxy-2-phenylpropanenitrile or "TMAN" (compound of formula Id) to form the (S)- or (R)-3,3,3-trifluoro-2-hydroxy-2-phenylpropanoic acid products (compounds of formula IId' and IId" respectively) as shown below:

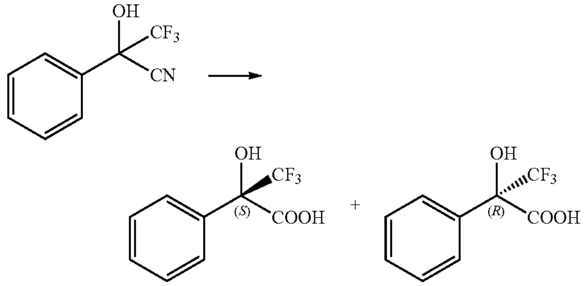

Reaction with TMAN:

Reaction mixture contained 10 mM substrate, 10% MeOH, 100 mM potassium phosphate, pH 8.0, 100 μL lysate containing variant enzyme, in a total reaction volume of 300 μL in reaction plate wells. Plates were shaken overnight at 250 rpm and 30° C.

HPLC Sample Preparation:

For HPLC preparation, 1 volume of acetonitrile was added to each well. Plate was sealed and shaken at 850 rpm for 10 min at room temperature. Plate was centrifuged at 2,000 rpm (3220×g) for 10 min to pellet the enzyme debris. A 200 μL volume from each well was transferred to a shallow well plate (Costar 3365). Plate was sealed with heat-sealer set at 170° C. for 2 sec.

Reverse Phase HPLC Conditions:

Samples were examined by injecting 10 μL onto a Supelco Astec Chirobiotic TAG column, 5 μm (0.46 cm×250 mm) at a column temperature of 25° C. the mobile phase was 70:30:0.1 (v:v:v) acetonitrile:water:phosphoric acid; and had a flow-rate of 1.5 mL $min^{-1}$ for 6 min run time; Retention times are: (R)-acid—3.9 min; (S)-acid—4.9 min; cyanohydrin—2.0 min; and ketone—2.0 min.

Results:

Nirilase variants showing at least 1.1-fold improvement in activity with TMAN substrate are listed in Table 18 below. Increased activity with TMAN substrate was observed for nitrilase variants including at least one of the following mutations relative to the corresponding position in SEQ ID NO: 2: S23T, F30L, A37T, K40E, W54M, A73E, A85R, K130R, T132H, V134A, C161N, A163G, S170G, Y172C, L191I, Y197L, L199M, L199F, G200S, H201G, V203A, Q209R, H269P, Q272E, I289V, A293T, T297V, A327V, T330I, T334I, T334S, and T334L.

TABLE 18

Variants showing at least 1.1-fold improvement in activity with TMAN substrate relative to "parent" (FIOP) nitrilase encoded by SEQ ID NO: 6.

| SEQ ID NO: | VARIANT AA SEQUENCE MUTATION(S) (C-TERMINAL AA SEQUENCE EXTENSION - WHERE PRESENT) | RELATIVE IMPROVEMENT (FIOP)[1] |
|---|---|---|
| 4 | F30L; A91R; Y139F; I166L; M230V; M309L; T334S (334QTGHHQDPLQGRADGQA) | ++++ |
| 10 | A91R; Y139F; I166L; Y197L; M230V; M309L; T334I | ++ |
| 14 | A91R; T108S; Y139F; I166L; M230V; M266L; T334L (334SQTGHHQDPLQGRADGQA) | + |
| 22 | A91R; T108S; Y139F; C161N; I166L; M230V; M266L | + |
| 28 | A91R; T108S; Y139F; I166L; L191I; M230V; M266L | + |
| 180 | S23T; A91R; T108S; V134A; Y139F; I166L; M230V; M266L; T297V | ++++ |

TABLE 18-continued

Variants showing at least 1.1-fold improvement in activity with TMAN substrate relative to "parent" (FIOP) nitrilase encoded by SEQ ID NO: 6.

| SEQ ID NO: | VARIANT AA SEQUENCE MUTATION(S) (C-TERMINAL AA SEQUENCE EXTENSION - WHERE PRESENT) | RELATIVE IMPROVEMENT (FIOP)[1] |
|---|---|---|
| 184 | A91R; T108S; K130R; Y139F; I166L; S170G; M230V; M266L; H269P; T297V; (334CQTGHHQDPLQGRADGQA) | + |
| 188 | A73E; A91R; T108S; Y139F; I166F; M230V; M266L; Q272E; A327V | ++ |
| 192 | A73E; A91R; T108S; Y139F; I166F; M230V; M266L | ++ |
| 194 | A91R; T108S; Y139F; I166F; V203A; M230V; M266L; T330I | + |
| 196 | A91R; T108S; Y139F; I166F; Y172C; M230V; M266L; Q272E | + |
| 200 | K40E; A85R; A91R; T108S; Y139F; I166L; M230V; M266L; Q272E; I289V | + |
| 210 | A91R; T108S; T132H; Y139F; I166L; M230V; M266L | + |
| 220 | A91R; T108S; Y139F; C161N; I166L; L199F; M230V; M266L | ++ |
| 222 | A91R; T108S; Y139F; I166L; H201G; M230V; M266L | + |
| 226 | A37T; A91R; T108S; Y139F; C161N; I166L; G200S; M230V; M266L | + |
| 230 | A91R; T108S; Y139F; C161N; I166L; M230V; M266L | + |
| 238 | A91R; T108S; Y139F; C161N; I166L; L199M; M230V; M266L | ++ |
| 266 | W54M; A91R; T108S; Y139F; I166L; L199F; Q209R; M230V; M266L; A293T | ++ |
| 304 | A91R; T108S; T132H; Y139F; I166L; L191I; M230V; M266L | ++++ |
| 310 | A91R; T108S; T132H; Y139F; A163G; I166L; L191I; M230V; M266L | ++ |
| 314 | A91R; T108S; T132H; Y139F; A163G; I166L; L191I; Q209R; Q228R; M230V; M266L; A293T | ++++ |

[1]Relative Improvement (FIOP) scale: "+" indicates 1.1 to 1.5-fold improved; "++" indicates >1.5 to 2.0-fold improved; "+++" indicates >2.0 to 2.5-fold improved; and "++++" indicates >2.5-fold improved.

Additionally, nitrilase variants showing increased stereoselectivity in producing the (S)-product of the TMAN substrate (relative to SEQ ID NO: 6 which produces 85% ee (R)-product) are listed in Table 19 below. Increased stereoselectivity for the (S)-product was observed for nitrilase variants including at least one of the following mutations relative to the corresponding position in SEQ ID NO: 2: Y132F, A163G, and M230Y.

TABLE 19

Variants showing increased stereoselectivity in producing the (S)-product of the TMAN substrate relative to nitrilase encoded by SEQ ID NO: 6.

| SEQ ID NO: | VARIANT AA SEQUENCE MUTATION(S) | INCREASED STEREO-SPECIFICITY[1] |
|---|---|---|
| 20 | A91R; T108S; T132F; Y139F; I166L; M230V; M266L | +++ |
| 24 | A91R; T108S; Y139F; A163G; I166L; M230V; M266L | + |
| 206 | A91R; Y139F; I166L; M230Y; M309L | +++ |

[1]Stereoselectivity scale: "+" indicates 20% to 40% e.e. of product; "++" indicates >40% to 60% e.e. of product; "+++" indicates >60% to 80% e.e. of product; and "++++" indicates >80% to 100% e.e. of product.

Example 12

Nitrilase Variants with Increased Nitrilase Activity for Substrate

This example illustrates variants of *B. japonicum* nitrilase having increased nitrilase activity relative to the parent nitrilase variant encoded by SEQ ID NO: 4 in the reaction of the ketone substrate, 1,1,1-trifluorobutan-2-one (compound of formula Ih) to form the (S)-α-hydroxyacid product, (S)-2-hydroxy-2-(trifluoromethyl)butanoic acid (compound of formula IIh) as shown below:

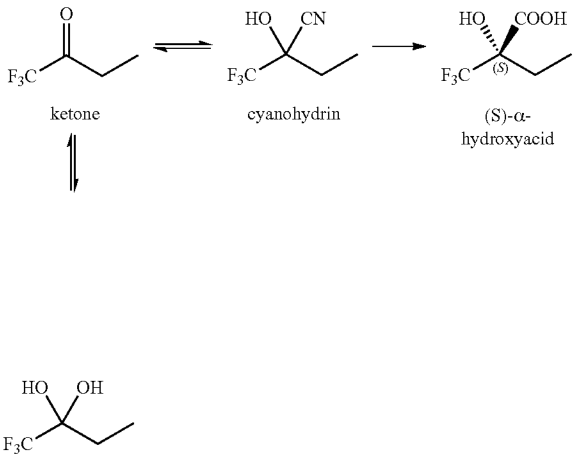

ketone cyanohydrin (S)-α-hydroxyacid hydrate

Reaction with Substrate Ii (2-hydroxy-2-(trifluoromethyl)butanenitrile):

Reaction mixture contained 10 g/L cyanohydrin (2-hydroxy-2-(trifluoromethyl)butanenitrile), 9% methanol, 100 μL lysate containing variant enzyme, 100 mM triethanolamine, pH 8.0, in a total reaction volume of 250 μL in reaction well plates. Plates were shaken overnight at 250 rpm room temperature.

GC Sample Preparation:

For GC analysis, 50 μL of 1 M $FeSO_4$ was added to a 250 μL sample of the reaction mixture and allowed to incubate for 20 min. Then 75 μL of 1 N HCl was added. The 300 μL volume was extracted with MTBE containing 0.5 g/L of n-undecane. The organic layer was used for GC analysis.

GC Analysis Conditions:

DB-1 column (30 m length×0.32 mm ID×0.25 μm film thickness). Temperature program was isothermal at 140° C., head pressure of 17.9 psi, column flow of 3.00 ml/min, and a linear velocity of 51.3 cm/sec. Detection was by FID. Elution order is: amide (1.33 min), hydroxyacid (1.37 min), and n-undecane (1.64 min).

Results:

Nitrilase variants showing at least 1.1-fold improvement are listed in Table 20 below. Increased activity with the 2-hydroxy-2-(trifluoromethyl)butanenitrile was observed for nitrilase variants including at least one of the following mutations relative to the corresponding position in SEQ ID NO: 2: S23T, F30L, W54Y, W55F, S152T, Y172C, A173V, L191F, G200S, V203A, V282I, A293T, T297V, G303P, D295N, T317A, E323K, and T332S.

TABLE 20

Variants showing at least 1.1-fold improvement in activity with 2-hydroxy-2-(trifluoromethyl)butanenitrile substrate relative to "parent" (FIOP) nitrilase encoded by SEQ ID NO: 4

| SEQ ID NO: | VARIANT AA SEQUENCE MUTATION(S) (C-TERMINAL AA SEQUENCE EXTENSION - WHERE PRESENT) | RELATIVE IMPROVEMENT (FIOP)[1] |
|---|---|---|
| 322 | F30L; W55F; A91R; Y139F; I166L; M230V; D295N; M309L; T317A; E323K; D324N; T334S; (334QTGHHQDPLQGKANGQA) | + |
| 324 | F30L; A91R; Y139F; S152T; I166L; M230V; V282I; G303P; M309L; T334S; (334QTGHHQDPLQGKANGQA) | + |
| 326 | F30L; W54M; A91R; Y139F; I166L; M230V; A293T; M309L; T334S; (334QTGHHQDPLQGKANGQA) | ++ |
| 328 | S23T; F30L; A91R; Y139F; I166L; M230V; M309L; T317A; T334S; (334QTGHHQDPLQGKANGQA) | ++ |
| 330 | S23T; F30L; A91R; Y139F; I166L; G200S; M230V; T297V; M309L; T334S; (334QTGHHQDPLQGKANGQA) | ++ |
| 332 | S23T; F30L; A91R; Y139F; I166L; M230V; T297V; M309L; T334S (334QTGHHQDPLQGKANGQA) | + |
| 334 | F30L; A91R; Y139F; I166L; M230V; A293V; T297G; M309L; T317A; T334S; (334QTGHHQDPLQGKANGQA) | + |
| 336 | S23T; F30L; A91R; Y139F; I166L; M230V; T297V; M309L; T317A; T334S; (334QTGHHQDPLQGKANGQA) | ++ |
| 338 | F30L; A91R; Y139F; I166L; M230V; T297V; M309L; T317A; T334S; (334QTGHHQDPLQGKANGQA) | + |
| 340 | F30L; A91R; Y139F; I166L; M230V; M309L; T317A; T334S; (334QTGHHQDPLQGKANGQA) | + |
| 342 | F30L; A91R; Y139F; I166L; Y172C; L191I; M230V; M309L; T334S; (334QTGHHQDPLQGKANGQA) | + |
| 344 | F30L; A91R; Y139F; I166L; G200S; V203A; M230V; M309L; T317A; T334S; (334QTGHHQDPLQGKANGQA) | + |
| 346 | F30L; A91R; Y139F; I166L; M230V; T297V; M309L; T317A; T334S; (334QTGHHQDPLQGKANGQA) | + |
| 348 | S23T; F30L; A91R; Y139F; I166L; G200S; M230V; M309L; T334S; (334QTGHHQDPLQGKANGQA) | ++ |
| 350 | S23T; F30L; A91R; Y139F; I166L; M230V; M309L; T317A; T334S; (334QTGHHQDPLQGKANGQA) | ++ |
| 352 | F30L; W54Y; A91R; Y139F; I166L; M230V; M309L; T334S; (334QTGHHQDPLQGKANGQA) | +++ |
| 354 | F30L; A91R; Y139F; I166L; L191F; M230V; M309L; T334S; (334QTGHHQDPLQGKANGQA) | ++++ |
| 356 | F30L; A91R; Y139F; I166L; A173V; M230V; M309L; T332S; T334S; (334QTGHHQDPLQGKANGQA) | ++ |

[1]Relative Improvement (FIOP) scale: "+" indicates 1.1 to 1.5-fold improved; "++" indicates >1.5 to 2.0-fold improved; "+++" indicates >2.0 to 2.5-fold improved; and "++++" indicates >2.5-fold improved.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08614081B2). An electronic copy of the "Sequence Listing" will also be available from the USPTO upon request and payment of the fee set forth in 37 CFR 1.19(b)(3).

What is claimed is:

1. An engineered nitrilase polypeptide capable of converting the substrate of structural formula (I) to the product of structural formula (II):

$R^1$—CN ⟶ $R^1$—COOH
(I) (II)

wherein $R^1$ is a substituted or unsubstituted phenyl; a substituted or unsubstituted phenylalkyl($C_1$-$C_3$); a substituted or unsubstituted alkyl($C_3$-$C_8$) or a substituted or unsubstituted heteroalkyl, which polypeptide has improved stability to conditions of 3 hrs at 40° C. and/or 3 hrs in 10% methanol as compared to the polypeptide of SEQ ID NO:2, comprises an amino acid sequence that is at least 80% identical to the sequence of SEQ ID NO: 122 and comprises the following residue differences as compared to SEQ ID NO:2: X139 is F and X166 is L.

2. The engineered polypeptide of claim 1 in which the nitrilase has at least 5-fold improved thermostability as compared to SEQ ID NO:2 to the condition of 3 hrs at 40° C.

3. The engineered polypeptide of claim 1 in which the nitrilase has at least 5 fold improved solvent stability as compared to SEQ ID NO:2 to the condition of 3 hrs in 10% methanol.

4. The engineered polypeptide of claim 1 in which the nitrilase amino acid sequence includes one or more residue differences as compared to SEQ ID NO:2 at residue positions selected from: X91; X108; X230; X266; and X309.

5. The engineered polypeptide of claim 4 in which the amino acid residue at the residue positions are selected from: X91 is R or K; X108 is S, N or Q; X230 is Y, F, W, V, L, A, or I; X266 is V, L, A or I; and X309 is V, L, A or I.

6. The engineered polypeptide of claim 4 in which the amino acid residue at the residue positions are selected from: X91 is R; X108 is S; X230 is V; X266 is L; and X309 is L.

7. The engineered polypeptide of claim 4 in which the nitrilase polypeptide further has at least 1.1-fold improved activity for converting the substrate of formula I to the product of formula II relative to the activity of SEQ ID NO:2.

8. The engineered polypeptide of claim 7 in which the nitrilase amino acid sequence includes additionally one or more residue differences as compared to SEQ ID NO:2 at residue positions selected from: X23, X30, X37, X40, X49, X54, X55, X65, X73, X85, X121, X130, X132, X134, X152, X161, X163, X170, X171, X172, X173, X191, X197, X199, X200, X201, X203, X209, X217, X225, X230, X233, X240, X267, X269, X272, X282, X288, X289, X293, X295, X297, X303, X317, X319, X323, X327, X330, X332, and X334.

9. The engineered polypeptide of claim 8 in which the amino acid residue at the residue positions is selected from: X23 is T; X30 is L; X37 is T; X40 is E; X49 is V; X54 is M, V, A, F, or Y; X55 is F; X65 is T; X73 is E; X85 is R; X121 is K; X130 is R; X132 is H, M, L or F; X134 is A; X152 is T; X161 is N; X163 is H, W or G; X170 is G; X171 is R; X172 is C; X173 is V; X191 is A, C, I or F; X197 is L, M, or N; X199 is C, H, F, C, V, T, W, M, A, I, F or P; X200 is S; X201 is G; X203 is A; X209 is R; X217 is T; X225 is T; X230 is A, V or Y; X233 is T; X240 is R; X267 is A; X269 is R or P; X272 is E; X282 is I; X288 is T; X289 is V; X293 is T or V; X295 is N; X297 is G, A or V; X303 is P; X317 is A; X319 is M; X323 is G or K; X327 is V; X330 is I; X332 is I or S; and X334 is S, L or I.

10. The engineered polypeptide of claim 7 in which the nitrilase amino acid sequence includes additionally one or more residue differences as compared to SEQ ID NO:2 at residue positions selected from: X30, X54, X73, X132, X199, and X293.

11. The engineered polypeptide of claim 10 in which the amino acid residue at the residue positions is selected from the following: X30 is L; X54 is M, V, A, F, or Y; X132 is H, M, L or F; X199 is A, F, M, or C; and X293 is T or V.

12. The engineered polypeptide of claim 10 in which the nitrilase amino acid sequence includes additionally one or more residue differences as compared to SEQ ID NO:2 at residue positions selected from: X23, X37, X40, X49, X55, X65, X85, X121, X130, X134, X152, X161, X163, X170, X171, X172, X173, X191, X197, X200, X201, X203, X209, X217, X225, X233, X240, X267, X269, X272, X282, X288, X289, X295, X297, X303, X317, X319, X323, X327, X330, X332, and X334.

13. The engineered polypeptide of claim 12 in which the amino acid residue at the residue positions is selected from the following: X23 is T; X37 is T; X40 is E; X49 is V; X55 is F; X65 is T; X85 is R; X121 is K; X130 is R; X134 is A; X152 is T; X161 is N; X163 is W, H or G; X170 is G; X171 is R; X172 is C; X173 is V; X191 is I, A or C; X197 is M, L or N; X200 is S; X201 is G; X203 is A; X209 is R; X217 is T; X225 is T; X233 is T; X240 is R; X267 is A; X269 is R or P; X272 is E; X282 is I; X288 is T; X289 is V; X295 is N; X297 is V, G, or A; X303 is P; X317 is A; X319 is M; X323 is G or K; X327 is V; X330 is I; X332 is I or S; and X334 is S, I or A.

14. The engineered polypeptide of claim 1 in which the nitrilase amino acid sequence includes additionally 1 to 40 conservative amino acid residue differences as compared to SEQ ID NO:2 at other residue positions.

15. The engineered polypeptide of claim 14 in which the other residue positions are selected from: X7, X10, X13, X18, X20, X62, X119, X135, X185, X195, X228, X238, X242, X249, X259, X268, X270, X273, X277, X291, X308, X318, X324, X326, X328, X329, and X333.

16. The engineered polypeptide of claim 15 in which the amino acid residue at the other residue positions is selected from: X7 is E; X10 is A; X13 is G; X18 is L; X20 is L; X62 is V; X119 is V; X135 is H; X185 is P; X195 is E; X228 is R; X238 is A; X242 is A or G; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

17. The engineered polypeptide of claim 1 further comprising a carboxy terminal fusion to: (a) a polypeptide of SEQ ID NO: 378 or 380 or (b) at least a continuous segment of 17 amino acids of SEQ ID NO: 378 or 380.

18. The engineered polypeptide of claim 1 in which the nitrilase amino acid sequence is selected from the sequence of SEQ ID NO: 4, 6, 8, 10, 12, 14, 16, 18, 20, 22, 24, 26, 28, 78, 98, 108, 110, 112, 122, 124, 126, 128, 138, 144, 146, 148, 150, 152, 154, 156, 158, 160, 162, 164, 166, 168, 170, 172, 174, 176, 178, 180, 184, 188, 190, 200, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 362, 364, 366, 368, and 370.

19. The engineered polypeptide of claim 1 in which nitrilase is further capable of converting the substrate of formula I to the substrate of formula II with at least 1.1 fold activity relative to the activity of SEQ ID NO:2, wherein (A) the substrate of formula I is IA:

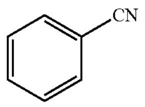

(Ia)

and product of formula II is IIa:

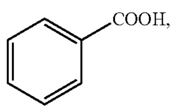

(IIa)

(B) the substrate of formula I is IB:

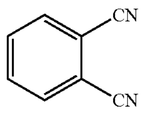

(Ib)

and the product of formula II is IIb:

(IIB)

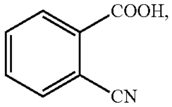

(C) substrate of formula I is IC:

(IC)

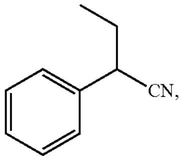

and the product of formula II is IIc':

(IIc')

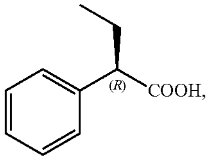

and IIc'':

(IIC'')

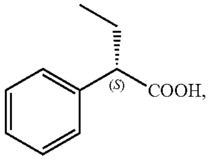

(D) substrate of formula I is ID:

(Id)

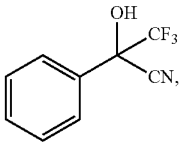

and the product of formula II is IId':

(IId')

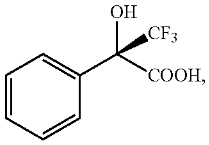

and IId'':

(IId'')

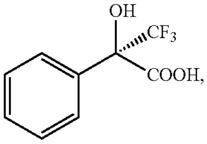

(E) substrate of formula I is IE:

(Ie)

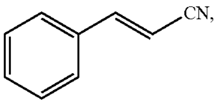

and the product of formula II is IIe':

(IIE')

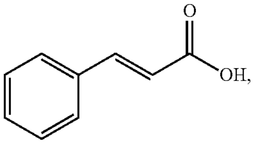

(F) substrate of formula I is IF:

(IF)

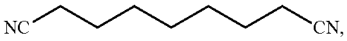

and the product of formula II is IIf:

(IIf)

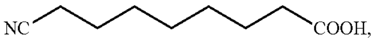

(G) substrate of formula I is IG:

(Ig)

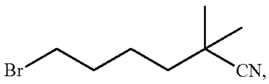

and the product of formula II is IIg:

(IIg)

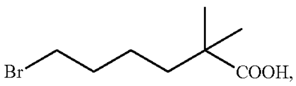

(h) substrate of formula I is Ih:

(Ih)

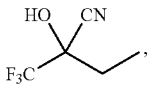

and the product of formula II is IIh:

(IIh)

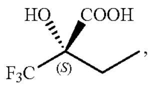

(i) substrate of formula I is Ii:

(Ii)

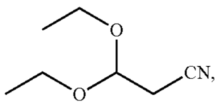

and the product of formula II is IIi:

(IIi)

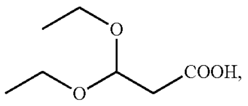

or (j) substrate of formula I is Ij:

(Ij)

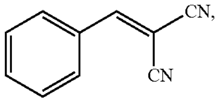

and the product of formula II is IIj:

(IIj)

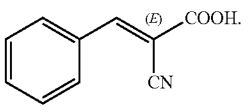

20. The polypeptide of claim 19 in which for the substrate Ie, the polypeptide is capable of also forming the amide product of IIe":

(IIe")

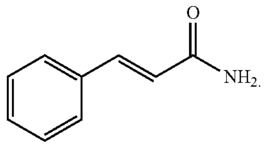

21. The engineered polypeptide of claim 19 in which the substrate is Ia and the product is IIa, wherein the nitrilase amino acid sequence includes additionally one or more residue differences as compared to SEQ ID NO:2 at residue positions selected from: X30, X54, X161, X163, X191, X197, X199, X230, X242, X269, X293, and X334.

22. The polypeptide of claim 21 in which the amino acid residue at the residue positions are selected from: X30 is L; X54 is F, M, V or A; X161 is N; X163 is W or H; X191 is I, A or C; X197 is L, M, or N; X199 is C, H, F, C, V, T, W, M, A, I or F; X230 is A or Y; X238 is A; X242 is A; X269 is R; X293 is T; and X334 is I, S or L.

23. The polypeptide of claim 21 in which the nitrilase amino acid sequence is selected from SEQ ID NOS: 4, 8, 10, 12, 14, 16, 18, 22, 144, 150, 152, 156, 158, 160, 162, 166, 168, 170, 172, 174, 176, 206, 208, 216, and 218.

24. The polypeptide of claim 19 in which the nitrilase amino acid sequence includes additionally one or more residue differences as compared to SEQ ID NO:2 at residue positions selected from: X23, X37, X40, X49, X55, X65, X73, X85, X121, X130, X132, X134, X152, X170, X171, X172, X173, X200, X201, X203, X209, X217, X225, X233, X240, X267, X272, X282, X288, X289, X295, X297, X303, X317, X319, X323, X327, X330, and X332.

25. The engineered polypeptide of claim 24 in which the amino acid residue for the residue positions is selected from: X23 is T; X37 is T; X40 is E; X49 is V; X55 is F; X65 is T; X73 is E; X85 is R; X121 is K; X130 is R; X132 is F, H, M, or L; X134 is A; X152 is T; X170 is G; X171 is R; X172 is C; X173 is V; X200 is S; X201 is G; X203 is A; X209 is R; X217 is T; X225 is T; X233 is T; X240 is R; X267 is A; X272 is E; X282 is I; X288 is T; X289 is V; X295 is N; X297 is V, G, or A; X303 is P; X317 is A; X319 is M; X323 is G or K; X327 is V; X330 is I; and X332 is I or S.

26. The engineered polypeptide of claim 19 in which the nitrilase amino acid sequence includes additionally 1 to 40 conservative amino acid residue differences as compared to SEQ ID NO:2 at other residue positions.

27. The engineered polypeptide of claim 26 in which the other residue positions are selected from: X7, X10, X13, X18, X20, X62, X119, X135, X185, X195, X228, X249, X259, X268, X270, X273, X277, X291, X308, X318, X324, X326, X328, X329, and X333.

28. The engineered polypeptide of claim 27 in which the amino acid residue at the other residue positions is selected from: X7 is E; X10 is A; X13 is G; X18 is L; X20 is L; X62 is V; X119 is V; X135 is H; X185 is P; X195 is E; X228 is R; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

29. The polypeptide of claim 19 in which the substrate is Ib and the product is IIb, and wherein the nitrilase amino acid sequence includes additionally one or more amino acid residue differences as compared to SEQ ID NO:2 at residue positions selected from: X23, X54, X65, X73, X121, X132, X134, X161, X163, X171, X172, X197, X199, X200, X201, X203, X209, X217, X233, X240, X293, X297, X317, and X330.

30. The polypeptide of claim 29 in which amino acid residues at the residue positions are selected from: X23 is T; X54 is M, F, V, or A; X65 is T; X73 is E; X121 is K; X132 is F; X134 is A; X161 is N; X163 is G; X171 is R; X172 is C; X197 is M; X199 is C, F or M; X200 is S; X201 is G; X203 is A; X209 is R; X217 is T; X233 is T; X240 is R; X293 is T; X297 is V; X317 is A; and X330 is I.

31. The polypeptide of claim 29 in which the nitrilase amino acid sequence includes additionally one or more residue differences as compared to SEQ ID NO:2 at residue positions selected from: X30, X37, X40, X49, X55, X85, X130, X152, X170, X173, X191, X225, X267, X269, X272, X282, X288, X289, X295, X303, X319, X323, X327, X332, and X334.

32. The polypeptide of claim 31 in which the amino acid residues at the residue positions are selected from: X30 is L; X37 is T; X40 is E; X49 is V; X55 is F; X85 is R; X130 is R; X152 is T; X170 is G; X173 is V; X191 is I, A or C; X225 is T; X267 is A; X269 is R or P; X272 is E; X282 is I; X288 is T; X289 is V; X295 is N; X303 is P; X319 is M; X323 is G or K; X327 is V; X332 is I or S; and X334 is S, I or A.

33. The engineered polypeptide of claim 29 in which the nitrilase amino acid sequence additionally includes 1 to 40 conservative amino acid residue differences as compared to SEQ ID NO:2 at other residue positions.

34. The engineered polypeptide of claim 33 in which the other residue positions are selected from: X7, X10, X13, X18, X20, X62, X119, X135, X185, X195, X228, X238, X242, X249, X259, X268, X270, X273, X277, X291, X308, X318, X324, X326, X328, X329, and X333.

35. The engineered polypeptide of claim 34 in which the amino acid residue at the other residue positions is selected from: X7 is E; X10 is A; X13 is G; X18 is L; X20 is L; X62 is V; X119 is V; X135 is H; X185 is P; X195 is E; X228 is R; X238 is A; X242 is A or G; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

36. The engineered polypeptide of claim 29 in which the nitrilase amino acid sequence is selected from SEQ ID NO: 178, 180, 190, 220, 222, 224, 226, 228, 232, 234, 236, 238, 240, 242, 244, 246, 248, 250, 252, 254, 256, 258, 260, 262, 264, 266, 268, 270, 272, 274, 276, 278, 282, 284, 288, 290, 292, 296, or 300.

37. The engineered polypeptide of claim 19 in which the substrate is Ic and the product is IIc' and IIc", wherein the nitrilase amino acid sequence includes additionally one or more residue differences as compared to SEQ ID NO:2 at residue positions selected from: X30, X54, X65, X132, X163, X172, X191, X197, X199, X225, X238; X293, X332, and X334.

38. The engineered polypeptide of claim 37 in which the amino acid residue at the residue positions is selected from: X30 is L; X54 is F or M; X65 is T; X132 is H, M, L or F; X163 is G; X172 is C; X191 is I; X197 is L; X199 is C; X225 is T; X238 is A; X293 is T; X332 is I; and X334 is I, L or S.

39. The engineered polypeptide of claim 37 in which the nitrilase amino acid sequence additionally includes one or more residue differences as compared to SEQ ID NO:2 at residue positions selected from: X23, X37, X40, X49, X55, X73, X85, X121, X130, X134, X152, X161, X170, X171, X173, X200, X201, X203, X209, X217, X233, X240, X267, X269, X272, X282, X288, X289, X295, X297, X303, X317, X319, X323, X327, and X330.

40. The engineered polypeptide of claim 39 in which the amino acid residue at the residue positions is selected from: X23 is T; X37 is T; X40 is E; X49 is V; X55 is F; X73 is E; X85 is R; X121 is K; X130 is R; X134 is A; X152 is T; X161 is N; X170 is G; X171 is R; X173 is V; X200 is S; X201 is G; X203 is A; X209 is R; X217 is T; X233 is T; X240 is R; X267 is A; X269 is R or P; X272 is E; X282 is I; X288 is T; X289 is V; X295 is N; X297 is V, G, or A; X303 is P; X317 is A; X319 is M; X323 is G or K; X327 is V; and X330 is I.

41. The engineered polypeptide of claim 37 in which the nitrilase amino acid sequence additionally includes 1 to 40 conservative amino acid residue differences as compared to SEQ ID NO:2 at other residue positions.

42. The engineered polypeptide of claim 41 in which the other residue positions are selected from: X7, X10, X13, X18, X20, X62, X119, X135, X185, X195, X228, X242, X249, X259, X268, X270, X273, X277, X291, X308, X318, X324, X326, X328, X329, and X333.

43. The engineered polypeptide of claim 42 in which the amino acid residue at the other residue positions is selected from: X7 is E; X10 is A; X13 is G; X18 is L; X20 is L; X62 is V; X119 is V; X135 is H; X185 is P; X195 is E; X228 is R; X242 is A or G; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

44. The polypeptide of claim 37 in which the nitrilase amino acid sequence is selected from SEQ ID NO: 4, 8, 10, 14, 20, 24, 28, 154, 174, 210, 212, 214, 250, 256, 270, 276, 284, 288, 298, 300, 302, 304, 308, 310, 312, 316, and 318.

45. The engineered polypeptide of claim 19 in which the substrate is Ic, and the polypeptide is further capable of producing product IIc" in enantiomeric excess of product IIc'.

46. The engineered polypeptide of claim 45 in which the amino acid sequence comprises one or more residue differences as compared to SEQ ID NO:2 selected from: X54 is F or M; X132 is H, M, or L; X163 is G, and X293 is T.

47. The engineered polypeptide of claim 45 in which the nitrilase polypeptide comprises an amino acid sequence selected from SEQ ID NO: 20, 24, 210, 212, 214, 250, 252, 254, 256, 258, 260, 262, 264, 268, 270, 276, 278, 280, 282, 284, 286, 288, 290, 292, 294, 296, 300, 304, 306, 308, 310 and 314.

48. The engineered polypeptide of claim 19 in which the substrate is Ic, and the polypeptide is further capable of producing product IIc' in enantiomeric excess of product IIc".

49. The engineered polypeptide of claim 48 in which the amino acid sequence comprises at least one or more residue differences as compared to SEQ ID NO:2 selected from: X54 is A; X139 is W; X163 is W; X171 is R; X197 is L or N; X199 is A; X203 is A; X267 is A; and X269 is P.

50. The engineered polypeptide of claim 48 in which the nitrilase polypeptide comprises an amino acid sequence selected from SEQ ID NO: 26, 146, 152, 156, 176, 178, 190, 216, 218 or 320.

51. The polypeptide of claim 19 in which the substrate is Id and the product is IId' and IId", wherein the nitrilase amino acid sequence includes additionally one or more residue differences as compared to SEQ ID NO:2 at residue positions selected from: X23, X30, X37, X40, X54, X73, X85, X130, X132, X134, X161, X163, X170, X172, X191, X197, X199, X200, X201, X203, X209, X269, X272, X289, X293, X297, X327, X330, and X334.

52. The polypeptide of claim 51 in which the amino acid residue at the residue positions is selected from: X23 is T; X30 is L; X37 is T; X40 is E; X54 is M; X73 is E; X85 is R; X130 is R; X132 is H; X134 is A; X161 is N; X163 is G; X170 is G; X172 is C; X191 is I; X197 is L; X199 is M or F; X200 is S; X201 is G; X203 is A; X209 is R; X269 is P; X272 is E; X289 is V; X293 is T; X297 is V; X327 is V; X330 is I; and X334 is I, S, or L.

53. The polypeptide of claim 51 in which the nitrilase amino acid sequence includes additionally one or more residue differences as compared to SEQ ID NO:2 at residue positions selected from: X49, X55, X65, X121, X152, X171, X173, X217, X225, X233, X240, X267, X282, X288, X295, X303, X317, X319, X323, and X332.

54. The engineered polypeptide of claim 53 in which the amino acid residues at the residues positions are selected from: X49 is V; X55 is F; X65 is T; X121 is K; X152 is T; X171 is R; X173 is V; X217 is T; X225 is T; X233 is T; X240 is R; X267 is A; X282 is I; X288 is T; X295 is N; X303 is P; X317 is A; X319 is M; X323 is G or K; and X332 is I or S.

55. The engineered polypeptide of claim 51 in which the nitrilase amino acid sequence additionally includes 1 to 40 conservative amino acid residue differences as compared to SEQ ID NO:2 at other residue positions.

56. The engineered polypeptide of claim 55 in which the other residue positions are selected from: X7, X10, X13, X18, X20, X62, X119, X135, X185, X195, X228, X238, X242, X249, X259, X268, X270, X273, X277, X291, X308, X318, X324, X326, X328, X329, and X333.

57. The engineered polypeptide of claim 56 in which the amino acid residue at the other residue positions is selected from: X7 is E; X10 is A; X13 is G; X18 is L; X20 is L; X62 is V; X119 is V; X135 is H; X185 is P; X195 is E; X228 is R; X238 is A; X242 is A or G; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

58. The engineered polypeptide of claim 51 in which the nitrilase amino acid sequence is selected from SEQ ID NO: 4, 10, 14, 22, 28, 180, 184, 188, 192, 194, 196, 200, 210, 220, 222, 226, 230, 238, 266, 304, 310, and 314.

59. The engineered polypeptide of claim 19 in which the substrate is Id, and the polypeptide is further capable of producing product IId' in enantiomeric excess of product IId".

60. The engineered polypeptide of claim 59 in which the amino acid sequence comprises at least one or more residue differences as compared to SEQ ID NO:2 selected from: X132 is F, X163 is G, and X230 is Y.

61. The engineered polypeptide of claim 59 in which the nitrilase polypeptide comprises an amino acid sequence selected from SEQ ID NO: 20, 24, and 206.

62. The engineered polypeptide of claim 19 in which the substrate is Ie and the product is IIe', wherein the nitrilase amino acid sequence includes additionally one or more residue differences as compared to SEQ ID NO:2 at residue positions selected from: X23, X30, X37, X49, X54, X65, X121, X134, X161, X163, X197; X199; X200; X201; X209; X240; X269; X293; X317; X323; X332; and X334.

63. The polypeptide of claim 62 in which the amino acid residue at the residue positions is selected from: X23 is T; X30 is L; X37 is T; X49 is V; X54 is M, F, V or A; X65 is T; X121 is K; X134 is A; X161 is N; X163 is G; X197 is L, M or N; X199 is F, H, C, V, T, W, P, M, A, or I; X200 is S; X201 is G; X209 is R; X240 is R; X269 is R; X293 is T; X317 is A; X323 is G; X332 is I; and X334 is I, S or L.

64. The engineered polypeptide of claim 62 in which the nitrilase amino acid sequence includes additionally one or more residue differences as compared to SEQ ID NO:2 at residue positions selected from: X40, X55, X73, X85, X130, X132, X152, X170, X171, X172, X173, X191, X203, X217, X225, X233, X267, X272, X282, X288, X289, X295, X297, X303, X319, X327, and X330.

65. The engineered polypeptide of claim 64 in which the amino acid residues at the residues positions are selected from: X40 is E; X55 is F; X73 is E; X85 is R; X130 is R; X132 is F, H, M, or L; X152 is T; X170 is G; X171 is R; X172 is C; X173 is V; X191 is I, A or C; X203 is A; X217 is T; X225 is T; X233 is T; X267 is A; X272 is E; X282 is I; X288 is T; X289 is V; X295 is N; X297 is V, G, or A; X303 is P; X319 is M; X327 is V; and X330 is I.

66. The engineered polypeptide of claim 62 in which the nitrilase amino acid sequence additionally includes 1 to 40 conservative amino acid residue differences as compared to SEQ ID NO:2 at other residue positions.

67. The engineered polypeptide of claim 66 in which the other residue positions are selected from: X7, X10, X13, X18, X20, X62, X119, X135, X185, X195, X228, X238, X242, X249, X259, X268, X270, X273, X277, X291, X308, X318, X324, X326, X328, X329, and X333.

68. The engineered polypeptide of claim 67 in which the amino acid residue at the other residue positions is selected from: X7 is E; X10 is A; X13 is G; X18 is L; X20 is L; X62 is V; X119 is V; X135 is H; X185 is P; X195 is E; X228 is R; X238 is A; X242 is A or G; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

69. The engineered polypeptide of claim 62 in which the nitrilase amino acid sequence is selected from SEQ ID NO: 4, 8, 10, 12, 14, 22, 144, 146, 148, 150, 152, 154, 156, 158, 160, 162, 164, 166, 168, 170, 172, 174, 176, 180, 190, 206, 216, 220, 222, 224, 226, 228, 230, 232, 234, 236, 238, 240, 242, 244, 246, 248, 250, 266, 274, 278, 282, 284, 288, 290 and 296.

70. The engineered polypeptide of claim 19 in which the nitrilase is capable of converting the substrate Ie to the products IIe' and IIe", and wherein the nitrilase amino acid sequence includes additionally one or more residue differences as compared to SEQ ID NO:2 at residue positions selected from: X23, X37, X40, X49, X54, X65, X85, X121, X134, X139, X161, X163, X172, X191, X197, X199, X200, X272, X289, X293, X297, X319, X323, X332, and X334.

71. The polypeptide of claim 70 in which the amino acid residue at the residue positions is selected from: X23 is T; X37 is T; X40 is E; X49 is V; X54 is M, F, or V; X65 is T; X85 is R; X121 is K; X134 is A; X139 is W; X161 is N; X163 is G; X172 is C; X191 is I; X197 is L; X199 is F, C, M or A; X200 is S; X272 is E; X289 is V; X293 is T; X297 is V; X319 is M; X323 is G; X332 is I; and X334 is I.

72. The engineered polypeptide of claim 70 in which the nitrilase amino acid sequence includes additionally one or more residue differences as compared to SEQ ID NO:2 at residue positions selected from: X30, X55, X73, X130, X132, X152, X170, X171, X173, X201, X203, X209, X217, X225, X233, X240, X267, X269, X282, X288, X295, X303, X317, X327, and X330.

73. The engineered polypeptide of claim 72 in which the amino acid residues at the residues positions are selected from: X30 is L; X55 is F; X73 is E; X130 is R; X132 is F, H, M, or L; X152 is T; X170 is G; X171 is R; X173 is V; X201 is G; X203 is A; X209 is R; X217 is T; X225 is T; X233 is T; X240 is R; X267 is A; X269 is R or P; X282 is I; X288 is T; X295 is N; X303 is P; X317 is A; X327 is V; and X330 is I.

74. The engineered polypeptide of claim 70 in which the nitrilase amino acid sequence additionally includes 1 to 40 conservative amino acid residue differences as compared to SEQ ID NO:2 at other residue positions.

75. The engineered polypeptide of claim 74 in which the other residue positions are selected from: X7, X10, X13, X18, X20, X62, X119, X135, X185, X195, X228, X238, X242, X249, X259, X268, X270, X273, X277, X291, X308, X318, X324, X326, X328, X329, and X333.

76. The engineered polypeptide of claim 75 in which the amino acid residue at the other residue positions is selected from: X7 is E; X10 is A; X13 is G; X18 is L; X20 is L; X62 is V; X119 is V; X135 is H; X185 is P; X195 is E; X228 is R; X238 is A; X242 is A or G; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

77. The engineered polypeptide of claim 70 in which the nitrilase amino acid sequence is selected from SEQ ID NO: 22, 24, 28, 180, 200, 216, 220, 226, 230, 232, 236, 238, 248, 250, 274, 278, 282, 284, 288, 290, 296, 302, 306, 316, and 318.

78. The engineered polypeptide of claim 19 in which the substrate is If and the product is IIf, and wherein the nitrilase amino acid sequence includes additionally a residue difference as compared to SEQ ID NO:2 at residue position X332.

79. The engineered polypeptide of claim 78 in which the amino acid residue at the residue position X332 is I.

80. The engineered polypeptide of claim 78 in which the nitrilase amino acid sequence includes additionally one or more residue differences as compared to SEQ ID NO:2 at residue positions selected from: X23, X30, X37, X40, X49, X54, X55, X65, X73, X85, X121, X130, X132, X134, X152, X161, X163, X170, X171, X172, X173, X191, X197, X199, X200, X201, X203, X209, X217, X225, X233, X240, X267, X269, X272, X282, X288, X289, X293, X295, X297, X303, X317, X319, X323, X327, X330, and X334.

81. The engineered polypeptide of claim 80 in which the amino acid residues at the residues positions are selected from: X23 is T; X30 is L; X37 is T; X40 is E; X49 is V; X54 is V, M, F or A; X55 is F; X65 is T; X73 is E; X85 is R; X121 is K; X130 is R; X132 is F, H, M, or L; X134 is A; X152 is T; X161 is N; X163 is W, H or G; X170 is G; X171 is R; X172 is C; X173 is V; X191 is I, A or C; X197 is M, L or N; X199 is C, F, M, W, P, A, I, V, T, or H; X200 is S; X201 is G; X203 is A; X209 is R; X217 is T; X225 is T; X233 is T; X240 is R; X267 is A; X269 is R or P; X272 is E; X282 is I; X288 is T; X289 is V; X293 is T or V; X295 is N; X297 is V, G, or A; X303 is P; X317 is A; X319 is M; X323 is G or K; X327 is V; X330 is I; and X334 is S, I or A.

82. The engineered polypeptide of claim 78 in which the nitrilase amino acid sequence additionally includes 1 to 40 conservative amino acid residue differences as compared to SEQ ID NO:2 at other residue positions.

83. The engineered polypeptide of claim 82 in which the other residue positions are selected from: X7; X10; X13; X18; X20; X62; X119; X135; X185; X195; X228; X238; X242; X249; X259; X268; X270; X273; X277; X291; X308; X318; X324; X326; X328; X329; and X333.

84. The engineered polypeptide of claim 83 in which the amino acid residue at the other residue positions is selected from: X7 is E; X10 is A; X13 is G; X18 is L; X20 is L; X62 is V; X119 is V; X135 is H; X185 is P; X195 is E; X228 is R; X238 is A; X242 is A or G; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

85. The polypeptide of claim 78 in which the nitrilase amino acid sequence is selected from SEQ ID NO: 154.

86. The engineered polypeptide of claim 19 in which the substrate is Ig and the product is IIg, and wherein the nitrilase amino acid sequence includes additionally one or more residue difference as compared to SEQ ID NO:2 at residue positions selected from: X30, X49, X54, X121, X161, X191, X199, X225, X293, X332, and X334.

87. The polypeptide of claim 86 in which the amino acid residue at the residue positions is selected from: X30 is L; X49 is V; X54 is F, V, A, or M; X121 is K; X161 is N; X191 is I; X199 is M; X225 is T; X293 is T; X332 is I; and X334 is S, L or I.

88. The engineered polypeptide of claim 86 in which the nitrilase amino acid sequence includes additionally one or more residue differences as compared to SEQ ID NO:2 at residue positions selected from: X23, X37, X40, X55, X65, X73, X85, X130, X132, X134, X152, X163, X170, X171, X172, X173, X197, X200, X201, X203, X209, X217, X233, X240, X267, X269, X272, X282, X288, X289, X295, X297, X303, X317, X319, X323, X327, and X330.

89. The engineered polypeptide of claim 88 in which the amino acid residues at the residues positions are selected from: X23 is T; X37 is T; X40 is E; X55 is F; X65 is T; X73 is E; X85 is R; X130 is R; X132 is F, H, M, or L; X134 is A; X152 is T; X163 is W, H or G; X170 is G; X171 is R; X172 is C; X173 is V; X197 is M, L or N; X200 is S; X201 is G; X203 is A; X209 is R; X217 is T; X233 is T; X240 is R; X267 is A; X269 is R or P; X272 is E; X282 is I; X288 is T; X289 is V; X295 is N; X297 is V, G, or A; X303 is P; X317 is A; X319 is M; X323 is G or K; X327 is V; and X330 is I.

90. The engineered polypeptide of claim 86 in which the nitrilase amino acid sequence additionally includes 1 to 40 conservative amino acid residue differences as compared to SEQ ID NO:2 at other residue positions.

91. The engineered polypeptide of claim 90 in which the other residue positions are selected from: X7, X10, X13, X18, X20, X62, X119, X135, X185, X195, X228, X238, X242, X249, X259, X268, X270, X273, X277, X291, X308, X318, X324, X326, X328, X329, and X333.

92. The engineered polypeptide of claim 91 in which the amino acid residue at the other residue positions is selected from: X7 is E; X10 is A; X13 is G; X18 is L; X20 is L; X62 is V; X119 is V; X135 is H; X185 is P; X195 is E; X228 is R; X238 is A; X242 is A or G; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

93. The engineered polypeptide of claim 86 in which the nitrilase amino acid sequence is selected from SEQ ID NO: 4, 14, 22, 28, 180, 184, 188, 200, 210, 220, 222, 226, 230, 238, 266, 304, 310 and 314.

94. The polypeptide of claim 19 in which the substrate is Ih and the product is IIh, wherein the nitrilase amino acid sequence has one or more residue differences as compared to SEQ ID NO:2 at residue positions selected from: X23, X30, X54, X55, X152, X172, X173, X191, X200, X203, X282, X293, X295, X297, X303, X317, X323, and X332.

95. The polypeptide of claim 94 in which the amino acid residue at the residue positions are selected from: X23 is T; X30 is L; X54 is Y; X55 is F; X152 is T; X172 is C; X173 is V; X191 is F; X200 is S; X203 is A; X282 is I; X293 is T; X295 is N; X297 is V; X303 is P; X317 is A; X323 is K; and X332 is S.

96. The engineered polypeptide of claim 94 in which the nitrilase amino acid sequence includes additionally one or more residue differences as compared to SEQ ID NO:2 at residue positions selected from: X37, X40, X49, X65, X73, X85, X121, X130, X132, X134, X161, X163, X170, X171, X197, X199, X201, X209, X217, X225, X233, X240, X267, X269, X272, X288, X289, X319, X327, X330, and X334.

97. The engineered polypeptide of claim 96 in which the amino acid residues at the residues positions are selected from: X37 is T; X40 is E; X49 is V; X65 is T; X73 is E; X85 is R; X121 is K; X130 is R; X132 is F, H, M, or L; X134 is A; X161 is N; X163 is W, H or G; X170 is G; X171 is R; X197 is M, L or N; X199 is C, F, M, W, P, A, I, V, T, or H; X201 is G; X209 is R; X217 is T; X225 is T; X233 is T; X240 is R; X267 is A; X269 is R or P; X272 is E; X288 is T; X289 is V; X319 is M; X327 is V; X330 is I; and X334 is S, I or A.

98. The engineered polypeptide of claim 94 in which the nitrilase amino acid sequence additionally includes 1 to 40 conservative amino acid residue differences as compared to SEQ ID NO:2 at other residue positions.

99. The engineered polypeptide of claim 98 in which the other residue positions are selected from: X7, X10, X13, X18, X20, X62, X119, X135, X185, X195, X228, X238, X242, X249, X259, X268, X270, X273, X277, X291, X308, X318, X324, X326, X328, X329, and X333.

100. The engineered polypeptide of claim 99 in which the amino acid residue at the other residue positions is selected from: X7 is E; X10 is A; X13 is G; X18 is L; X20 is L; X62 is V; X119 is V; X135 is H; X185 is P; X195 is E; X228 is R; X238 is A; X242 is A or G; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

101. The engineered polypeptide of claim 94 in which the nitrilase amino acid sequence is selected from SEQ ID NO: 322, 324, 326, 342, 328, 330, 332, 334, 336, 344, 346, 338, 348, 350, 340, 352, 354 and 356.

102. The engineered polypeptide of claim 19 in which the substrate is Ii and the product is IIi, wherein the nitrilase amino acid sequence has one or more residue differences as compared to SEQ ID NO:2 at residue positions selected from: X23, X37, X49, X54, X131, X134, X161, X163, X199, X200, X240, X288, X293, and X297.

103. The engineered polypeptide of claim 102 in which the amino acid residue at the residue positions are selected from: X23 is T; X37 is T; X49 is V; X54 is A, V, M or F; X131 is K; X134 is A; X161 is N; X163 is G; X199 is M, C or F; X200 is S; X240 is R; X288 is T; X293 is T; and X297 is V.

104. The engineered polypeptide of claim 102 in which the nitrilase amino acid sequence includes additionally one or more residue differences as compared to SEQ ID NO:2 at residue positions selected from: X30, X40, X55, X65, X73, X85, X121, X130, X132, X152, X170, X171, X172, X173, X191, X197, X201, X203, X209, X217, X225, X233, X267, X269, X272, X282, X289, X295, X303, X317, X319, X323, X327, X330, X332, and X334.

105. The engineered polypeptide of claim 104 in which the amino acid residues at the residues positions are selected from: X30 is L; X40 is E; X55 is F; X65 is T; X73 is E; X85 is R; X121 is K; X130 is R; X132 is F, H, M, or L; X152 is T; X170 is G; X171 is R; X172 is C; X173 is V; X191 is I, A or C; X197 is M, L or N; X201 is G; X203 is A; X209 is R; X217 is T; X225 is T; X233 is T; X267 is A; X269 is R or P; X272 is E; X282 is I; X289 is V; X295 is N; X303 is P; X317 is A; X319 is M; X323 is G or K; X327 is V; X330 is I; X332 is I or S; and X334 is S, I or A.

106. The engineered polypeptide of claim 102 in which the nitrilase amino acid sequence additionally includes 1 to 40 conservative amino acid residue differences as compared to SEQ ID NO:2 at other residue positions.

107. The engineered polypeptide of claim 106 in which the other residue positions are selected from: X7, X10, X13, X18, X20, X62, X119, X135, X185, X195, X228, X238, X242, X249, X259, X268, X270, X273, X277, X291, X308, X318, X324, X326, X328, X329, and X333.

108. The engineered polypeptide of claim 107 in which the amino acid residue at the other residue positions is selected from: X7 is E; X10 is A; X13 is G; X18 is L; X20 is L; X62 is V; X119 is V; X135 is H; X185 is P; X195 is E; X228 is R; X238 is A; X242 is A or G; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

109. The engineered polypeptide of claim 102 in which the nitrilase amino acid sequence is selected from SEQ ID NO: 180, 220, 226, 228, 230, 232, 234, 236, 238, 240, 242, 244, 246, 248, 266, 274, 278, 282, and 284.

110. The engineered polypeptide of claim 19 in which the nitrilase is capable of converting the substrate Ij to the product IIj, and wherein the nitrilase amino acid sequence includes additionally one or more residue differences as compared to SEQ ID NO:2 at residue positions selected from: X119, X161, X163, X199, AND X242.

111. The polypeptide of claim 110 in which the amino acid residue at the residue positions is selected from: X119 is V; X161 is N; X163 is G; X199 is A; and X242 is A.

112. The engineered polypeptide of claim 110 in which the nitrilase amino acid sequence includes additionally one or more residue differences as compared to SEQ ID NO:2 at residue positions selected from: X23; X30; X37; X40; X49; X54; X55; X65; X73; X85; X121; X130; X132; X134; X152; X170; X171; X172; X173; X191; X197; X200; X201; X203; X209; X217; X225; X233; X240; X267; X269; X272; X282; X288; X289; X293; X295; X297; X303; X317; X319; X323; X327; X330; X332; and X334.

113. The engineered polypeptide of claim 112 in which the amino acid residues at the residues positions are selected from: X23 is T; X30 is L; X37 is T; X40 is E; X49 is V; X54 is V, M, F or A; X55 is F; X65 is T; X73 is E; X85 is R; X121 is K; X130 is R; X132 is F, H, M, or L; X134 is A; X152 is T; X170 is G; X171 is R; X172 is C; X173 is V; X191 is I, A or C; X197 is M, L or N; X200 is S; X201 is G; X203 is A; X209 is R; X217 is T; X225 is T; X233 is T; X240 is R; X267 is A; X269 is R or P; X272 is E; X282 is I; X288 is T; X289 is V; X293 is T or V; X295 is N; X297 is V, G, or A; X303 is P; X317 is A; X319 is M; X323 is G or K; X327 is V; X330 is I; X332 is I or S; and X334 is S, I or A.

114. The engineered polypeptide of claim 110 in which the nitrilase amino acid sequence additionally includes 1 to 40 conservative amino acid residue differences as compared to SEQ ID NO:2 at other residue positions.

115. The engineered polypeptide of claim 114 in which the other residue positions are selected from: X7, X10, X13, X18, X20, X62, X135, X185, X195, X228, X238, X249, X259, X268, X270, X273, X277, X291, X308, X318, X324, X326, X328, X329, and X333.

116. The engineered polypeptide of claim 115 in which the amino acid residue at the other residue positions is selected from: X7 is E; X10 is A; X13 is G; X18 is L; X20 is L; X62 is V; X119 is V; X135 is H; X185 is P; X195 is E; X228 is R; X238 is A; X242 is A or G; X249 is E or V; X259 is I; X268 is K; X270 is P; X273 is A; X277 is L; X291 is E; X308 is P or R; X318 is Y; X324 is N; X326 is Y; X328 is P; X329 is I; and X333 is A.

117. The engineered polypeptide of claim 1 in which nitrilase is capable of converting the substrate of formula Ik:

(Ik)

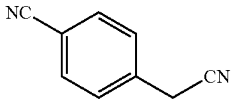

to the product of formula IIk'

(IIk')

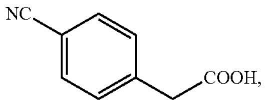

and IIk';

(IIk")

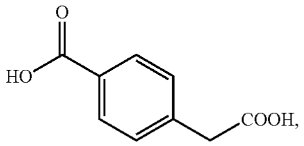

wherein the nitrilase amino acid sequence has one or more residue differences as compared to SEQ ID NO:2 at residue positions selected from: X54, X163, X191, and X242.

118. The engineered polypeptide of claim 117 in which the amino acid residue at the residue positions are selected from: X54 is M; X163 is G; X191 is I and X242 is A.

119. The engineered polypeptide of claim 1 in which the nitrilase has at least 10 fold improved thermostability as compared to SEQ ID NO:2 to the condition of 3 hrs at 40° C.

120. The engineered polypeptide of claim 119 in which the nitrilase comprises an amino acid sequence selected from SEQ ID NO: 6, or 362.

121. The engineered polypeptide of claim 1 in which the nitrilase has at least 10 fold improved solvent stability as compared to SEQ ID NO:2 to the condition of 3 hrs in 10% methanol.

122. The engineered polypeptide of claim 121 in which the nitrilase comprises an amino acid sequence selected from SEQ ID NO: 6, or 362.

123. A recombinant polynucleotide encoding the engineered nitrilase polypeptide of claim 1.

124. The polynucleotide of claim 123 in which the polynucleotide sequence is selected from SEQ ID NO:3, 5, 7, 9, 11, 13, 15, 17, 19, 21, 23, 25, 27, 77, 97, 107, 109, 111, 121, 123, 125, 127, 137, 143, 145, 147, 149, 151, 153, 155, 157, 159, 161, 163, 165, 167, 169, 171, 173, 175, 177, 179, 183, 187, 189, 199, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 361, 363, 365, 367, and 369.

125. An expression vector of the polynucleotide of claim 123.

126. The expression vector of claim 125, comprising a control sequence.

127. The expression vector of claim 126 in which the control sequence is a promoter.

128. A host cell comprising the expression vector of claim 125.

129. A method for preparing an engineered nitrilase polypeptide of claim 1 comprising culturing a host cell comprising an expression vector encoding a nitrilase polypeptide and recovering the polypeptide from the cell or the culture medium.

130. A process for converting the substrate compound of formula I to the product of formula II:

$$\underset{(I)}{R^1\text{—CN}} \longrightarrow \underset{(II)}{R^1\text{—COOH}}$$

wherein $R^1$ is a substituted or unsubstituted phenyl; a substituted or unsubstituted phenylalkyl($C_1$-$C_3$); a substituted or unsubstituted alkyl($C_3$-$C_8$) or a substituted or unsubstituted heteroalkyl (3-8 atoms), the process comprising contacting the substrate with an engineered nitrilase polypeptide of claim 1 under suitable reaction conditions to convert the substrate to the product.

131. The process of claim 130 in which the substrate of formula I is any one of substrates of formula Ia to Ij and the product of formula II are the corresponding products IIa to IIj, wherein (a) the substrate of formula I is Ia:

(Ia)

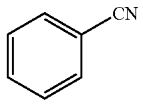

and the product of formula II is IIa:

(IIa)

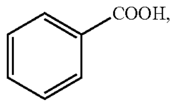

(b) the substrate of formula I is Ib:

(Ib)

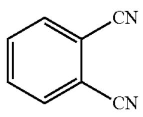

and the product of formula II is IIb:

(IIb)

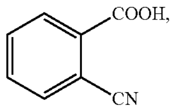

(c) the substrate of formula I is Ic:

(Ic)

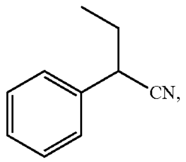

and the product of formula II is IIc':

(IIc′)

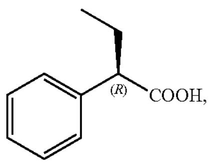

and IIc":

(IIc″)

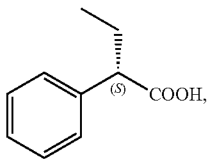

(d) the substrate of formula I is Id:

(Id)

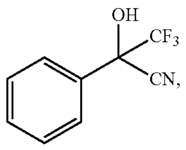

and the product of formula II is IId':

(IId′)

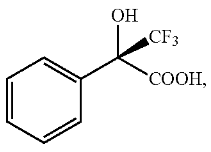

and IId":

(IId″)

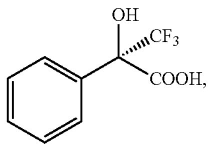

(e) the substrate of formula I is Ie:

(Ie)

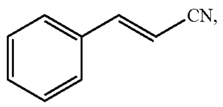

and the product of formula II is IIe':

(IIe′)

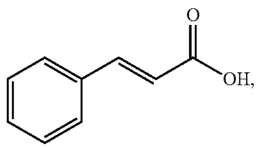

(f) the substrate of formula I is If:

(If)

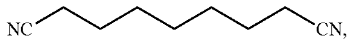

and the product of formula II is IIf:

(IIf)

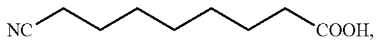

(g) the substrate of formula I is Ig:

(Ig)

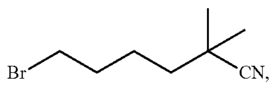

and the product of formula II is IIg:

(IIg)

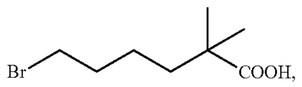

(h) the substrate of formula I is Ih:
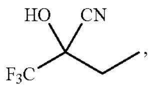
(Ih)
and the product of formula II is IIh:
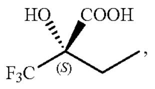
(IIh)
(i) the substrate of formula I is Ii:
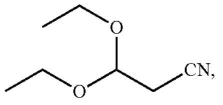
(Ii)
and the product of formula II is IIi:
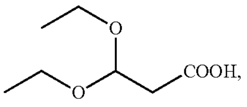
(IIi)
or
(j) the substrate of formula I is Ij:
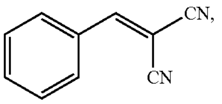
(Ij)
and the product of formula II is IIj:
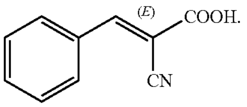
(IIj)
* * * * *